US012723246B2

(12) United States Patent
Budnik et al.

(10) Patent No.: US 12,723,246 B2
(45) Date of Patent: Sep. 1, 2026

(54) ARC PROTEIN EXTRACELLULAR VESICLE NUCLEIC ACID DELIVERY PLATFORM

(71) Applicant: UNIVERSITY OF MASSACHUSETTS, Boston, MA (US)

(72) Inventors: Vivian Budnik, Rutland, MA (US); James Ashley, Chicago, IL (US); Travis Thomson, Worcester, MA (US); Lee Fradkin, Belmont, CA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 789 days.

(21) Appl. No.: 16/770,834

(22) PCT Filed: Dec. 11, 2018

(86) PCT No.: PCT/US2018/065002
§ 371 (c)(1),
(2) Date: Jun. 8, 2020

(87) PCT Pub. No.: WO2019/118497
PCT Pub. Date: Jun. 20, 2019

(65) Prior Publication Data

US 2021/0163933 A1 Jun. 3, 2021

Related U.S. Application Data

(60) Provisional application No. 62/597,145, filed on Dec. 11, 2017.

(51) Int. Cl.

| | |
|---|---|
| ***C12N 15/113*** | (2010.01) |
| ***A61K 9/127*** | (2025.01) |
| ***A61K 47/64*** | (2017.01) |
| ***C12N 15/88*** | (2006.01) |

(52) U.S. Cl.
CPC ............ *C12N 15/113* (2013.01); *A61K 9/127* (2013.01); *A61K 47/64* (2017.08); *C12N 15/88* (2013.01); *C12N 2310/14* (2013.01); *C12N 2310/3513* (2013.01); *C12N 2310/531* (2013.01)

(58) Field of Classification Search
CPC .............. C12N 15/113; C12N 2310/14; C12N 2310/3513; C12N 2310/531; C12N 15/88; A61K 9/127; A61K 47/64; A61K 9/5068; A61K 31/7105; A61K 31/713; A61K 35/64; A61K 38/1709; C07K 2319/21; C07K 2319/24; C07K 14/47
See application file for complete search history.

(56) References Cited

U.S. PATENT DOCUMENTS

| | | | | |
|---|---|---|---|---|
| 10,624,849 B2 * | 4/2020 | Leonard | | A61K 47/46 |
| 2010/0136568 A1 | 6/2010 | Rigby | | 435/6.16 |
| 2015/0093433 A1 | 4/2015 | Leonard et al. | | 424/450 |
| 2016/0298127 A1 | 10/2016 | Ahrens et al. | | |
| 2017/0087087 A1 * | 3/2017 | Leonard | | A61K 31/713 |

FOREIGN PATENT DOCUMENTS

| | | | |
|---|---|---|---|
| WO | WO 2009/042727 | 2/2009 | |
| WO | WO-2009042727 A1 * | 4/2009 | C07K 14/47 |
| WO | WO 2015/002956 | 8/2015 | |
| WO | WO 2018/209113 | 11/2018 | |

OTHER PUBLICATIONS

Mangiamele et al. 2009. Characterization of the Plasticity-Related Gene, Arc, in the Frog Brain. Develop. Neurobiol. 70[12]:813-825 (Year: 2009).*

Morel et al. 2013. Neuronal Exosomal miRNA-dependent Translational Regulation of Astroglial Glutamate Transporter GLT1. J. Biol. Chem. 288[10]7105-7116 (Year: 2013).*

Skotland et al. 2017. Lipids in exosomes: Current knowledge and the way forward. Progress in Lipid Research 66:30-41 (Year: 2017).*

Shepherd. Published Online Sep. 24, 2017. Arc-An endogenous neuronal retrovirus? Seminars in Cell & Developmental Biology 77[2018]:73-78 (Year: 2017).*

Gomes et al. 2020. Extracellular Vesicles in CNS Developmental Disorders. Int. J. Mol. Sci. 21:9428 (Year: 2020).*

Fila et al. 2021. mRNA Trafficking in the Nervous System: A Key Mechanism of the Involvement of Activity-Regulated Cytoskeleton-Associated Protein (Arc) in Synaptic Plasticity. Hindawi Neural Plasticity vol. 2021:Article ID 3468795 (Year: 2021).*

Kobayashi et al. 2005. Identification of a cis-acting element required for dendritic targeting of activity-regulated cytoskeleton-associated protein mRNA. Eur. J. Neurosci. 22:2977-2984 (Year: 2005).*

Russell. The endocytic pathway in animal cells. 2009. (https://commons.wikimedia.org/wiki/File:Endocytic_pathway_of_animal_cells_showing_EGF_receptors,_transferrin_receptors_and_mannose-6-phosphate_receptors.jpg) (Year: 2009).*

Cruceanu et al. 2006. Nucleic acid binding and chaperone properties of HIV-1 Gag and nucleocapsid proteins. Nucl. Acids Res. 34[2]:593-605 (Year: 2006).*

Hantak et al. 2021. Intercellular Communication in the Nervous System Goes Viral. Trends Neurosci. 44[4]:248-259 (Year: 2021).*

Sibarov et al. 2023. Arc protein, a remnant of ancient retrovirus, forms virus-like particles, which are abundantly generated by neurons during epileptic seizures, and affects epileptic susceptibility in rodent models. Front. Neurol. 14:1201104 (Year: 2023).*

Wikipedia. three prime untranslated region. Available online at wikipdeia.org. Accessed on May 2, 2024 (Year: 2024).*

(Continued)

*Primary Examiner* — Nancy J Leith
*Assistant Examiner* — Ruth Sophia Arieti
(74) *Attorney, Agent, or Firm* — Medlen & Carroll, LLP

(57) ABSTRACT

The present invention is related to the field of therapeutic delivery platforms. Such therapeutic delivery platforms are based upon the formation of proteinacous exovesicles that bind nucleic acid payloads (e.g., mRNA, siRNA, shRNA etc.). These nucleic acid payloads may hind to the proteinacous vesicle either directly or as an adduct of a linker molecule. As one example, the linker molecule may be an arc 3'UTR that is bound to an Arc protein exovesicle.

7 Claims, 35 Drawing Sheets

Specification includes a Sequence Listing.

(56) References Cited

OTHER PUBLICATIONS

Wikipedia ("Messenger RNA". Page archived on Nov. 1, 2017. Available at en.wikipedia.org. Accessed on Jul. 15, 2025) (Year: 2017).*

NCBI (2001. Genbank: AC008229.3 *Drosophila melanogaster*, chromosome 2R, region 51E-51F, BAC clone BACR16C17, complete sequence) (Year: 2001).*

NCBI (2013. NCBI Reference Sequence: NM_137111.2 *Drosophila melanogaster* Activity-regulated cytoskeleton associated protein 1 [Arc1], mRNA) (Year: 2013).*

Vesiclepedia ("Description for ACTB". Available online at microvesicles.org. Accessed on Dec. 18, 2025) (Year: 2025).*

Abrusán, et al., "Turning Gold into 'Junk': Transposable Elements Utilize Central Proteins of Cellular Networks." *Nucleic Acids Research*, 41(5):3190-3200 (2013).

Alenquer and Amorim, "Exosome Biogenesis, Regulation, and Function in Viral Infection." *Viruses*, 7(9):5066-5083 (2015).

Alhowikan, "Activity-Regulated Cytoskeleton-Associated Protein Dysfunction May Contribute to Memory Disorder and Earlier Detection of Autism Spectrum Disorders." *Med Princ Pract*, 25(4):350-354 (2016).

Ataman, et al., "Nuclear Trafficking of *Drosophila* Frizzled-2 During Synapse Development Requires the PDZ Protein DGRIP." *Proceedings of the National Academy of Sciences*, 103(20):7841-7846 (2006).

Ataman, et al., "Rapid Activity-Dependent Modifications in Synaptic Structure and Function Require Bidirectional WNT Signaling." *Neuron*, 57(5):705-718 (2008).

Balaj, et al., "Tumour Microvesicles Contain Retrotransposon Elements and Amplified Oncogene Sequences." *Nature communications*, 2(1):1-9 (2011).

Basso and Bonetto, "Extracellular Vesicles and a Novel Form of Communication in the Brain." *Frontiers in neuroscience*, 10:127 (2016).

Basu and Ludlow, "Exosomes for Repair, Regeneration and Rejuvenation." *Expert Opin Biol Ther*, 16(4):489-506 (2016). Posted online 2015.

Batrakova and Kim, "Using Exosomes, Naturally-Equipped Nanocarriers, for Drug Delivery." *J Control Release*, 219:396-405 (2015).

Berkovits and Mayr, "Alternative 3' UTRS Act as Scaffolds to Regulate Membrane Protein Localization." *Nature*, 522(7556):363-367 (2015).

Booth, et al., "Exosomes and HIV Gag Bud from Endosome-Like Domains of the T Cell Plasma Membrane." *The Journal of cell biology*, 172(6):923-935 (2006).

Budnik, et al., "Morphological Plasticity of Motor Axons in *Drosophila* Mutants with Altered Excitability." *Journal of Neuroscience*, 10(11):3754-3768 (1990).

Budnik, "Synapse Maturation and Structural Plasticity at *Drosophila* Neuromuscular Junctions." *Curr Opin Neurobiol*, 6(6):858-867 (1996).

Campillos, et al., "Computational Characterization of Multiple Gag-Like Human Proteins." *Trends Genet*, 22(11):585-589 (2006).

Cao, et al., "Impairment of Trkb-Psd-95 Signaling in Angelman Syndrome." *PLoS Biol*, 11(2):e1001478 (2013).

Chen, et al., "Mesenchymal Stem Cell Secretes Microparticles Enriched in Pre-MicroRNAs." *Nucleic acids research*, 38(1):215-224 (2010).

Chen, "HIV Capsid Assembly, Mechanism, and Structure." *Biochemistry*, 55(18):2539-2552 (2016).

Chowdhury, et al., "ARC/ARG3.1 Interacts with the Endocytic Machinery to Regulate AMPA Receptor Trafficking." *Neuron*, 52(3):445-459 (2006).

Comas-Garcia, et al., "On the Selective Packaging of Genomic RNA by HIV-1." *Viruses*, 8(9) (2016).

Di Rocco, et al., "Towards Therapeutic Delivery of Extracellular Vesicles: Strategies for In Vivo Tracking and Biodistribution Analysis." *Stem cells international*, 2016 (2016).

Dynes and Steward, "Dynamics of Bidirectional Transport of Arc mRNA in Neuronal Dendrites." *Journal of Comparative Neurology*, 500(3):433-447 (2007).

Farris, et al., "Selective Localization of Arc mRNA in Dendrites Involves Activity- and Translation-Dependent mRNA Degradation." *The Journal of Neuroscience*, 34(13):4481-4493 (2014).

Fauré, et al., "Exosomes Are Released by Cultured Cortical Neurones." *Molecular and Cellular Neuroscience*, 31(4):642-648 (2006).

Fromer, et al., "De Novo Mutations in Schizophrenia Implicate Synaptic Networks." *Nature*, 506(7487):179-184 (2014).

Frühbeis, et al., "Emerging Roles of Exosomes in Neuron-Glia Communication." *Front Physiol*, 3:119 (2012).

Frühbeis, et al., "Neurotransmitter-Triggered Transfer of Exosomes Mediates Oligodendrocyte-Neuron Communication." *PLoS Biol*, 11(7):e1001604 (2013).

Gruenberg Van der Goot, "Mechanisms of Pathogen Entry through the Endosomal Compartments." *Nature Reviews Molecular Cell Biology*, 7(7):495-504 (2006).

Guerrero, et al., "Heterogeneity in Synaptic Transmission Along a *Drosophila* Larval Motor Axon." *Nat Neurosci*, 8(9):1188-1196 (2005).

Han, et al., "Exosomes and Their Therapeutic Potentials of Stem Cells." *Stem cells international*, 2016 (2016).

Harris, et al., "Shank Modulates Postsynaptic WNT Signaling to Regulate Synaptic Development." *The Journal of Neuroscience*, 36(21):5820-5832 (2016).

Huleihel, et al., "Matrix-Bound Nanovesicles within ECM Bioscaffolds." *Science advances*, 2(6):e1600502 (2016).

Huotari and Helenius, "Endosome Maturation." *Embo J*, 30(17):3481-3500 (2011).

Jan and Jan, "Antibodies to Horseradish Peroxidase as Specific Neuronal Markers in *Drosophila* and in Grasshopper Embryos." *Proceedings of the National Academy of Sciences*, 79(8):2700-2704 (1982).

Ju, et al., "Exosomes from iPSCS Delivering SiRNA Attenuate Intracellular Adhesion Molecule-1 Expression and Neutrophils Adhesion in Pulmonary Microvascular Endothelial Cells." *Inflammation*, 40(2):486-496 (2017).

Keller, et al., "Exosomes: From Biogenesis and Secretion to Biological Function." *Immunol Lett*, 107(2):102-108 (2006).

Kim, et al., "Tophat2: Accurate Alignment of Transcriptomes in the Presence of Insertions, Deletions and Gene Fusions." *Genome biology*, 14(4):1-13 (2013).

Kim, et al., "Development of Exosome-Encapsulated Paclitaxel to Overcome MDR in Cancer Cells." *Nanomedicine*, 12(3):655-664 (2016).

Koh, et al., "Regulation of DLG Localization at Synapses by Camkii-Dependent Phosphorylation." *Cell*, 98(3):353-363 (1999).

Koles, et al., "Mechanism of Evenness Interrupted (EVI)-Exosome Release at Synaptic Boutons." *Journal of Biological Chemistry*, 287(20):16820-16834 (2012).

Koon, et al., "Autoregulatory and Paracrine Control of Synaptic and Behavioral Plasticity by Octopaminergic Signaling." *Nat Neurosci*, 14(2):190-199 (2011).

Korkut, et al., "Trans-Synaptic Transmission of Vesicular WNT Signals through Evi/Wntless." *Cell*, 139(2):393-404 (2009).

Korkut, et al., "Regulation of Postsynaptic Retrograde Signaling by Presynaptic Exosome Release." *Neuron*, 77(6):1039-1046 (2013).

Kumar, et al., "Exosomes: Natural Carriers for SiRNA Delivery." *Current pharmaceutical design*, 21(31):4556-4565 (2015).

Lander, et al., "Initial Sequencing and Analysis of the Human Genome." *Nature*, 409(6822):860-921 (2001B).

Langmead, et al., "Ultrafast and Memory-Efficient Alignment of Short DNA Sequences to the Human Genome." *Genome Biol*, 10(3):R25 (2009).

Lefebvre, et al., "Comparative Transcriptomic Analysis of Human and *Drosophila* Extracellular Vesicles." *Scientific reports*, 6(1):1-14 (2016).

Li, et al., "Role of Exosomes in Immune Regulation." *Journal of cellular and molecular medicine*, 10(2):364-375 (2006).

Love, et al., "Moderated Estimation of Fold Change and Dispersion for RNA-Seq Data with DESeq2." *Genome biology*, 15(12):1-21 (2014).

(56) References Cited

OTHER PUBLICATIONS

Lyford, et al., "Arc, a Growth Factor and Activity-Regulated Gene, Encodes a Novel Cytoskeleton-Associated Protein That Is Enriched in Neuronal Dendrites." *Neuron*, 14(2):433-445 (1995).
Maniatis, et al., "Regulation of Inducible and Tissue-Specific Gene Expression" Science, 236(4806):1237-1245 (1987).
Mattaliano, et al., "The *Drosophila* ARC Homolog Regulates Behavioral Responses to Starvation." *Molecular and Cellular Neuroscience*, 36(2):211-221 (2007).
Meckes, "Exosomal Communication Goes Viral." *J Virol*, 89(10):5200-5203 (2015).
Myrum, et al., "Arc Is a Flexible Modular Protein Capable of Reversible Self-Oligomerization." *Biochem J*, 468(1):145-158 (2015).
Nallamsetty, et al., "Gateway Vectors for the Production of Combinatorially-Tagged HIS6-MBP Fusion Proteins in the Cytoplasm and Periplasm of *Escherichia coli*." *Protein Sci*, 14(12):2964-2971 (2005).
Nefedova and Kim, "Mechanisms of LTR-Retroelement Transposition: Lessons from *Drosophila melanogaster*." *Viruses*, 9(4):81 (2017).
Nishida, et al., "Roles of R2D2, a Cytoplasmic D2 Body Component, in the Endogenous siRNA Pathway in *Drosophila." Molecular cell*, 49(4):680-691 (2013).
Peebles, et al., "Arc Regulates Spine Morphology and Maintains Network Stability in Vivo." *Proceedings of the National Academy of Sciences*, 107(42):18173-18178 (2010).
Peled, et al., "Evoked and Spontaneous Transmission Favored by Distinct Sets of Synapses." *Curr Biol*, 24(5):484-493 (2014).
Ramachandran, et al., "A Critical Step for Postsynaptic F-Actin Organization: Regulation of BAZ/PAR-3 Localization by APKC and PTEN." *Developmental neurobiology*, 69(9):583-602 (2009).
Roberts and Pachter, "Streaming Fragment Assignment for Real-Time Analysis of Sequencing Experiments." *Nat Methods*, 10(1):71-73 (2013).
Satoh, et al., "Rab11 Mediates Post-Golgi Trafficking of Rhodopsin to the Photosensitive Apical Membrane of *Drosophila* Photoreceptors." *Development*, 132(7):1487-1497 (2005).
Schneider, "Cell Lines Derived from Late Embryonic Stages of *Drosophila melanogaster." J Embryol Exp Morphol*, 27(2):353-365 (1972).
Shabbir, et al., "Mesenchymal Stem Cell Exosomes Induce Proliferation and Migration of Normal and Chronic Wound Fibroblasts, and Enhance Angiogenesis in Vitro." *Stem Cells Dev*, 24(14):1635-1647 (2015).
Shakiryanova, et al., "Activity-Dependent Synaptic Capture of Transiting Peptidergic Vesicles." *Nat Neurosci*, 9(7):896-900 (2006).
Shepherd and Bear, "New Views of Arc, a Master Regulator of Synaptic Plasticity." *Nat Neurosci*, 14(3):279-284 (2011).
Speese, et al., "Nuclear Envelope Budding Enables Large Ribonucleoprotein Particle Export During Synaptic Wnt Signaling." *Cell*, 149(4):832-846 (2012).
Stewart, et al., "Improved Stability of *Drosophila* Larval Neuromuscular Preparations in Haemolymph-Like Physiological Solutions." *Journal of Comparative Physiology A*, 175(2):179-191 (1994).
Thakur, et al., "Double-Stranded DNA in Exosomes: A Novel Biomarker in Cancer Detection." *Cell Res*, 24(6):766-769 (2014).
Trapnell, et al., "Differential Gene and Transcript Expression Analysis of RNA-Seq Experiments with Tophat and Cufflinks." *Nature protocols*, 7(3):562 (2012).
Valadi, et al., "Exosome-Mediated Transfer of mRNAs and MicroRNAs Is a Novel Mechanism of Genetic Exchange between Cells." *Nature cell biology*, 9(6):654-659 (2007).
Van der Pol, et al., "Classification, Functions, and Clinical Relevance of Extracellular Vesicles." *Pharmacol Rev*, 64(3):676-705 (2012).
Viola, el al., "The Tagging and Capture Hypothesis from Synapse to Memory." *Prog Mol Biol Transl Sci*, 122:391-423 (2014).
Wahlgren, et al., Delivery of Small Interfering RNAs to Cells Via Exosomes *siRNA Delivery Methods* (pp. 105-125): Springer. (2016).
Zhang, et al., "Structural Basis of Arc Binding to Synaptic Proteins: Implications for Cognitive Disease." *Neuron*, 86(2):490-500 (2015).
Ashley, et al. "Retrovirus-like Gag Protein Arc1 Binds RNA and Traffics across Synaptic Boutons," Cell, vol. 172, pp. 262-274. 2018.
Budnik, et al. "Extracellular vesicles round off communication in the nervous system," Nature Reviews Neuroscience, vol. 17, Iss. 3, pp. 160-172. 2016.
Skotland, et al. "Lipids in exosomes: Current knowledge and the way forward," Prog Lipid Res, vol. 66, pp. 30-41. 2017.
Pastuzyn, et al., "The Neuronal Gene Arc Encodes a Repurposed Retrotransposon Gag Protein That Mediates Intercellular RNA Transfer." *Cell*, 173(1):275 (2018).
Shahabipour, et al., "Exosomes as Nanocarriers for siRNA Delivery: Paradigms and Challenges." *Archives Of Medical Science: AMS*, 12(6):1324-1326 (2016).

* cited by examiner darc1
darc2
EVs log10 FPKM
Cell log10 FPKM normalized 2-ΔCT
Cell
EVs darc1
-log10 adjusted p-value
log2 fold change Change: 17.9
p<2.7 x 10-8
darc1 counts x 10
cell1
EV1
cell2
EV2
cell3
EV3
cell4
EV4 control dArc1-RNAi1-neuron

Rab11-DN-neuron dArc1-RNAi1-muscle control dArc1-RNAi1-neuron

Rab11-DN-neuron dArc1-RNAi1-muscle

FIG. 3A
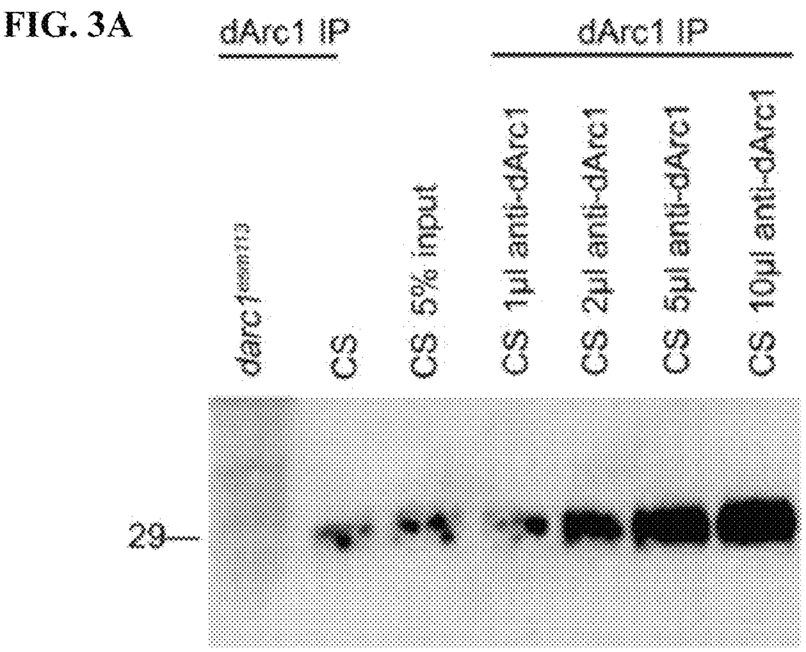
FIG. 3B
FIG. 3C
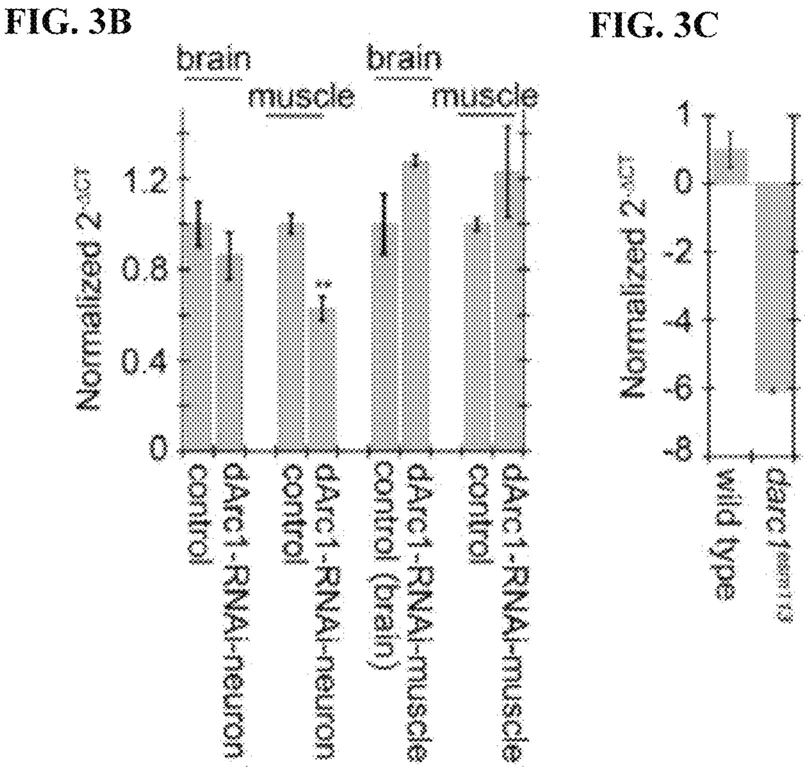

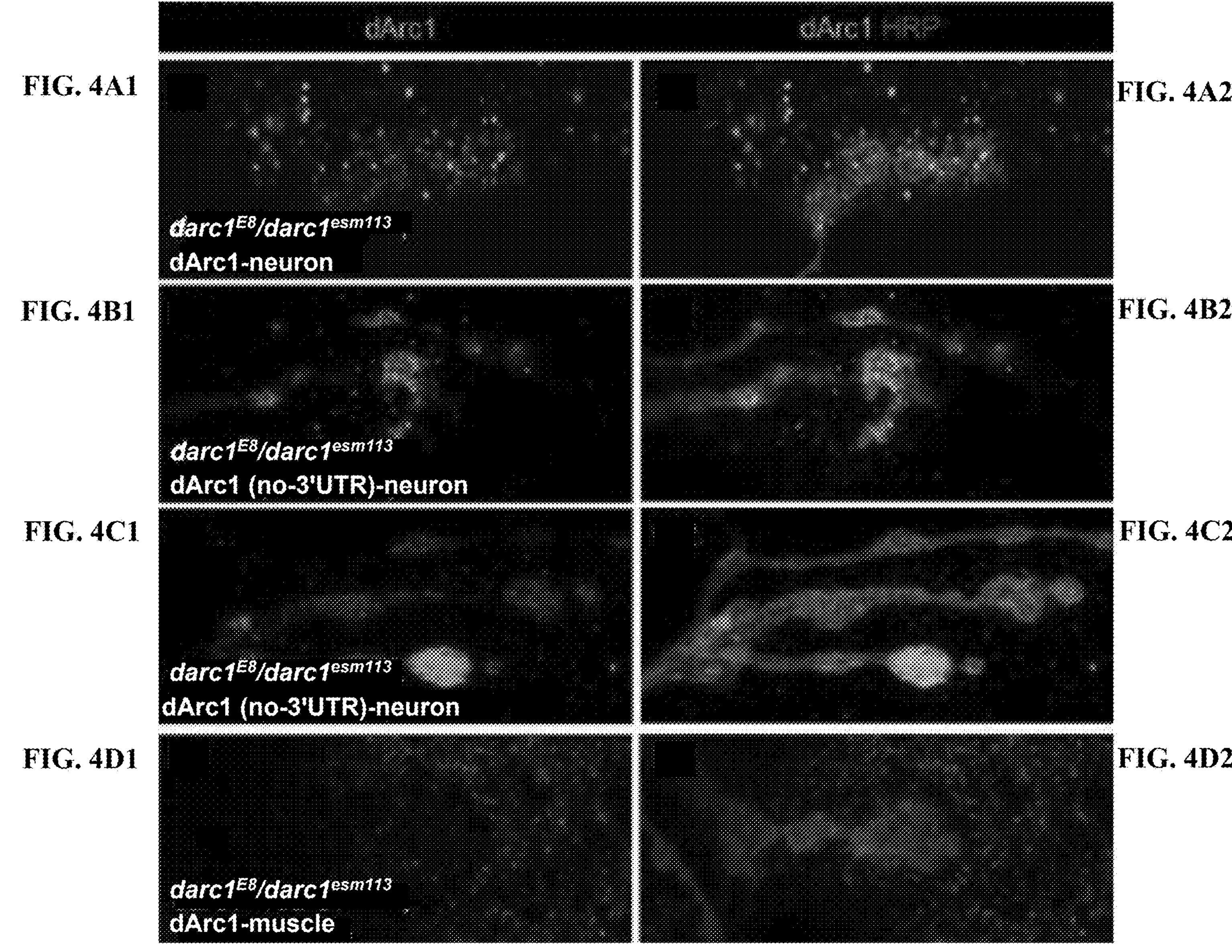
FIG. 4A1 FIG. 4A2
FIG. 4B1 FIG. 4B2
FIG. 4C1 FIG. 4C2
FIG. 4D1 FIG. 4D2

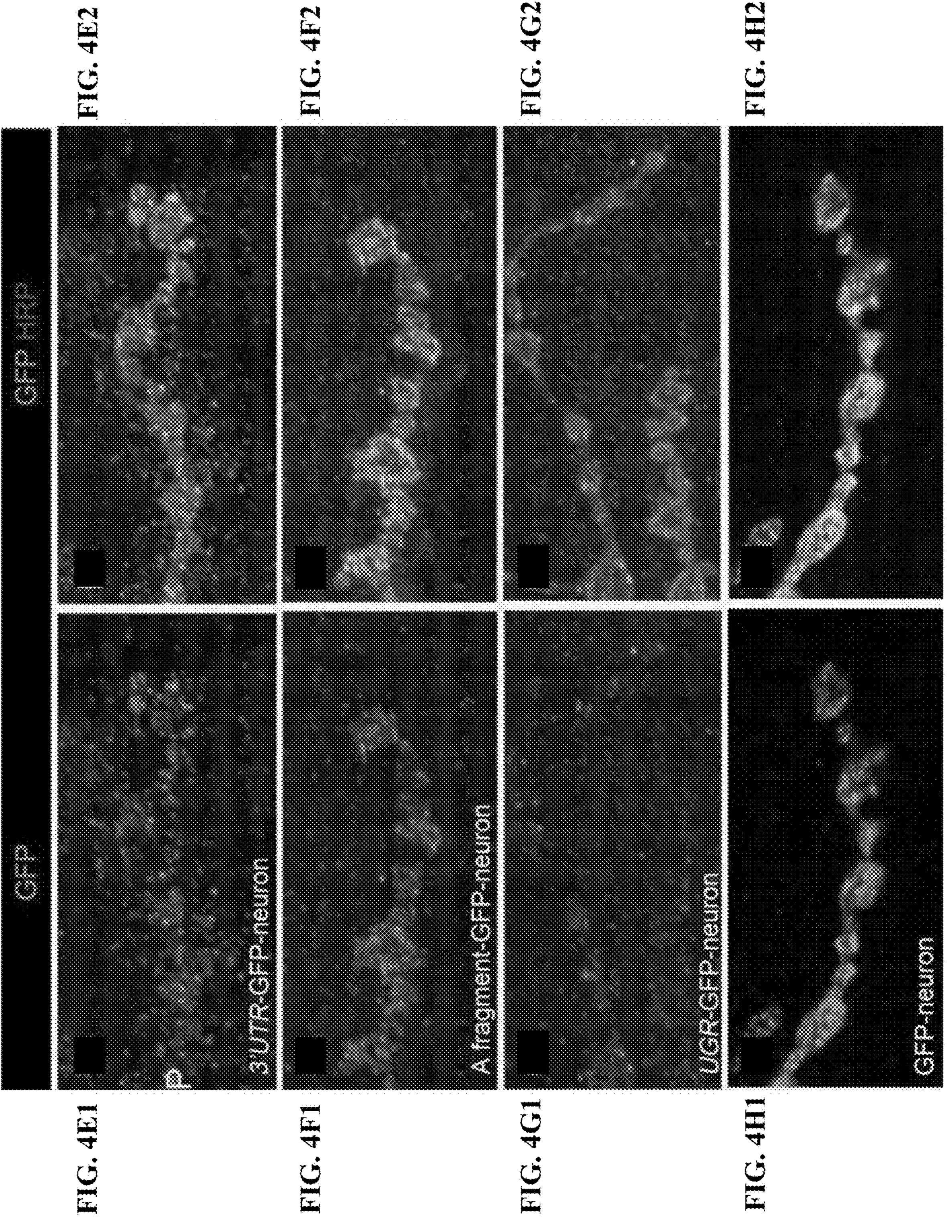
FIG. 4E1 FIG. 4E2
FIG. 4F1 FIG. 4F2
FIG. 4G1 FIG. 4G2
FIG. 4H1 FIG. 4H2

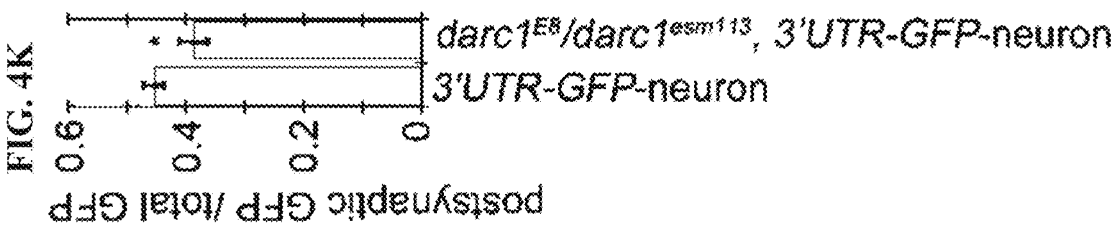
FIG. 4K
darc1E8/darc1esm113, 3'UTR-GFP-neuron
3'UTR-GFP-neuron
0.6
0.4
0.2
0
postsynaptic GFP /total GFP

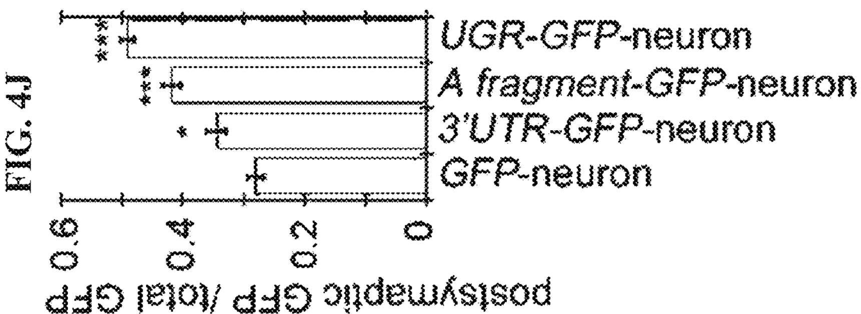
FIG. 4J
UGR-GFP-neuron
A fragment-GFP-neuron
3'UTR-GFP-neuron
GFP-neuron
0.6
0.4
0.2
0
postsymaptic GFP /total GFP

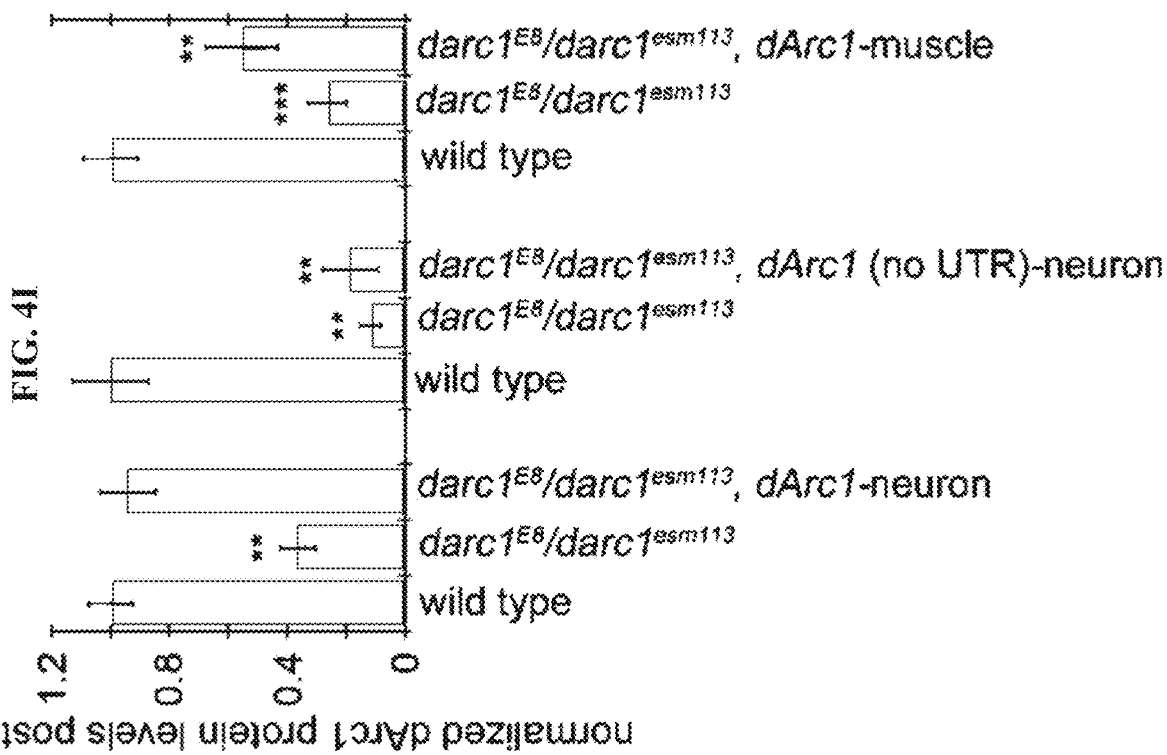
FIG. 4I
darc1E8/darc1esm113, dArc1-muscle
darc1E8/darc1esm113
wild type
darc1E8/darc1esm113, dArc1 (no UTR)-neuron
darc1E8/darc1esm113
wild type
darc1E8/darc1esm113, dArc1-neuron
darc1E8/darc1esm113
wild type
1.2
0.8
0.4
0
normalized dArc1 protein levels post

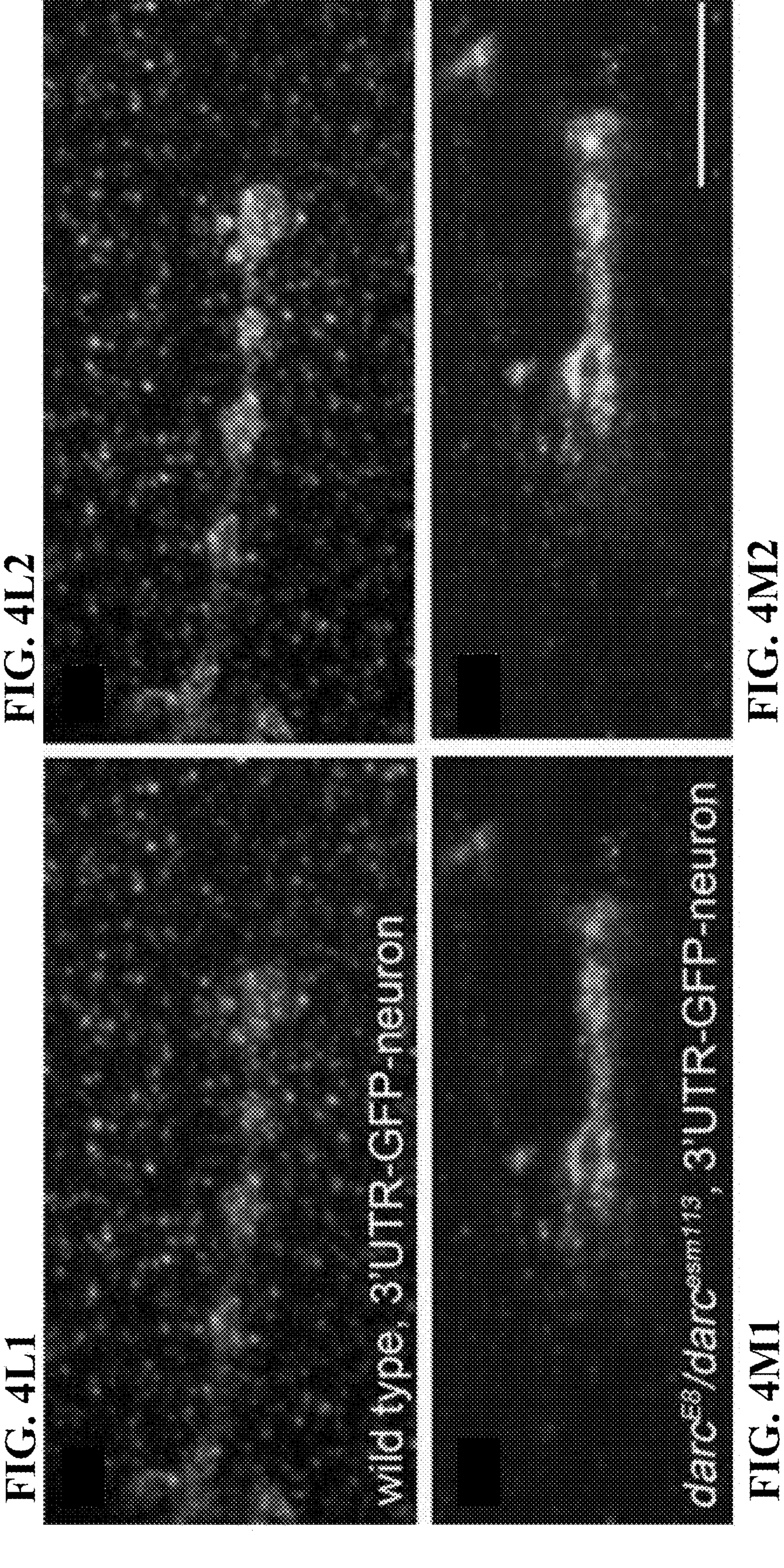
FIG. 4L1
FIG. 4L2
FIG. 4M1
FIG. 4M2

FIG. 5C

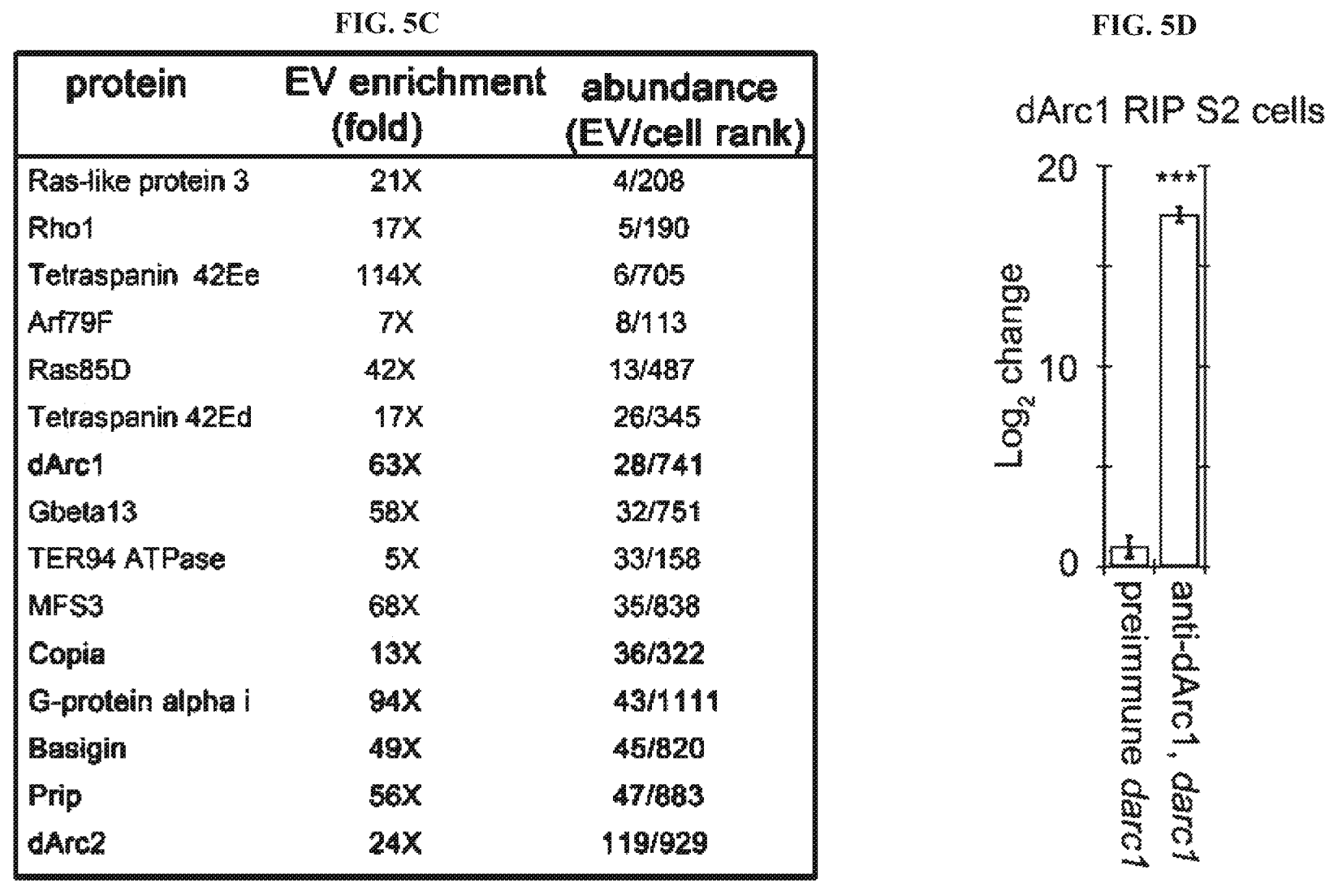

| protein | EV enrichment (fold) | abundance (EV/cell rank) |
|---|---|---|
| Ras-like protein 3 | 21X | 4/208 |
| Rho1 | 17X | 5/190 |
| Tetraspanin 42Ee | 114X | 6/705 |
| Arf79F | 7X | 8/113 |
| Ras85D | 42X | 13/487 |
| Tetraspanin 42Ed | 17X | 26/345 |
| **dArc1** | **63X** | **28/741** |
| Gbeta13 | 58X | 32/751 |
| TER94 ATPase | 5X | 33/158 |
| MFS3 | 68X | 35/838 |
| **Copia** | **13X** | **36/322** |
| G-protein alpha i | 94X | 43/1111 |
| Basigin | 49X | 45/820 |
| Prip | 56X | 47/883 |
| **dArc2** | **24X** | **119/929** |

FIG. 5D

FIG. 5G dArc1-MBP—

Figure 5G:
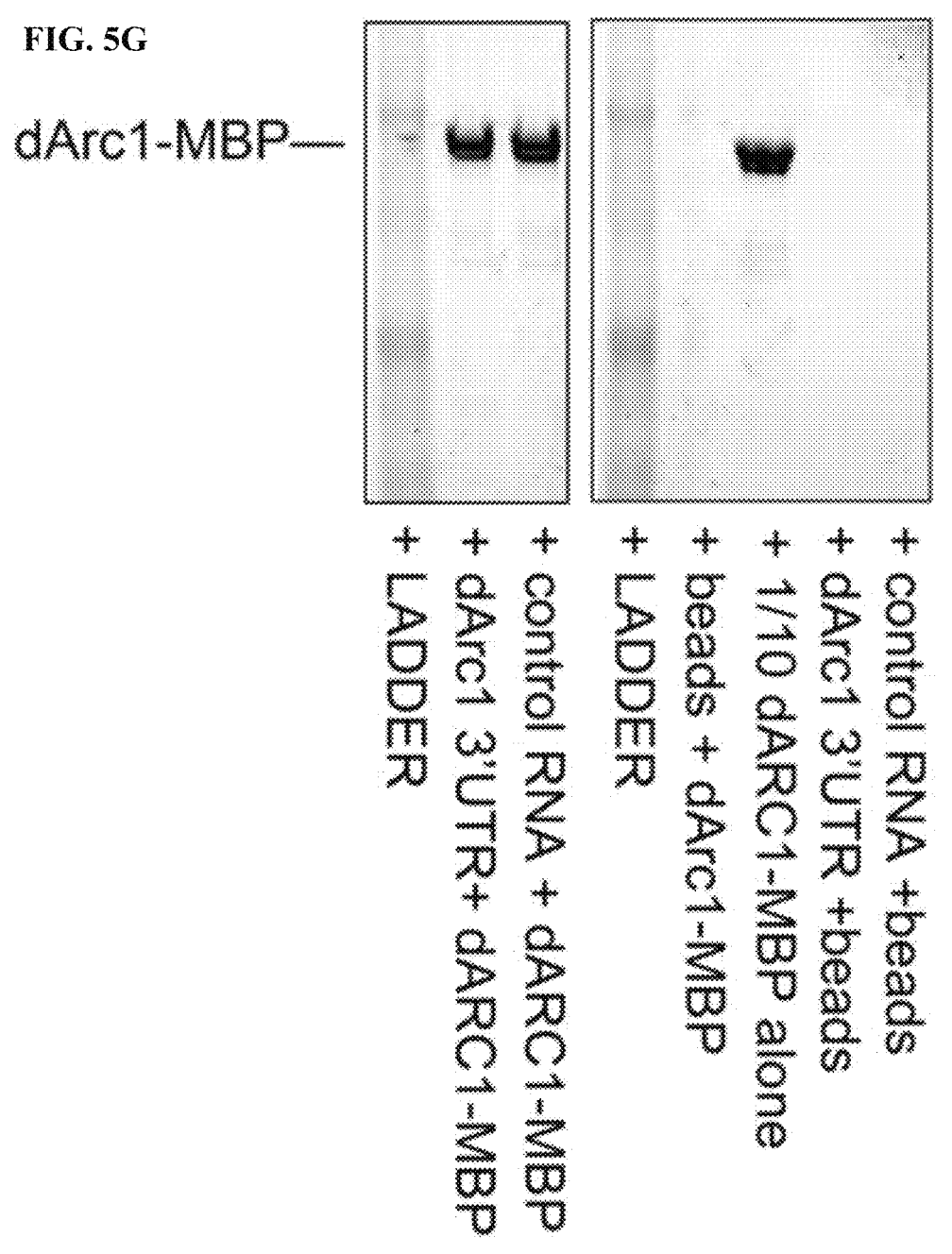

+ LADDER
+ dArc1 3'UTR+ dARC1-MBP
+ control RNA + dARC1-MBP
+ LADDER
+ beads + dArc1-MBP
+ 1/10 dARC1-MBP alone
+ dArc1 3'UTR +beads
+ control RNA +beads

FIG. 7D
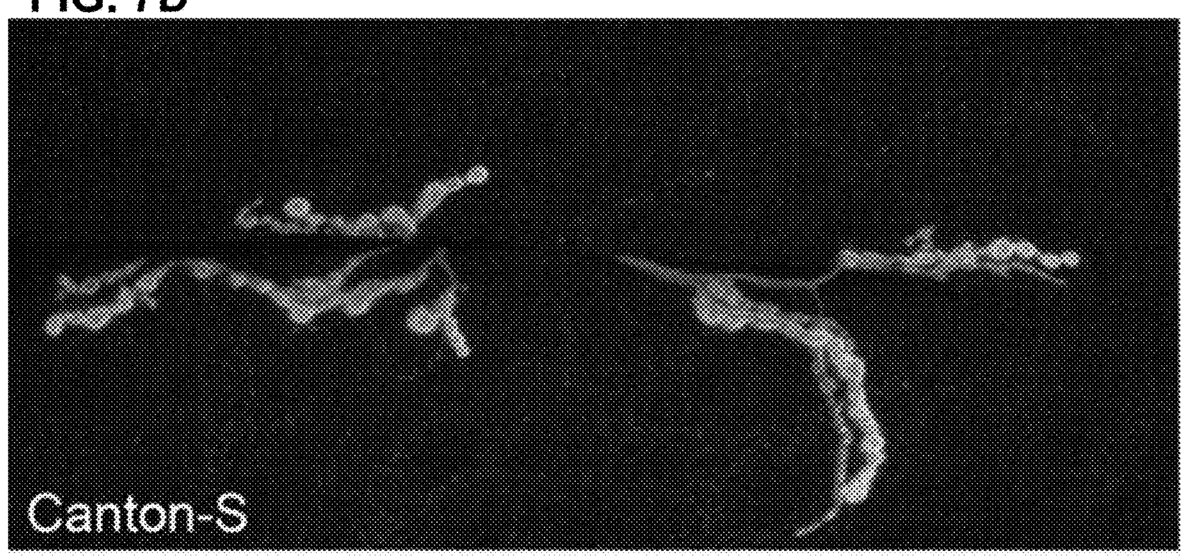
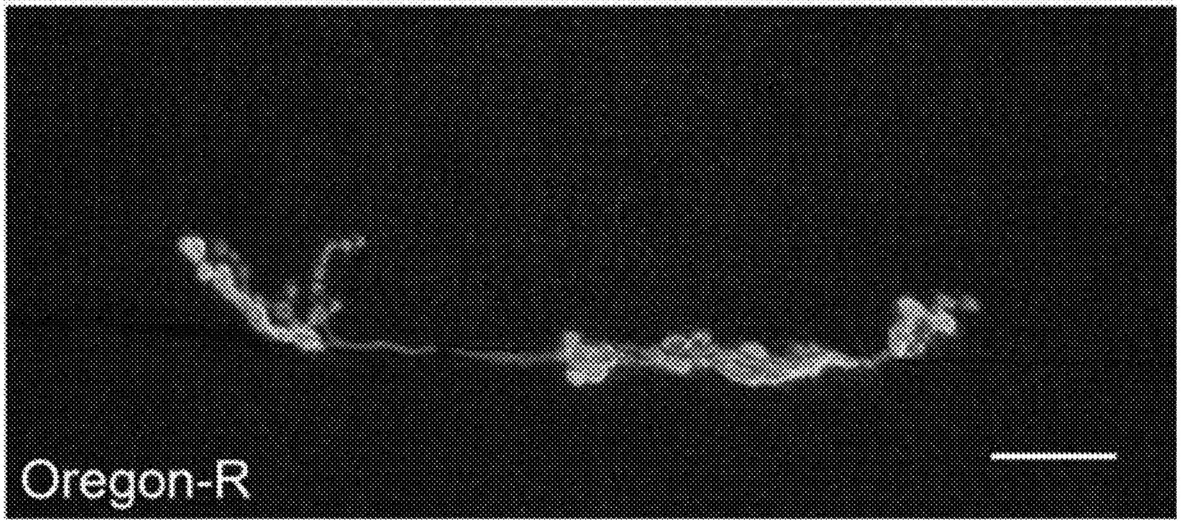
FIG. 7E

FIG. 8A
FIG. 8B
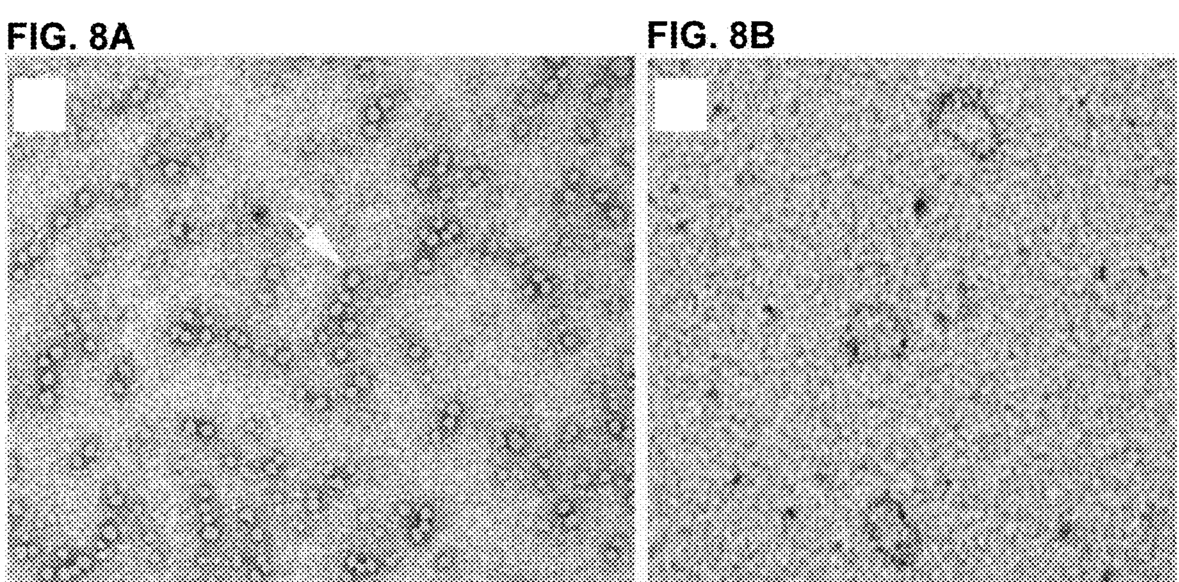
FIG. 8C
FIG. 8D
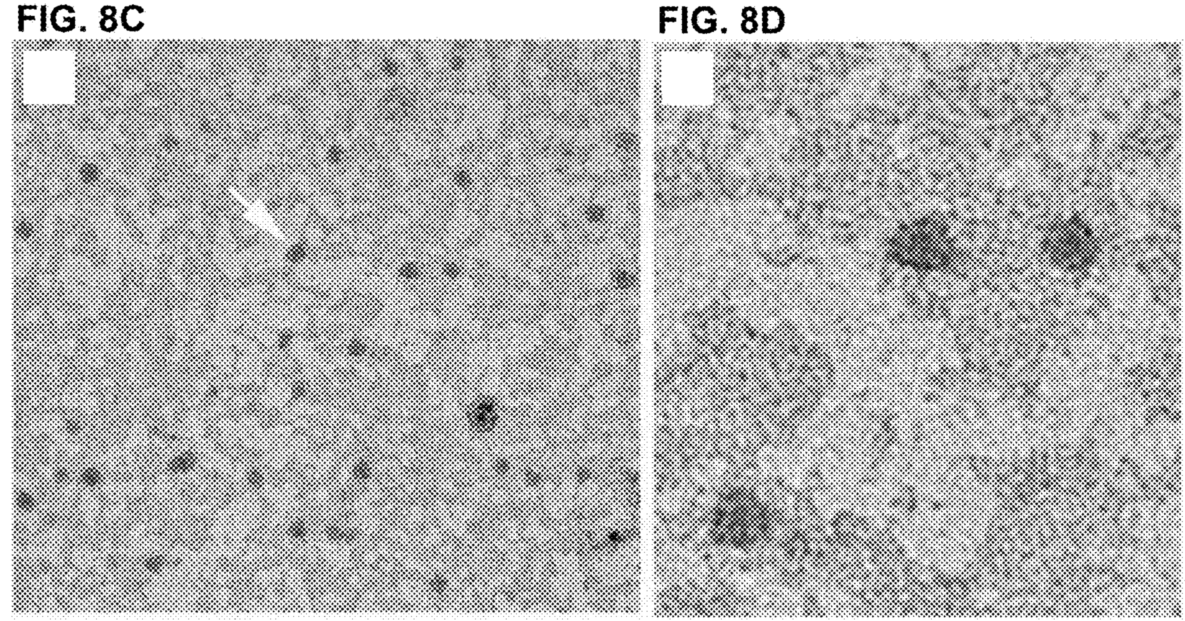

intact EV fraction lysed EV fraction
no primary ab control number of boutons
120
80
40
0
***
wild type
darc1
darc1/darc1
dArc1-RNAi2-neuron
dArc1-RNAi1-neuron
driver control
dArc1-RNAi2-muscle
dArc1-RNAi1-muscle
rescue muscle
rescue neuron
rescue (no 3'UTR) muscle
rescue (no 3'UTR) neuron

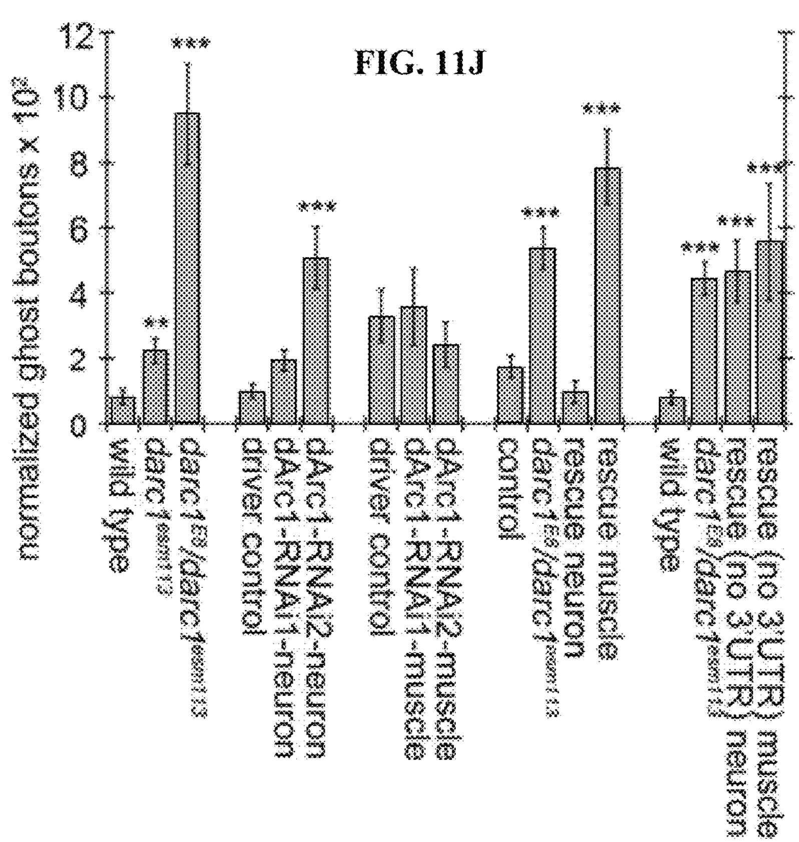
FIG. 11J
normalized ghost boutons x 10²
12
10
8
6
4
2
0
***
**
wild type
darc1
darc1/darc1
driver control
dArc1-RNAi1-neuron
dArc1-RNAi2-neuron
driver control
dArc1-RNAi1-muscle
dArc1-RNAi2-muscle
control
darc1/darc1
rescue neuron
rescue muscle
wild type
darc1/darc1
rescue (no 3'UTR) neuron
rescue (no 3'UTR) muscle
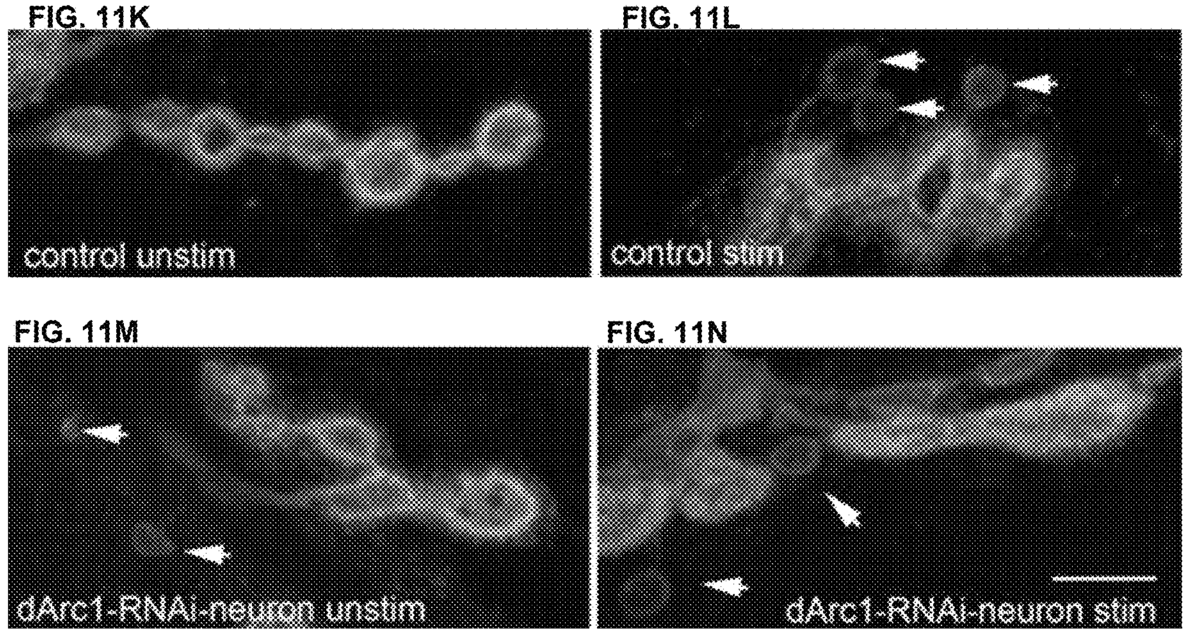
FIG. 11K
control unstim
FIG. 11L
control stim
FIG. 11M
dArc1-RNAi-neuron unstim
FIG. 11N
dArc1-RNAi-neuron stim

SEQUENCE LISTING

```
<160> NUMBER OF SEQ ID NOS: 20

<210> SEQ ID NO 1
<211> LENGTH: 1525
<212> TYPE: DNA
<213> ORGANISM: Artificial Sequence
<220> FEATURE:
<223> OTHER INFORMATION: Synthetic

<400> SEQUENCE: 1

cacctagata gaataggcga caaaaagaac atcaaatacc aacaggcagc agccaacgtc     60
```

```
attgatgacc tcatcgctgc tgccgcccac ccaaacagaa cttttcgtag cctcgccagc    120

cgatcgacgt cagagagagc ccaacaaccg gagagctgga gatggggagc agccacatca    180

acagcagcaa cagcagccac atctcttcat actcttcata ctcactggca atcggcgtgc    240

cggtaagcct cgactagctt ctgaaatcca caaatccacg ctgtttgtat tgctattcgc    300

aatgcctcga aaacggctct attttcatat aatttcacgc cgacttgcgg ctactttggc    360

acagaacgcc agcttttgga aagcaataat ttttattgca acattgaacc tttatttgca    420

actagaaact agatttcgag aatcatcggg cggggcggct gaggatctgg catttcgtcc    480

gtaagatcgg ttattcgcaa tggaggaata tgatattcga accaaatggc gggtgaagtg    540

cctcggcatg gagctccatt ttcttcgaat cttatgtttt gacattgcga gtctgaaatg    600

gatgttgcct gatctccagc cgccccgcac aaccgttgat tctcacaacc gccggctcca    660

ctttgtgccg gtcagcggag aaaaagcgat tatttggcta tcaaaagata tgatcactgt    720

gttgagagac atggcaatca tcgctattgt aaccatatat ttgctgattt ttcgtctgat    780

cctggtcctt tgtgaagcta gcaaaaaacc ccccgcccgg tgaatgccca cttagatcct    840

tttgcaggag gatttcgacg gccctgaagg tgggcgccac ccgtttccgg tagcggcttc    900

ggctgcttcc ggtttccggt gtcgcaaccc ttcgcgatgt cccccgtgcg agtggagcta    960

cagtgggcgt gagccgggca aaacctaaat ttcttcggag atttaaaaaa ccaacaaatt   1020

ttttgacttt tgtcaaaaca attcgaaccc acatagcact acgatggcta acgattcgcc   1080

atccgtgcgg ttggcacgcc aaaactgtct cttcgagatc acgggcctag ggctgtttaa   1140

cattcgaccc aagcgatttc gcgacaggct tcggcacgcc agtatataac ccaaaacaca   1200

caaacgtcag ggctggaac gcgtcactgc cgtgctcctc cagccggcac agtcattccc    1260

cgcccccaca ccaagcaaaa ccggccgctt gtgcagatga cataggcgcg accagccaac   1320

tgacccggct gaccagactt gcaccgtgcg ccatcaactg gaatcttggc cacaagcaca   1380

gcaatagttt ggcccgctat tcccacacag aaacccagag tgggggccta tggaagacca   1440

caagtggttg cgtggaactg ctaaaaatat aaaactgtaa aactaaagac tgaaactaga   1500

aaacaaccat taaactcaga aacgg                                           1525
```

```
<210> SEQ ID NO 2
<211> LENGTH: 767
<212> TYPE: DNA
<213> ORGANISM: Artificial Sequence
<220> FEATURE:
<223> OTHER INFORMATION: Synthetic

<400> SEQUENCE: 2
```

```
cacctagata gaataggcga caaaaagaac atcaaatacc aacaggcagc agccaacgtc     60

attgatgacc tcatcgctgc tgccgcccac ccaaacagaa cttttcgtag cctcgccagc    120

cgatcgacgt cagagagagc ccaacaaccg gagagctgga gatggggagc agccacatca    180

acagcagcaa cagcagccac atctcttcat actcttcata ctcactggca atcggcgtgc    240

cggtaagcct cgactagctt ctgaaatcca caaatccacg ctgtttgtat tgctattcgc    300

aatgcctcga aaacggctct attttcatat aatttcacgc cgacttgcgg ctactttggc    360

acagaacgcc agcttttgga aagcaataat ttttattgca acattgaacc tttatttgca    420

actagaaact agatttcgag aatcatcggg cggggcggct gaggatctgg catttcgtcc    480

gtaagatcgg ttattcgcaa tggaggaata tgatattcga accaaatggc gggtgaagtg    540

cctcggcatg gagctccatt ttcttcgaat cttatgtttt gacattgcga gtctgaaatg    600
```

```
gatgttgcct gatctccagc cgccccgcac aaccgttgat tctcacaacc gccggctcca    660

ctttgtgccg gtcagcggag aaaaagcgat tatttggcta tcaaaagata tgatcactgt    720

gttgagagac atggcaatca tcgctattgt aaccatatat ttgctga                  767


<210> SEQ ID NO 3
<211> LENGTH: 1319
<212> TYPE: DNA
<213> ORGANISM: Artificial Sequence
<220> FEATURE:
<223> OTHER INFORMATION: Synthetic

<400> SEQUENCE: 3

ttgtggcggt tcctccgcaa ggaggccacc acgtggaagg aagccatcgc tctcatccgc     60

gaacacttct cgcccaccaa gcccgcctac cagatctaca tggacttctt ccaaaacaag    120

caggacgacc atgaccccat tgacaccttc gtcatccaga agcgagcgct gctggcccag    180

ctgcccagcg gtcgccacga cgaggaaacg gaactggatc ttctgttcgg tctgctgaac    240

atcaagtacc gcaagcacat ctcccgccac agtgtccata ccttcaagga tctcctggaa    300

cagggccgca tcatcgagca caacaaccag gaggacgagg aacagcttgc cacagcaaag    360

aacacccgtg gctccaagcg caccacccgc tgcacctact gcagtttccg gggcacacc     420

ttcgacaact gccgtaagcg ccagaaggat cggcaggagg agcagcacga ggagtaggcg    480

acaaaaagaa catcaaatac caacaggcag cagccaacgt cattgatgac ctcatcgctg    540

ctgccgccca cccaaacaga acttttcgta gcctcgccag ccgatcgacg tcagagagag    600

cccaacaacc ggagagctgg agatggggag cagccacatc aacagcagca acagcagcca    660

catctcttca tactcttcat actcactggc aatcggcgtg ccggtaagcc tcgactagct    720

tctgaaatcc acaaatccac gctgtttgta ttgctattcg caatgcctcg aaaacggctc    780

tattttcata taatttcacg ccgacttgcg gctactttgg cacagaacgc cagcttttgg    840

aaagcaataa tttttattgc aacattgaac ctttatttgc aactagaaac tagatttcga    900

gaatcatcgg gcggggcggc tgaggatctg gcatttcgtc cgtaagatcg gttattcgca    960

atggaggaat atgatattcg aaccaaatgg cgggtgaagt gcctcggcat ggagctccat   1020

tttcttcgaa tcttatgttt tgacattgcg agtctgaaat ggatgttgcc tgatctccag   1080

ccgccccgca caaccgttga ttctcacaac cgccggctcc actttgtgcc ggtcagcgga   1140

gaaaaagcga ttatttggct atcaaaagat atgatcactg tgttgagaga catggcaatc   1200

atcgctattg taaccatata tttgctgatt tttcgtctga tcctggtcct ttgtgaagct   1260

agcaaaaaac cccccgcccg gtgaatgccc acttagatcc ttttgcagga ggatttcga    1319


<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4

tcagttcaaa tcaccggccg                                                 20


<210> SEQ ID NO 5
<211> LENGTH: 22
<212> TYPE: DNA
<213> ORGANISM: Artificial Sequence
<220> FEATURE:
```

<223> OTHER INFORMATION: Synthetic

<400> SEQUENCE: 5
gtatgtctcg atgttgccga tg 22

<210> SEQ ID NO 6
<211> LENGTH: 3019
<212> TYPE: DNA
<213> ORGANISM: Artificial Sequence
<220> FEATURE:
<223> OTHER INFORMATION: Synthetic

<400> SEQUENCE: 6
caatacatag atacttaatt tggattttaa ttttaataaa aaaaaactaa caaattttct 60
atcgcctgtt agtaattaga ctataagtca ggaatttcgt acgacaatga aaaactataa 120
gttccaagaa aaacactaaa aattcaagaa tgtgagcagc agttctatat tatccaaata 180
gtaagtcagt taataataaa aaataataca ttctattact cgtatacaaa ttataagtaa 240
ccacatatat tgtgaccatt tcacaaaaaa atgtaatagt acaaatcaag gaaaactccc 300
tagaaaccgc atgcaagcct ctacaaaact ttgtttatca gtttgggcca catttacaat 360
caggtttgtc catcagtaca tatagtagtt accggctttc aaactgctat ttttatatag 420
cgcgatgatt cactctgagc aataatacca aaaacataga ccttccctct cttattggct 480
ctccccaatg cctcaagctt tttcgaagtt cgatttcaca acaggcggat ataaaagggc 540
tgcaatgtgg gagagctgtt cagttcaaat caccggccgc attcgctaca ctggctttgt 600
ccgccgactg aaccaagatt aatttgatca cctaacctca cacagcagcg aaaatggccc 660
agcttacaca atggcccagc ttacacagat gaccaacgag cagctccgcg agctgatcga 720
agctgtaaga gcggccgccg tgggcgccgc cggaagtgca gcagcagccg gaggagcaga 780
cgccagcaga ggcaaaggca acttctccgc ttgcacacac agcttcggcg gaacccgcga 840
ccacgacgtg gtcgaggagt tcatcggcaa catcgagaca tacaaggatg tagaaggtat 900
cagcgacgag aacgccctga agggcatctc gctgctgttc tacggtatgg ccagcacctg 960
gtggcaaggc gtccgcaagg aggccaccac gtggaaggaa gccatcgctc tcatccgcga 1020
acacttctcg cccaccaagc ccgcctacca gatctacatg gaattcttcc aaaacaagca 1080
ggacgaccat gaccccattg acaccttcgt catccagaag cgagcgctgc tggcccagct 1140
gcccagcggt cgccacgacg aggaaacgga actggatctt ctgttcggtc tgctgaacat 1200
caagtaccgc aagcacatct cccgccacag tgtccatacc ttcaaggatc tcctggaaca 1260
gggccgcatc atcgagcaca acaaccagga ggacgaggaa cagcttgcca cagcaaagaa 1320
cacccgtggc tccaagcgca ccacccgctg cacctactgc agtttccggg ggcacacctt 1380
cgacaactgc cgtaagcgcc agaaggatcg gcaggaggag cagcacgagg agtaggcgac 1440
aaaaagaaca tcaaatacca acaggcagca gccaacgtca ttgatgacct catcgctgct 1500
gccgcccacc caaacagaac ttttcgtagc ctcgccagcc gatcgacgtc agagagagcc 1560
caacaaccgg agagctggag atggggagca gccacatcaa cagcagcaac agcagccaca 1620
tctcttcata ctcttcatac tcactggcaa tcggcgtgcc ggtaagcctc gactagcttc 1680
tgaaatccac aaatccacgc tgtttgtatt gctattcgca atgcctcgaa aacggctcta 1740
ttttcatata atttcacgcc gacttgcggc tactttggca cagaacgcca gcttttggaa 1800
agcaataatt tttattgcaa cattgaacct ttatttgcaa ctagaaacta gatttcgaga 1860
atcatcgggc ggggcggctg aggatctggc atttcgtccg taagatcggt tattcgcaat 1920

```
ggaggaatat gatattcgaa ccaaatggcg ggtgaagtgc ctcggcatgg agctccattt   1980

tcttcgaatc ttatgttttg acattgcgag tctgaaatgg atgttgcctg atctccagcc   2040

gccccgcaca accgttgatt ctcacaaccg ccggctccac tttgtgccgg tcagcggaga   2100

aaaagcgatt atttggctat caaaagatat gatcactgtg ttgagagaca tggcaatcat   2160

cgctattgta accatatatt tgctgatttt tcgtctgatc ctggtccttt gtgaagctag   2220

caaaaaaccc cccgcccggt gaatgcccac ttagatcctt ttgcaggagg atttcgacgg   2280

ccctgaaggt gggcgccacc cgtttccggt agcggcttcg gctgcttccg gtttccggtg   2340

tcgcaaccct tcgcgatgtc ccccgtgcga gtggagctac agtgggcgtg agccgggcaa   2400

aacctaaatt tcttcggaga tttaaaaaac caacaaattt tttgactttt gtcaaaacaa   2460

ttcgaaccca catagcacta cgatggctaa cgattcgcca tccgtgcggt tggcacgcca   2520

aaactgtctc ttcgagatca cgggcctagg gctgtttaac attcgaccca agcgatttcg   2580

cgacaggctt cggcacgcca gtatataacc caaaacacac aaacgtcagg ggctggaacg   2640

cgtcactgcc gtgctcctcc agccggcaca gtcattcccc gcccccacac caagcaaaac   2700

cggccgcttg tgcagatgac ataggcgcga ccagccaact gacccggctg accagacttg   2760

caccgtgcgc catcaactgg aatcttggcc acaagcacag caatagtttg gcccgctatt   2820

cccacacaga aacccagagt gggggcctat ggaagaccac aagtggttgc gtggaactgc   2880

taaaaatata aaactgtaaa actaaagact gaaactagaa aacaaccatt aaactcagaa   2940

acggaaaact gcgtaattgt ttttatttta tggggtggat gggacaacat ttttacaggg   3000

aatcattttt ttaaacaaa                                                 3019

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7

gatttttcgt ctgatcctgg tc                                               22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8

ccgtttctga gtttaatggt tg                                               22

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9

tggcccagct tacacagatg                                                  20

<210> SEQ ID NO 10
<211> LENGTH: 20
<212> TYPE: DNA
```

<213> ORGANISM: Artificial Sequence
<220> FEATURE:
<223> OTHER INFORMATION: Synthetic

<400> SEQUENCE: 10
gaagttgcct ttgcctctgc 20

<210> SEQ ID NO 11
<211> LENGTH: 29
<212> TYPE: DNA
<213> ORGANISM: Artificial Sequence
<220> FEATURE:
<223> OTHER INFORMATION: Synthetic

<400> SEQUENCE: 11
cacagaacat gaaccttatg ggacgtgtg 29

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
tcggtacaag accatacgat ctgc 24

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
atgctaagct gtcgcacaaa tg 22

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gttcgatccg taaccgatgt 20

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
gggatcaggc aacccgaatg ag 22

<210> SEQ ID NO 16
<211> LENGTH: 39
<212> TYPE: DNA
<213> ORGANISM: Artificial Sequence
<220> FEATURE:
<223> OTHER INFORMATION: Synthetic

<400> SEQUENCE: 16
ctattatcct cttcattata ggatatctga ggcttagtc 39

-continued

```
<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17

cgaccacatg aagcagcacg acttctt                                  27


<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18

cctcggcgcg ggtcttgtag ttg                                      23


<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19

aagaggaacc gccatccaag                                          20


<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20

ctttagcgca tccttgtcgc                                          20
```

ARC PROTEIN EXTRACELLULAR VESICLE NUCLEIC ACID DELIVERY PLATFORM

CROSS REFERENCE

The present application is a U.S. patent application Ser. No. 16/770,834, filed Jun. 6, 2020, which claims priority to a 371 U.S. National Entry of PCT/US18/065002, filed Dec. 11, 2018, now expired, which claims priority to Provisional Application Ser. No. U.S. 62/597,145 filed Dec. 11, 2017, the contents of which are incorporated herein in their entirety.

STATEMENT OF GOVERNMENTAL SUPPORT

This invention was made with government support awarded by the National Institutes of Health, Grant Number MH070000. The government has certain rights in the invention.

A Sequence Listing has been submitted in an ASCII text file named "19248." created on Jun. 5, 2024, consisting of 12.371 bytes, the entire content of which is herein incorporated by reference

FIELD OF THE INVENTION

The present invention is related to the field of therapeutic delivery platforms. Such therapeutic delivery platforms are based upon the formation of proteinacous exovesicles that bind nucleic acid payloads (e.g., mRNA, siRNA, shRNA etc.). These nucleic acid payloads may bind to the proteinacous vesicle either directly or as an adduct of a linker molecule. As one example, the linker molecule may be an arc 3' UTR that is bound to an Arc protein exovesicle.

BACKGROUND

As evidenced by the literature and the existence of a number of companies focused on curing or treating disease by providing nucleic acids (e.g., mRNAs) in vivo, therapeutic delivery of nucleic acids are a promising new modality in molecular medicine. Nucleic acids are, however, unstable and need be encapsulated in vehicles for delivery in vivo. Liposomal and protein complex delivery of nucleic acids can be significantly limited by the host innate and immune systems.

What is needed in the art is a non-immunogenic delivery platform of protecting and delivering nucleic acids are sought. Once such delivery platform might be expected to take advantage of innate extracellular vesicle protein complexes.

SUMMARY OF THE INVENTION

The present invention is related to the field of therapeutic delivery platforms. Such therapeutic delivery platforms are based upon the formation of proteinacous exovesicles that bind nucleic acid payloads (e.g., mRNA, siRNA, shRNA etc.). These nucleic acid payloads may bind to the proteinacous vesicle either directly or as an adduct of a linker molecule. As one example, the linker molecule may be an arc 3' UTR that is bound to an Arc protein exovesicle.

In one embodiment, the present invention contemplates a proteinaceous extracellular vesicle comprising an Arc protein and a therapeutic non-arc nucleic acid. In one embodiment, said therapeutic non-arc nucleic acid is a deoxyribonucleic acid sequence. In one embodiment, said therapeutic non-arc nucleic acid is a ribonucleic acid sequence. In one embodiment, said deoxyribonucleic acid sequence encodes a therapeutic protein. In one embodiment, said ribonucleic acid sequence encodes a therapeutic protein. In one embodiment, said ribonucleic acid sequence is selected from the group consisting of an siRNA, an shRNA and RNAI. In one embodiment, said therapeutic non-arc nucleic acid is linked to a 3' UTR sequence. In one embodiment, said 3' UTR sequence is bound to said Arc protein. In one embodiment, said 3' UTR sequence is an arc mRNA 3' UTR sequence. In one embodiment, said deoxyribonucleic acid sequence further comprises a promoter sequence.

In one embodiment, the present invention contemplates a method, comprising: a) providing; i) a patient comprising a plurality of cells, wherein at least a first cell of said plurality of cells exhibit at least one symptom of a medical condition and a gene of interest; ii) a proteinaceous extracellular vesicle comprising an Arc protein and a therapeutic non-arc nucleic acid; and b) administering said extracellular vesicle to said patient under conditions such that said at least one symptom is reduced. In one embodiment, the method further comprises endocytosing said extracellular vesicle into said at least first cell of said plurality of cells. In one embodiment, said therapeutic non-arc nucleic acid encodes a therapeutic protein. In one embodiment, the method further comprises expressing said therapeutic protein encoded by said therapeutic non-arc nucleic acid. In one embodiment, the method further comprises releasing said therapeutic non-arc nucleic acid into said at least first cell of said plurality of cells. In one embodiment, said released non-arc therapeutic nucleic acid inhibits transcription of a gene of interest of said first cell of said plurality of cells. In one embodiment, said released non-arc therapeutic nucleic acid is selected from the group consisting of an siRNA, an shRNA and an RNAi. In one embodiment, the method further comprises releasing said endocytosed extracellular vesicle from said at least first cell of said plurality of said cells. In one embodiment, the method further comprises incorporating said released endocytosed extracellular vesicle into at least a second cell of said plurality of said cells.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

The term "extracellular vesicle" as used herein, refers to a cell-derived vesicle that is generated by a combination of endocytotic and exocytotic events that result in the encapsulation of various proteins and nucleic acids. Such encapsulation may protect a therapeutic nucleic acid from enzymatic degradation or other environmental stresses (e.g., ionic strength, pH etc.). The association of proteins with an extracellular vesicle provides stability in both extracellular and intracellular environments as well as facilitates a cell-targeting mechanism for cell-cell communication.

The term "Arc protein" as used herein, refers to an activity-regulated cytoskeleton protein associated with neuronal plasticity that can be encapsulated into an extracellular vesicle.

The term "therapeutic non-arc nucleic acid" as used herein, refers to any nucleic acid that is not a portion of, or transcribed from, the arc gene.

The term "therapeutic protein" as used herein, refers to any therapeutic protein that is expressed from a non-arc nucleic acid.

The term "3' UTR sequence" as used herein, refers to an mRNA-derived 3' untranslated repeat sequence that is capable of binding to a protein within an extracellular vesicle. For example, an arc 3'UTR sequence may bind to an Arc protein within an extracellular vesicle. Such 3' UTR binding to a protein may occur with only the 3' UTR sequence, or when the 3' UTR sequence is linked to a non-arc nucleic acid.

The term "endocytosis", "endocytose", "endocytosing" or "endocytosed" as used herein, refers to the incorporation of substances into a cell by phagocytosis or pinocytosis.

The term "incorporate", "incorporating" or "incorporated" as used herein, refers to the passage of a compound or substance through a cell membrane such that it passes from the extracellular environment into the intracellular environment. In some cases, the incorporation process (e.g., endocytosis) releases cell membrane such that the compound or substance becomes encapsulated and a vesicle is created.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90 lower than the quantity and/or magnitude of the symptoms in the untreated subject.

The term "injury" as used herein, denotes a bodily disruption of the normal integrity of tissue structures. In one sense, the term is intended to encompass surgery. In another sense, the term is intended to encompass irritation, inflammation, infection, and the development of fibrosis. In another sense, the term is intended to encompass wounds including, but not limited to, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, burn injuries etc.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "derived from" as used herein, refers to the source of a compound or sequence. In one respect, a compound or sequence may be derived from an organism or particular species. In another respect, a compound or sequence may be derived from a larger complex or sequence.

The term "test compound" as used herein, refers to any compound or molecule considered a candidate as an inhibitory compound.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways. wherein the compounds interfere with gene expression.

As used herein, the term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it.

As used herein, the term "microRNA", "miRNA", or "pRNA" refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

The term "in operable combination" as used herein, refers to any linkage of nucleic acid sequences in such a manner that a nucleic acid molecule capable of directing the transcription of a given gene and/or the synthesis of a desired protein molecule is produced. Regulatory sequences may be operably combined to an open reading frame including but not limited to initiation signals such as start (i.e., ATG) and stop codons, promoters which may be constitutive (i.e., continuously active) or inducible, as well as enhancers to increase the efficiency of expression, and transcription termination signals.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., *Science* 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5'non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenyation.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

BRIEF DESCRIPTION OF THE FIGURES

FIG. 1A: Comparison of RNA expression levels in EV versus cellular RNA from S2 cells determined by deep sequencing, and enrichment of darc1 (red) in the EV fraction. Note that darc2 mRNA (blue) levels are not statistically different from cellular levels.

FIG. 1B: Volcano Plot of RNA-Seq data from 4 replicates, where the x-axis represents fold change in transcripts from EVs vs. total cellular mRNA levels (a positive score represents enrichment, a negative score represents depletion). The y-axis represents statistical confidence for each x-axis point. Green circles are transcripts that are significantly enriched. darc1 is encircled by a red marker.

FIG. 1C: A normalized $2^{-\Delta CT\ comparision\ of\ darc}$1 trancript enrichment between cells and EVs.

FIG. 1D: Raw number of RNA-seq reads for darc1 from 4 biological RNA-Seq replicates.

FIG. 2A: a darc1 FISH probe with wild type darc1

FIG. 2B: a darc1 FISH probe with darc1esm113 mutant

FIG. 2C: an anti-dArc1 with wild type darc1

FIG. 2D: an anti-dArc1 in darc1E8/darc1esm113 mutants.

Numbers at the left of the blots represent molecular weight in kilodaltons. Arrow points to an unspecific band labeled by the dArc1 antibody. Tub-tubulin. Calibration bar is 6 sm; N-(from left to right; animals/arbors) M(6/11, 6/10), N(12/16, 6/10, 6/10), O(8/14, 8/13, 8/15, 8/16), P(21/44, 12/24, 9/14, 18/29, 9/17, 9/14), Q(8/14, 8/13), R(15/28, 15/28); Data are represented as mean and error bars represent SEM; statistical analysis was conducted using student's t-test for M and one-way ANOVA with Tukey Post Hoc test for the rest of the graphs. *=p<0.05; =p<0.001; *=p<0.0001.

FIGS. 3A-3C present exemplary data showing dArc1 immunoprecipitation and darc1 RNA levels.

FIG. 3A: Western blot showing dArc1 immunoprecipitation from body wall muscle extracts derived from wild type (CS) and darc1esm113 mutants labeled with anti-dArc1. Number at the left of the blot represents molecular weight in kilodaltons.

FIG. 3B: darc1 qRT-PCR performed on RNA isolated from either dissected body wall muscles or brains in the indicated genotypes.

FIG. 3C: darc1 RT-qPCR performed on RNA isolated from wild type larval body wall and darc1esm113.

N (biological replicates per genotype from left to right) is B:6,5,4,4; C 3 for each genotype; Graphs represent mean, and error bars SEM; statistical analysis was performed using a Student's t-test; *=p<0.05; =p<0.001; *=p<0.0001.

FIGS. 4A1-4M2 present exemplary data of darc1 mRNA and dArc1 protein transfer across synaptic boutons depends on darc1 3'UTR.

FIGS. 4A1-4D2: Confocal slices of NMJ branches from darc1 mutant larvae expressing dArc1 transgenes either (A,D) containing, or (B,C) lacking the 3'UTR, double labeled with antibodies to dArc1 and HRP. Transgenes were expressed in (A-C) neurons or (D) muscles.

FIGS. 4E1-4H2: Confocal slices of NMJ branches in preparations double labeled with GFP and HRP from larvae expressing neuronal (E) darc1 3'UTR, (F) darc1 3'UTR A-fragment, and (G) UGR sequence, fused to GFP. In (H) GFP alone is expressed in neurons.

FIGS. 4I-4K: Quantification of (I) dArc1 immunoreactive and (J,K) GFP immunoreactive signal in the indicated genotypes.

FIG. 4L1-4M2: Diagram of darc1 mRNA showing the 5' (blue), the ORF encoding (red), and 3' (green) UTR. The black lines underneath represent different portions of the darc1 transcript testing the darc1 localization signal.

Calibration bar is 8 μm; N=(from left to right; animals/arbors) I(10/13, 10/13, 10/23, 9/17, 9/15, 9/13, 9/19, 9/17, 9/15), J(9/18, 15/27, 9/18, 9/16), K(10/29, 10/25). Data are represented as mean and error bars represent SEM; statistical analysis was conducted using one-way ANOVA with Tukey post hoc test for I,J, and Student's t-test for K. *=p<0.05; =p<0.001; *=p<0.0001.

FIG. 5A-5G present exemplary data of enrichment of Copia-retrotransposon RNA and protein in S2 cell EVs and darc1 mRNA association with dArc1 protein.

Figure 5A:
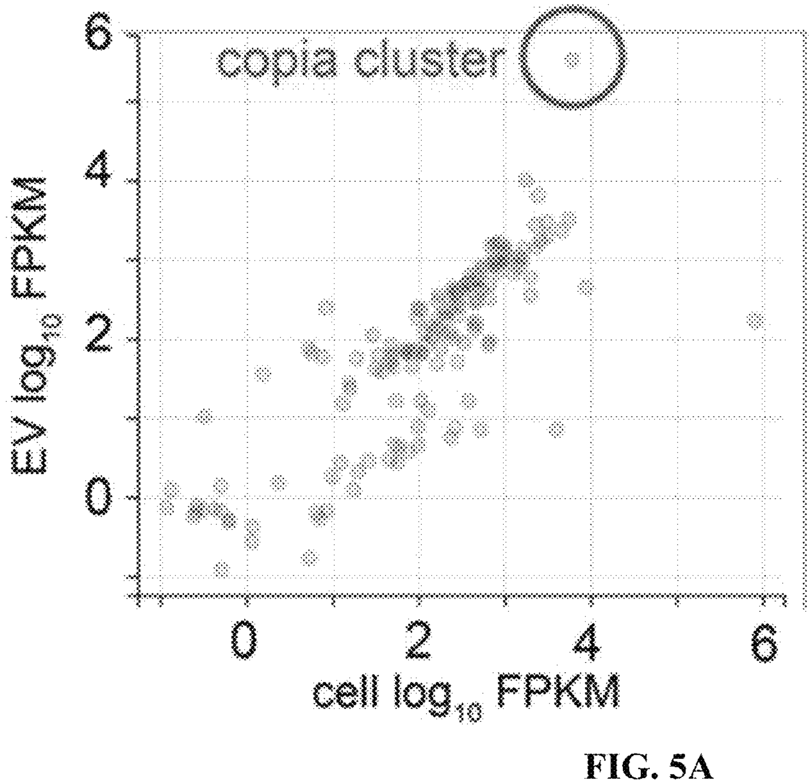

FIG. 5A: Enrichment of copia mRNA in the S2 EV fraction.

Figure 5B:
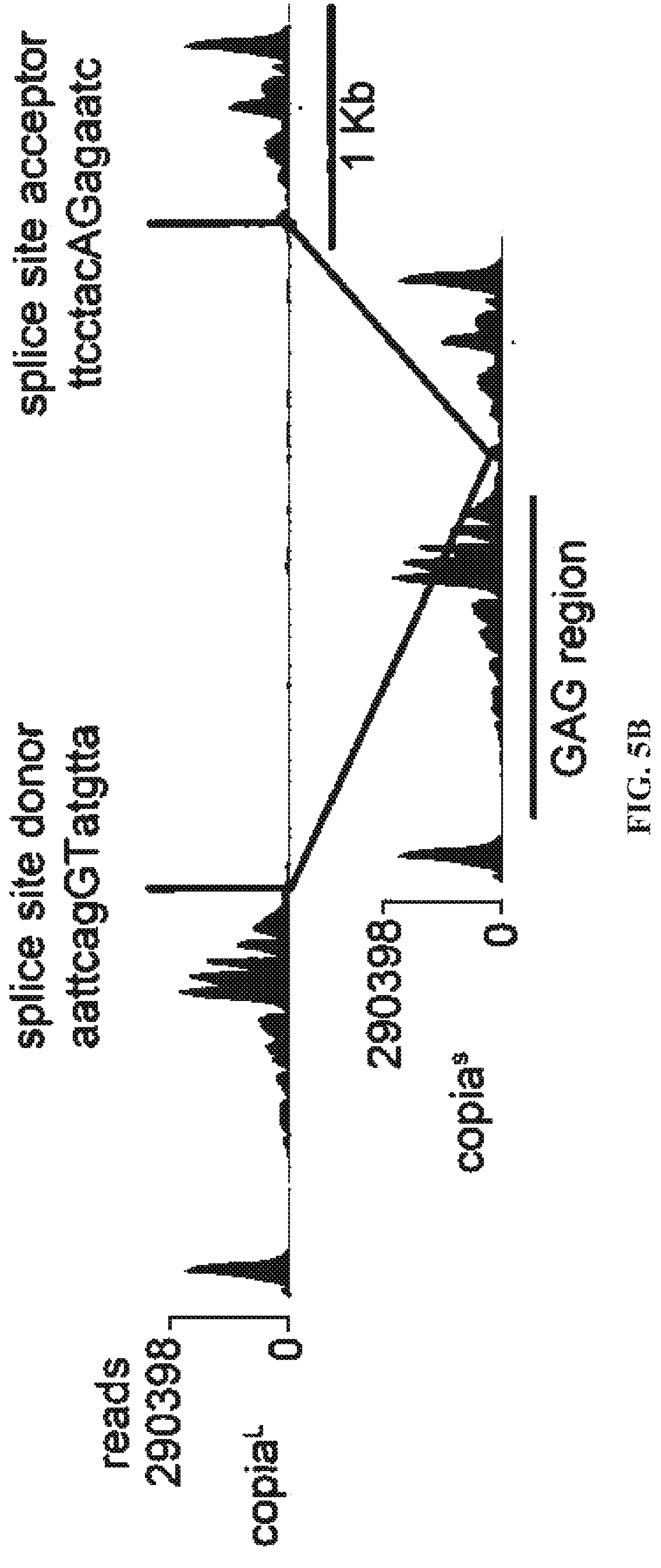

FIG. 5B: Long (L) and short (S) copia isoforms, predicted to be generated by alternative RNA splicing, and enrichment of copia$^S$, encoding the Gag region, in EVs.

FIG. 5C: Selected proteins showing enrichment in S2 cell EVs and their abundance in the EV vs cellular fractions, highlighting dArc1, dArc2 and Copia.

Figure 5E:
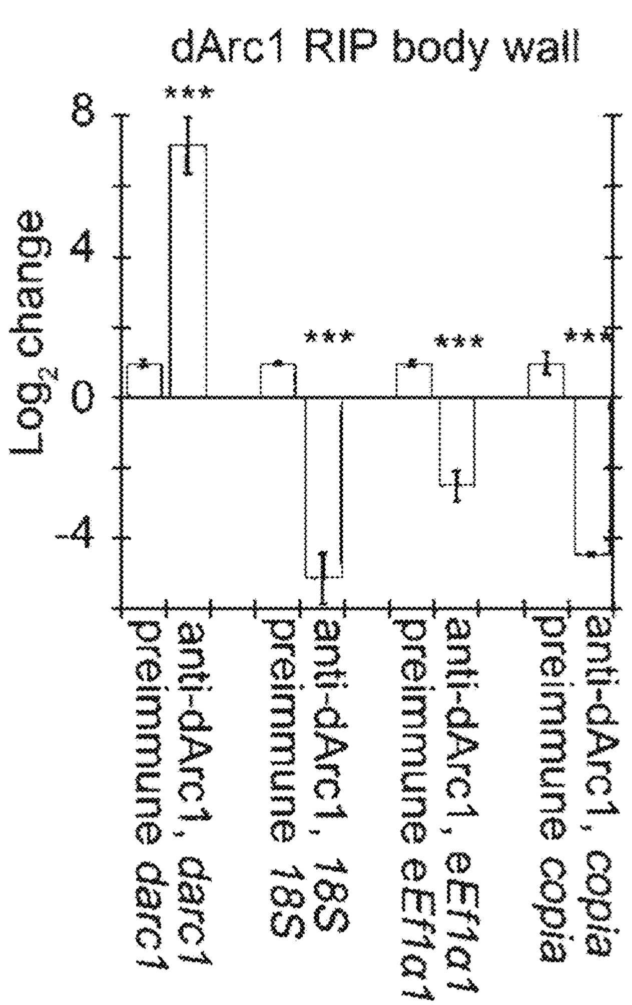

FIGS. 5D and 5E: Immunoprecipitation of darc1 RNA using anti-dArc1 antibodies from extracts of (D) S2 cells and (E) body wall muscles.

Figure 5F:
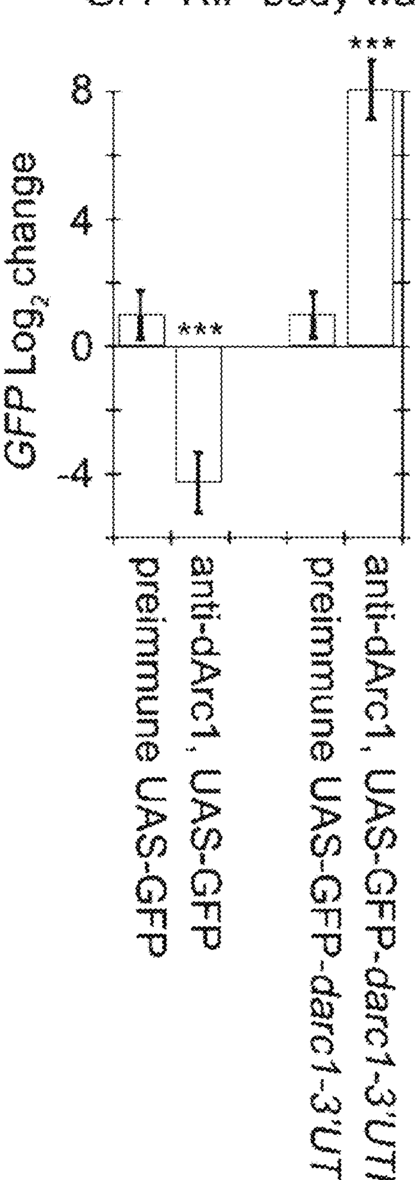

FIG. 5F: Immunoprecipitation of GFP RNA using anti-dArc1 antibodies from extracts of body wall muscles with neurons expressing either GFP alone or GFP upstream of the darc1 3'UTR.

FIG. 5G: Biotinylated RNA pull down of dArc1 protein, using biotinylated darc1 3'UTR RNA or control RNA. Both pull down dArc1 protein, while beads or RNA alone do not.

N=3 biological repeats for FIGS. 5D, 5E, 5F; data are represented as mean and error bars represent SEM; statistical analysis was conducted using student's T-test; *=p<0.05; =p<0.001; *=p<0.0001.

Figure 6:
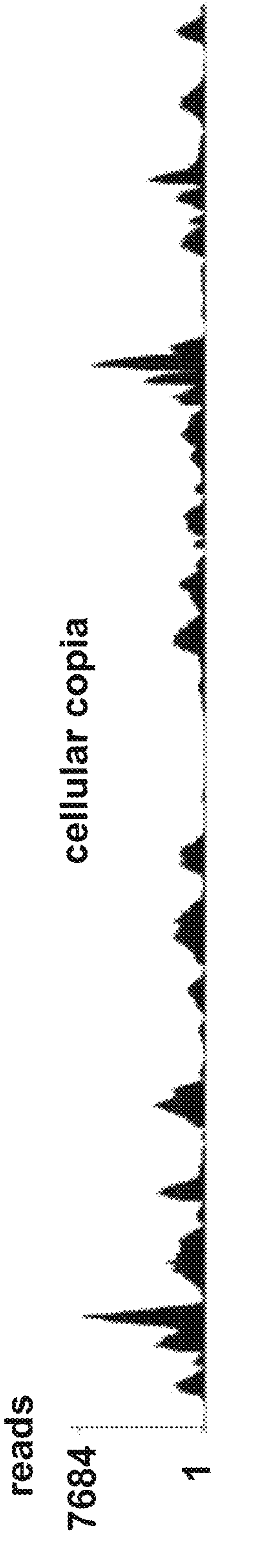

FIG. 6 presents a full-length copia$^L$ transcript found in the cellular fraction. Raw number of RNA-seq reads for cellular Copia showing reads across the entire predicted transcript.

FIGS. 7A-F present exemplary consequences of the UGR for darc1 expression and NMJ morphology, and a proposed model of dArc1 transfer (MVB=multivesicular body, SV=synaptic vesicle, AZ=active zone, SSR=subsynaptic reticulum).

Figure 7A:
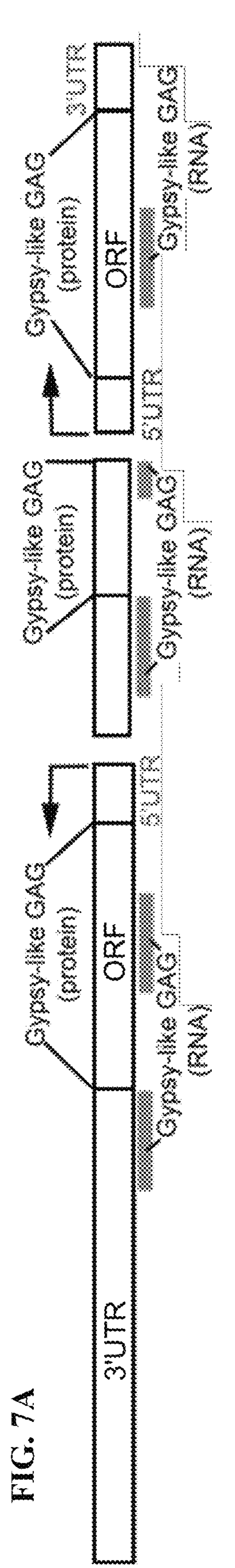

FIG. 7A: Diagram of the darc1 genomic region in OR showing the UGR element between the darc1 and darc2 genes.

Figure 7B:
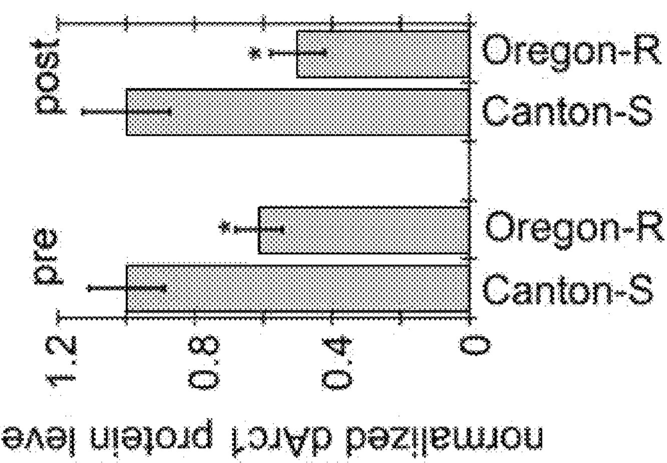
Figure 7C:
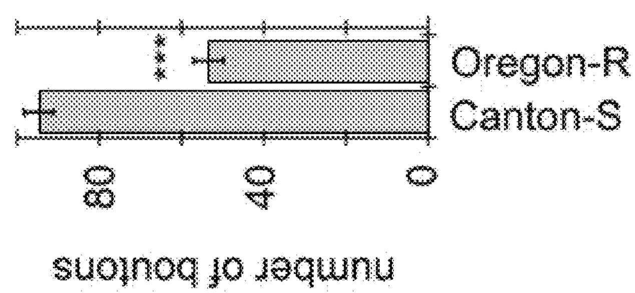

FIGS. 7B and 7C: Quantification in the indicated genotypes of (B) anti-dArc1 signal and (C) number of synaptic boutons.

FIGS. 7D and 7E: Merged confocal Z-stacks of NMJ arbors labeled with antibodies to HRP and DLG in (D) Canton-S and (E) Oregon-R.

Figure 7F:
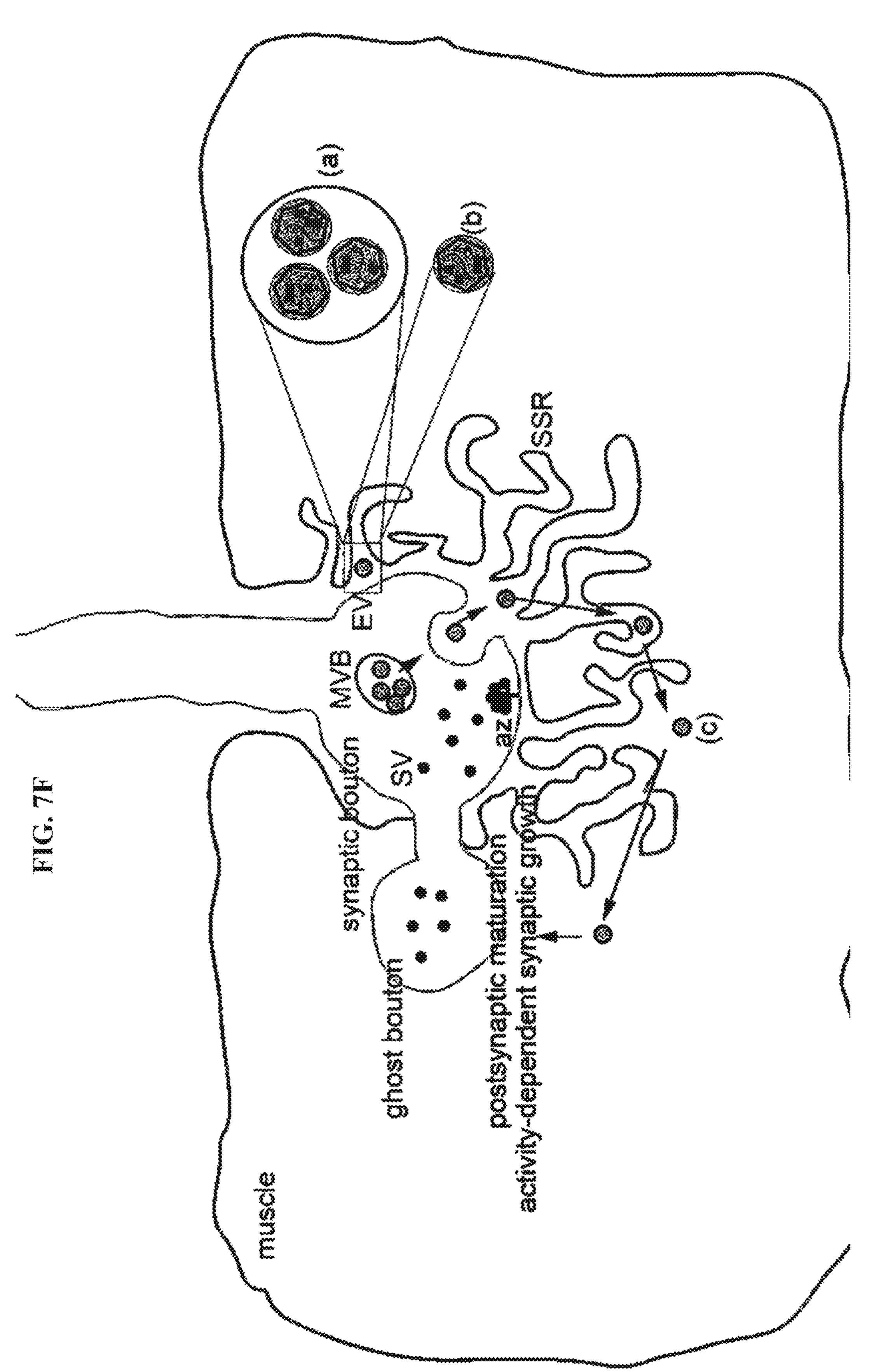

FIG. 7F: Diagram depicting a larval NMJ, in which exosome-like vesicles (EV) containing dArc1 protein and transcript are packaged then released from non-synaptic sites.

Calibration bar is 26 μm; N=(from left to right; animals/arbors) B(12/12,12/24), C(6/10,6/12); data are represented as mean and error bars represent SEM. Statistical analysis was conducted using student's T-test. *=p<0.05; =p<0.001; *=p<0.0001.

Figure 8E:
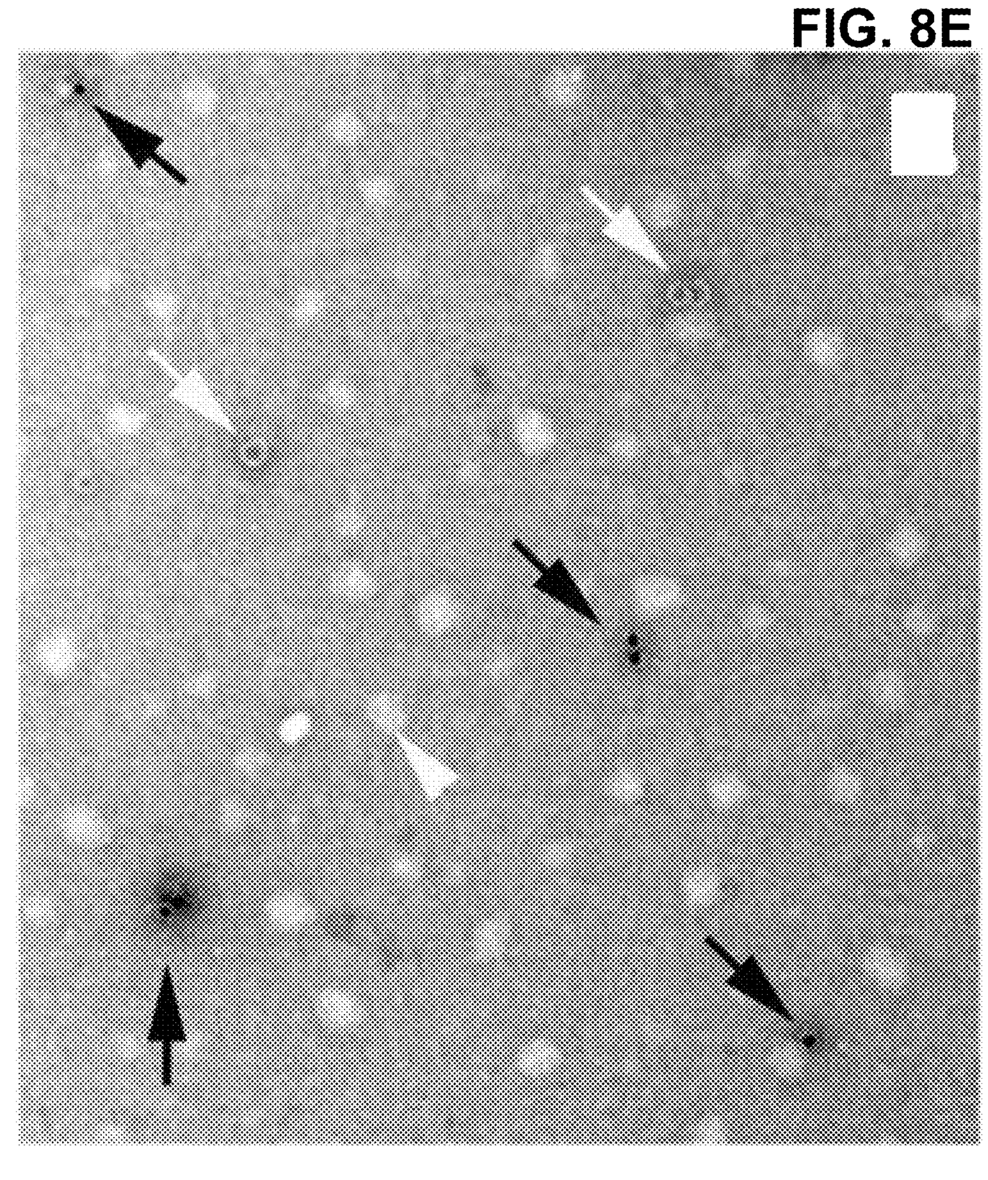

FIGS. 8A-8G present exemplary data showing that purified dArc1 protein assembles into capsid-like structures and these structures are contained in EVs FIGS. 8A and 8B: Negatively stained capsid-like structures (white arrow) formed by purified dArc1 protein shown at (A) low and (B) high magnification.

FIGS. 8C and 8D: Capsid-like structures (white arrow) observed after EV lysis, shown at (A) low and (B) high magnification.

Figures 8F, 8G:
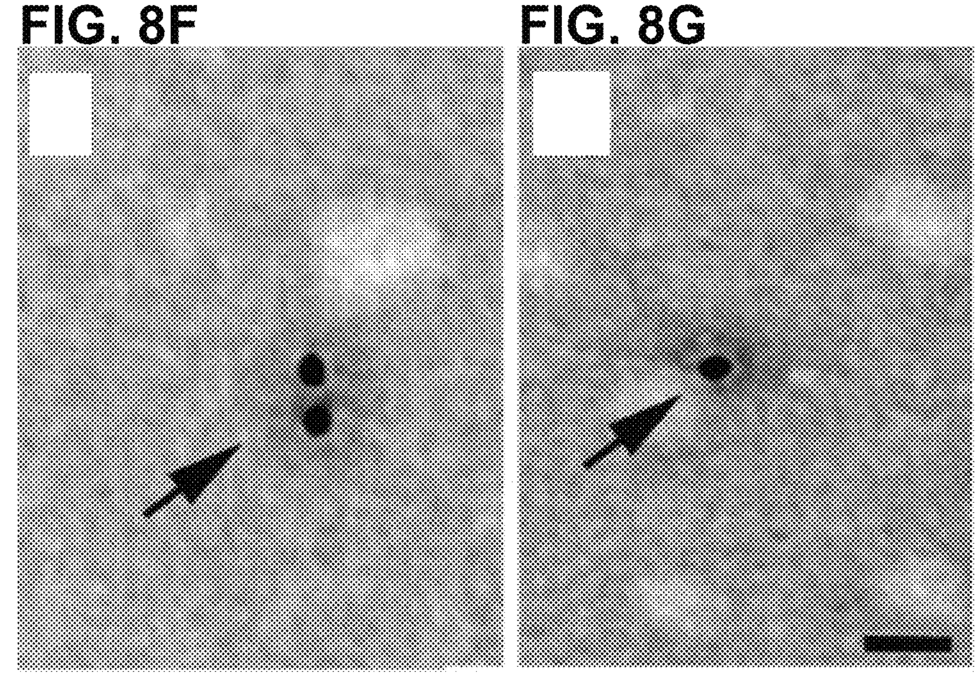

FIGS. 8E and 8G: Anti-dArc1 ImmunoEM labeling of capsid-like structures (black arrows) derived from lysed EVs, shown at (E) low and (F,G) high magnification.

White arrows point to unlabeled capsid like structures. Calibration bar is 120 nm for A,C,E and 40 nm for B,D,F,G.

Figures 9A, 9B:
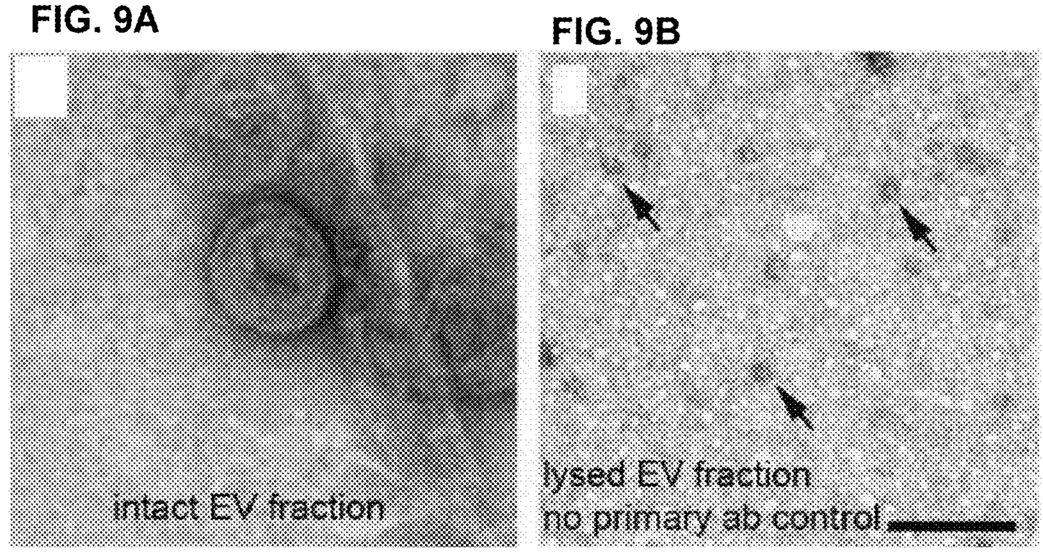

FIGS. 9A and 9B present exemplary data showing capsid-like structures in EVs. Calibration bar is 70 nm in A and 350 nm in B.

FIG. 9A: Ultrastructure of negatively stained exosomal fraction without saponin treatment FIG. 9B: No primary antibody control for lysed EVs. Grids containing this fraction were processed for immunocytochemistry, but the dArc1 primary antibody was omitted. No 10 nm gold granules are observed.

Figure 10:
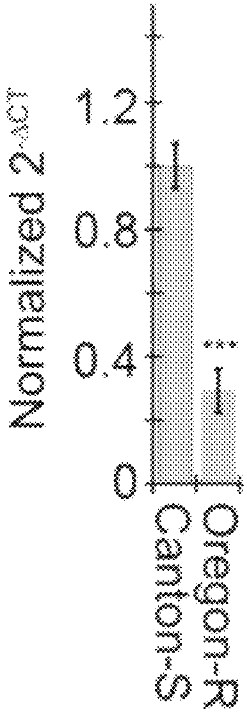

FIG. 10 presents exemplary data showing dArc1 transcript levels in Canton-S vs Oregon-R. qRT-PCR results from body wall preparations from the indicated genotypes. N (biological replicates; from left to right)=10,9; Graphs represent mean, and error bars SEM; statistical analysis was performed using a Student t-test; *=$p<0.05$; =$p<0.001$; **=$p<0.0001$.

Figures 11A, 11B, 11C, 11D, 11E, 11F, 11G, 11H:
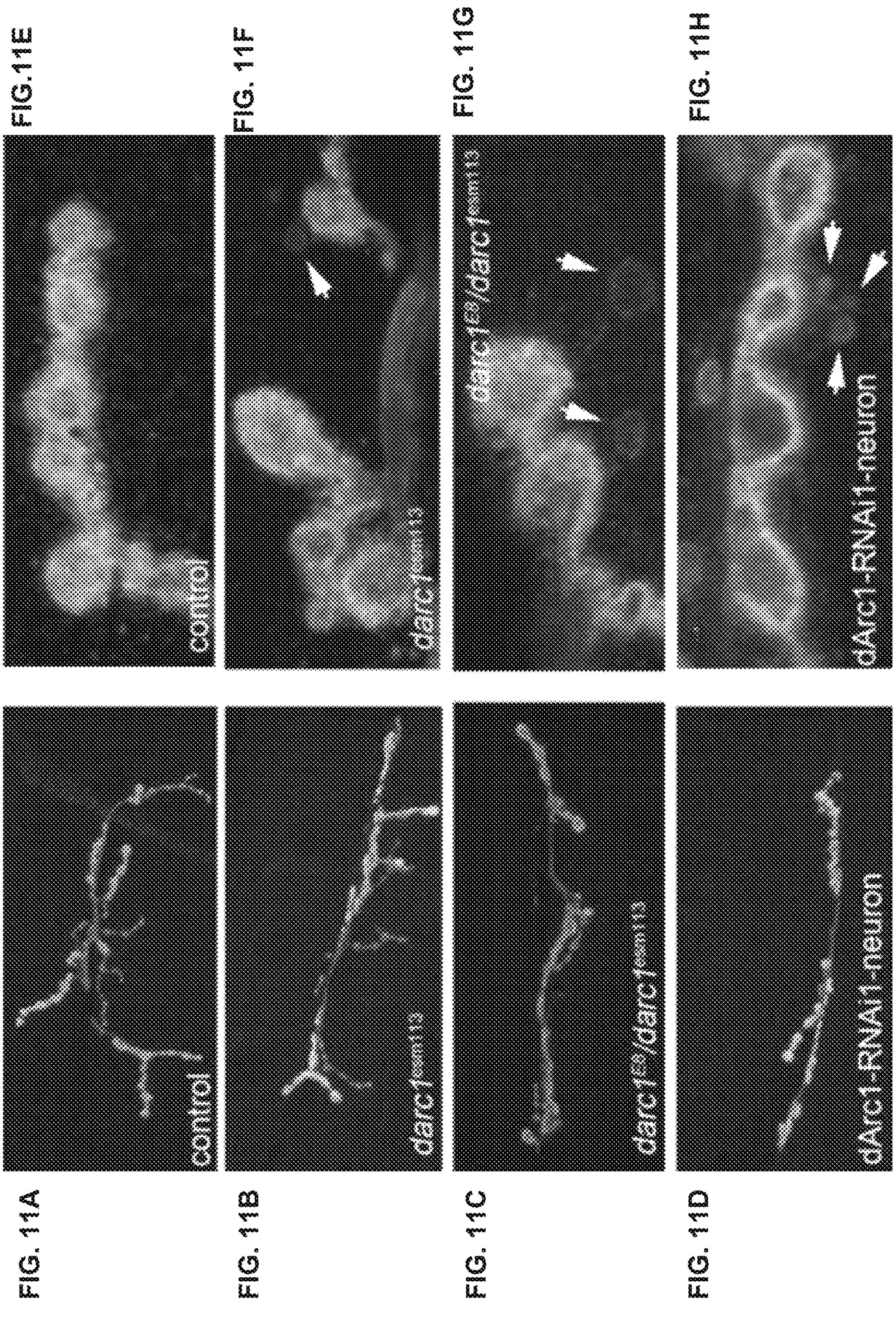
Figure 11I:
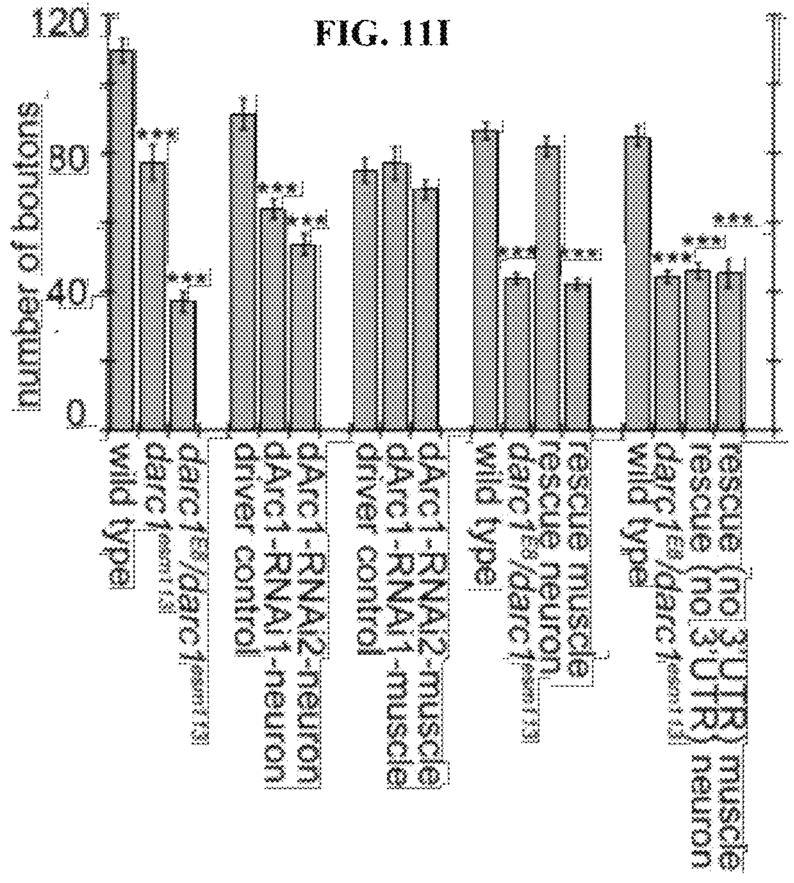
Figure 11O:
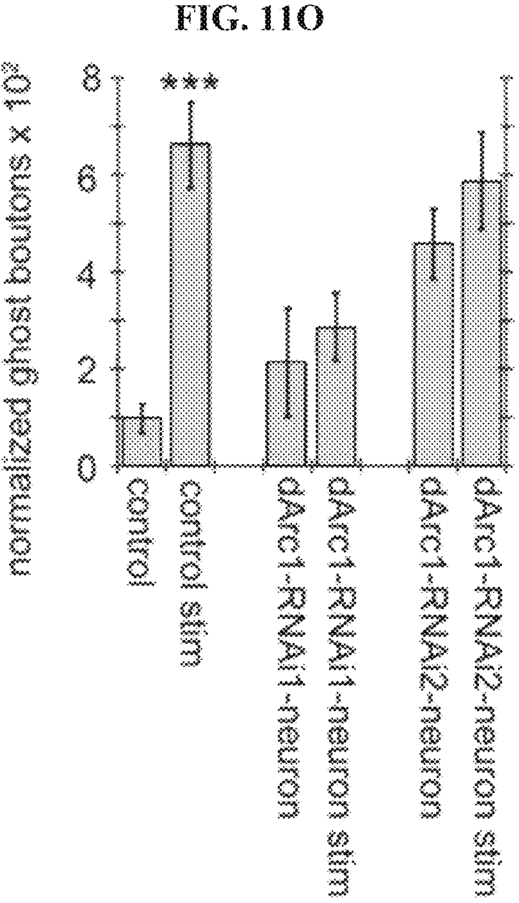

FIGS. 11A-11O present exemplary data showing that dArc1 influences developmental and activity-dependent plasticity at the NMJ.

FIGS. 11A-11D: Merged confocal Z-stacks of NMJ arbors labeled with antibodies against HRP and DLG in (A) C380-Gal4/+control, (B) darc1esm113 mutant, (C) darc1E8/darc1esm113 mutant, and (D) motorneuron expression of dArc1-RNAi1.

FIGS. 11E-11H: High magnification view of single confocal slices through NMJ branches in the same genotypes as (A-D).

FIGS. 11I, 11J and 11O: Quantification of third instar larval (I) synaptic boutons, (J) ghost boutons, and (O) activity induced ghost boutons in the indicated genotypes and conditions.

FIGS. 11K-11M: Single confocal slices of NMJs in preparations with antibodies against HRP and DLG in (K,L) unstimulated NMJs and (MN) after stimulating NMJs with a spaced stimulation protocol in the indicated genotypes.

Calibration bar is 46 μm in A-H and 6 μm in K-N; N=(from left to right; animals/arbors) I,J(14/27, 8/15, 6/12, 6/12, 6/10, 6/12, 12/21, 6/12, 6/12, 12/21, 8/16, 6/10, 6/10, 14/27, 10/20, 9/16, 6/10), O(12/19, 12/22, 6/12, 6/11, 7/14, 7/12). Data are represented as mean and error bars represent SEM. Statistical analysis was conducted using one-way ANOVA with Tukey post hoc test for I,J and Student's t-test for O. *=$p<0.05$; =$p<0.001$; *=$p<0.0001$.

Figure 12A:
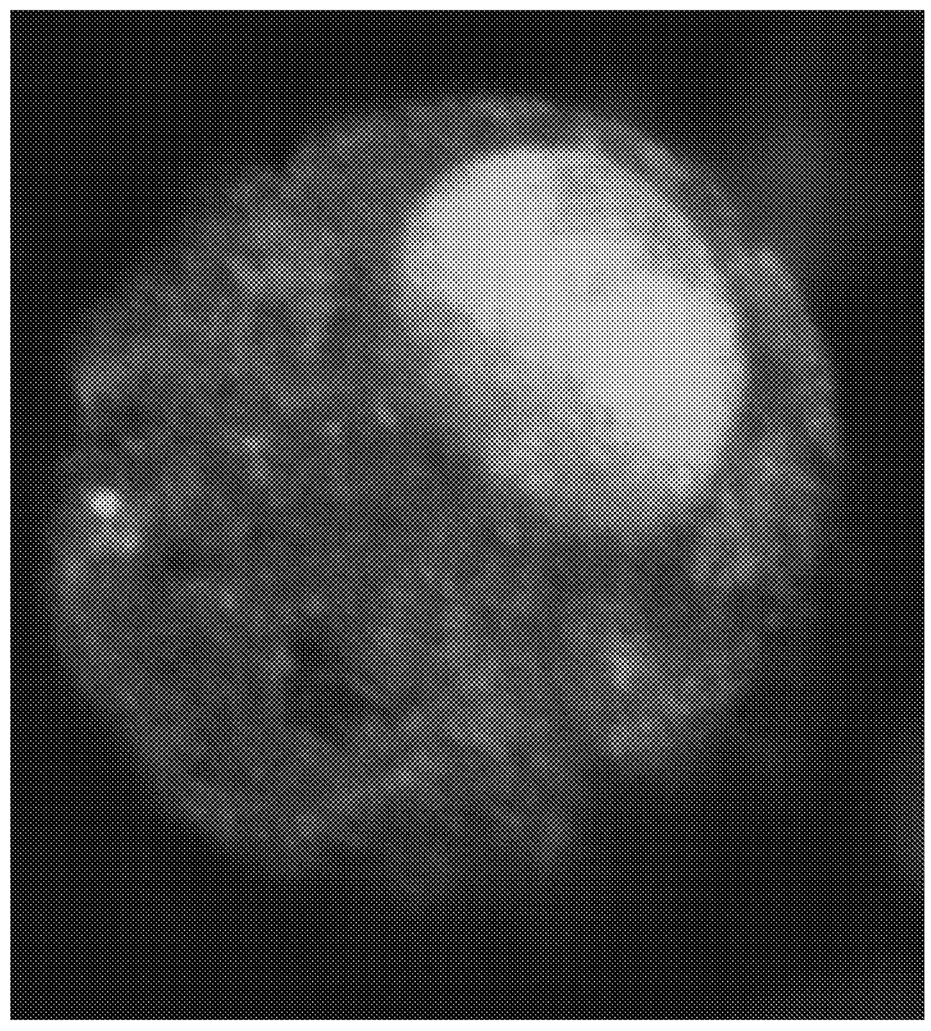
Figure 12B:
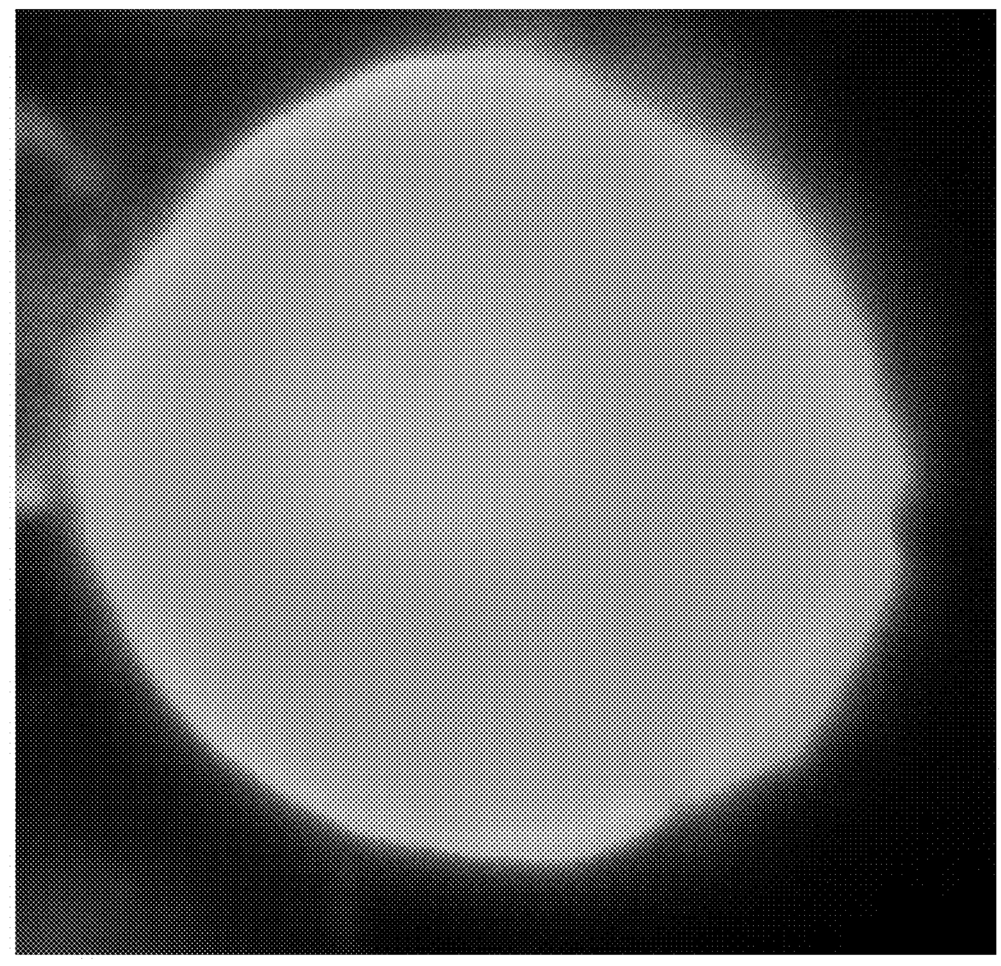

FIGS. 12A and 12B present exemplary photomicrographs in accordance with Example VIII showing differential GFP intensity in plasmid expression of a pAGW negative control (A) and an arc 3'UTR (B).

Figure 13A:
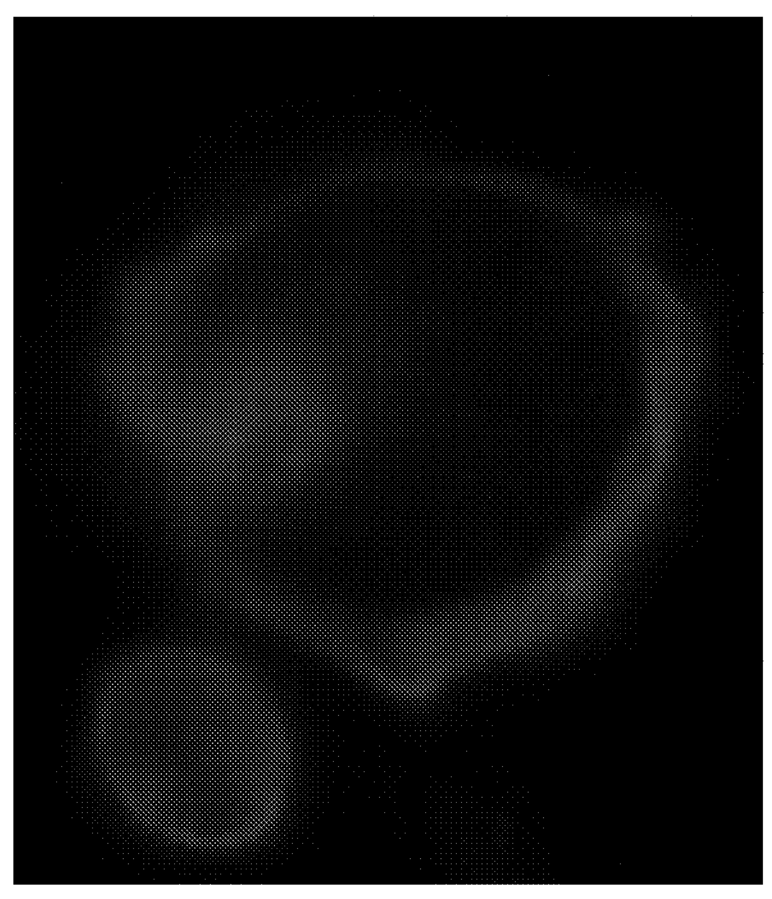
Figure 13B:
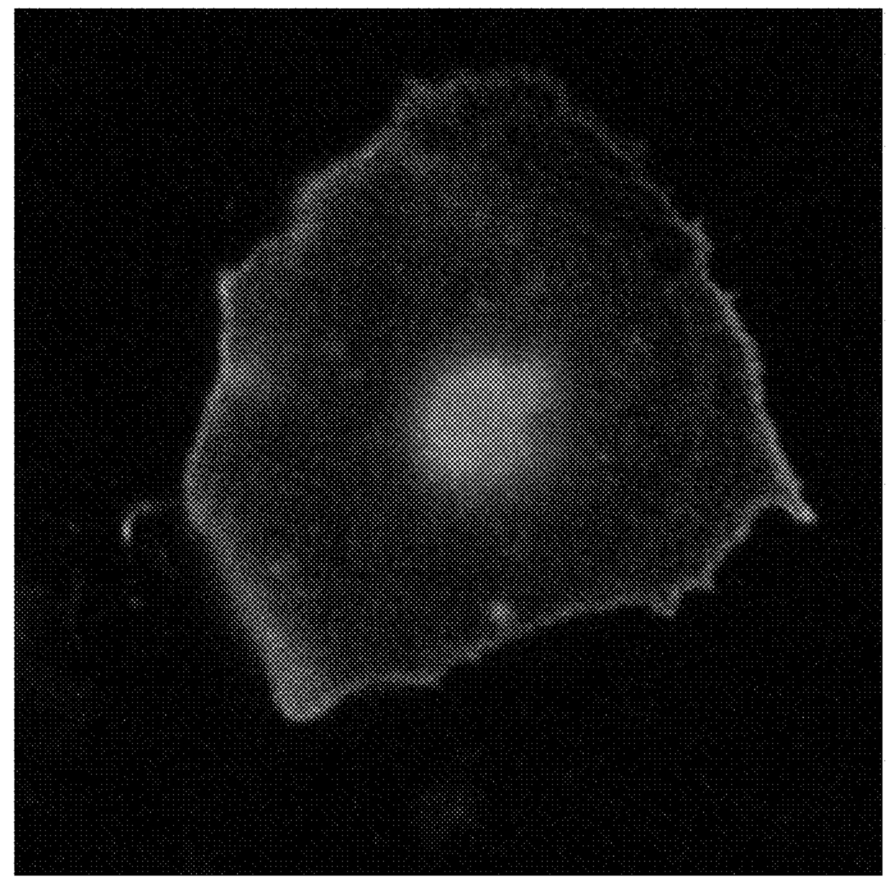

FIGS. 13A and 13B present exemplary photomicrographs in accordance with Example XXI showing putative exosome transfer into cells subsequent to arc 3'UTR expression (A) and not with the negative control pAGW gene expression product.

DETAILED DESCRIPTION OF THE INVENTION

The present invention is related to the field of therapeutic delivery platforms. Such therapeutic delivery platforms are based upon the formation of proteinacous exovesicles that bind nucleic acid payloads (e.g., mRNA, siRNA, shRNA etc.). These nucleic acid payloads may bind to the proteinacous vesicle either directly or as an adduct of a linker molecule. As one example, the linker molecule may be an arc 3' UTR that is bound to an Arc protein exovesicle.

In one embodiment, the present invention contemplates a therapeutic mRNA comprising an Arc mRNA 3' UTR sequence. In one embodiment, the Arc mRNA 3' UTR sequence binds to an Arc protein to create a chimeric mRNA/Arc protein. In one embodiment, the chimeric mRNA/Arc protein forms an exovesicle.

In one embodiment, the present invention contemplates a method comprising: i) a cell expressing an Arc protein in the presence of a therapeutic mRNA; ii) binding the Arc protein and therapeutic mRNA to form a chimeric mRNA/Arc protein exovesicle; iii) secreting the chimeric mRNA/Arc protein exovesicles. In one embodiment, the Arc/chimeric mRNA vesicles undergoes a cell type-specific transduction of the chimeric mRNA.

In one embodiment, the present invention contemplates a method comprising: i) a eukaryotic or prokaryotic heterologous cell culture system expressing an Arc protein; ii) purifying the Arc protein; and iii) incubating said purified Arc protein with in vitro-produced chimeric mRNA to form exovesicles.

In one embodiment, the present invention contemplates a method for treating a disease comprising administering an Arc protein/therapeutic mRNA chimeric complexes.

In some embodiments, the present invention contemplates trans-synaptic communication comprising biological compounds having properties resembling retroviruses and retrotransposons. In one embodiment, the trans-synaptic transport of a Gag-related endogenous protein, dArc1, and its mRNA is contemplated. For example, dArc1 protein binds to the 3'UTR of a darc1 mRNA transcript, and is extravesicularly transported from presynaptic boutons to the postsynaptic region of the NMJ. Although it is not necessary to understand the mechanism of an invention, it is believed that such intraneuronal communication is required for proper synapse maturation during development and for activity-dependent synapse formation. The data presented herein demonstrate that both Gag protein and RNA sequences from the retrotransposon Copia are loaded into EVs and released by cells, indicating either the domestication of viral mechanisms to shuttle material across cells, or the co-option of an endogenous cellular mechanism (e.g., for example, as for viral infection).

Multiple lines of evidence support the idea that dArc1 uses certain retroviral-like mechanisms to transfer a signal from the presynaptic compartment to the postsynaptic site required for NMJ expansion during development and for acute activity-dependent synaptic plasticity, much like a viral capsid binds its own transcript. It is demonstrated herein that dArc1 protein binds darc1 mRNA, specifically its 3'UTR. Like retroviruses, darc1 RNA and protein are transmitted from cell to cell by trans-synaptic transfer of wild type dArc1 protein and mRNA. This transfer appears to be unidirectional, as postsynaptic muscle darc1 mRNA and dArc1 protein levels were decreased when expressing dArc1-RNAi in neurons but not in muscles. The inability of dArc1-RNAi to downregulate darc1 mRNA might be due to darc1 RNA at the postsynaptic region being inaccessible to the RNAi machinery (e.g. D2 bodies. Nishida et al., "Roles of R2D2, a cytoplasmic D2 body component, in the endogenous siRNA pathway in *Drosophila*" *Mol Cell* 49:680-691 (2013).

The data presented herein utilize a UAS/Gal4 system to express dArc1-RNAi, which is conventionally believed to require transcription and export from the nucleus. In contrast, present data suggest that postsynaptic darc1 mRNA and protein are derived from the presynaptic neuron, which likely determines their postsynaptic localization. Indeed, expressing a dArc1 transgene in muscle did not result in synaptic localization of the transgenic protein. Moreover, expressing a transfer-incompetent dArc1 transgene in neurons abrogated most of the postsynaptic darc1 RNA and protein. Another possibility that could explain the postsynaptic RNAi insensitivity is the ability of Arc protein to multimerize thereby forming a capsid which is likely to protect dArc1 RNA. Myrum et al., "Arc is a flexible modular protein capable of reversible self-oligomerization" *Biochem J* 468:145-158 (2015). If this is the case, it would be important, in the future, to determine how/whether dare mRNA exits the capsid to locally function at postsynaptic sites.

Support for a model that dArc1 might take advantage of viral properties for transsynaptic signaling is derived from observations with an endogenous retrotransposon common in flies (e.g., Copia). Retrotransposons like Copia contain an entire set of genes present in the retroviral genome, except for envelope genes. Nefedova et al., "Mechanisms of LTR-Retroelement Transposition: Lessons from *Drosophila melanogaster*" *Viruses* 9 (2017). Thus, unlike retroviruses, retrotrasnposons are thought not to be transferred between cells. The data shown herein demonstrate that both copia RNA and Copia protein were released from cells via EVs. Copia's presence in EVs possibly allows them to spread to neighboring cells. Strikingly, the Gag-encoding truncated region of copia RNA and protein were the predominant forms in S2 EVs. This short form does not encode the proteins necessary for Copia replication and integration into the genome. This raises the possibility that Gag-like domains might have been adopted by multicellular organisms during evolution for cell-to-cell communication. Multiple genes, like darc1 and copia$^{S}$, containing a Gag region have been identified in genomes. Campillos et al., "Computational characterization of multiple Gag-like human proteins" *Trends Genet* 22:585-589 (2006). These other genes may also have an ability to transport RNAs from cell to cell. While it remains to be determined whether Copias is actually transferred from cell to cell, it would be interesting to consider whether transposable element fragments have a physiological role in cell communication. Transposable element fragments comprise most or the human and fly genome, and although alleged being part of the "junk DNA", such a physiological role would explain why they have been maintained throughout evolution.

The ORF of mammalian Arc and darc1 are largely comprised of regions derived of viral-like Gag sequences, likely the remnants of an earlier transposon insertion, and previous work showed that the Gag region of Arc can fold like a viral capsid. Zhang et al., "Structural basis of arc binding to synaptic proteins: implications for cognitive disease" *Neuron* 86:490-500 (2015). There are over 30 other proteins in *Drosophila* that have significant portions of their coding region comprised of Gag like sequences. Abrusan et al., "Turning gold into 'junk': transposable elements utilize central proteins of cellular networks" *Nucleic Acids Res* 41:3190-3200 (2013). Both the fly and mammalian genomes contain a large proportion (~40%) of transposable elements, so far referred to as "junk DNA". Lander et al., "Initial sequencing and analysis of the human genome" *Nature* 409:860-921 (2001).

These results raise the provocative idea that other Gag-related proteins and Gag-containing transposons might have a physiological function in cell-cell communications. This would explain the retention of retrotransposons through evolution. In addition, it is possible that the Gag containing proteins encoded in the fly genome could represent the serendipitous integration of a retrotransposon into a functional gene, similarly to how dArc1 was likely created. Future studies geared to understanding the function of these Gag proteins as well as Gag-encoding transposons or transposon fragments will be needed to address these possibilities.

Alternatively, it could represent the serendipitous integration of a retrotransposon into a functional gene, similar to how dArc1 was likely created. Taken together, the present findings show that darc1 RNA and protein can be transferred from presynaptic terminals to postsynaptic sites, and previous results report that increased presynaptic electrical activity enhances exosome-like EV release. Ataman et al., "Rapid activity-dependent modifications in synaptic structure and function require bidirectional wnt signaling" *Neuron* 57:705-718 (2008); Faure et al., "Exosomes are released by cultured cortical neurones" *Mol Cell Neurosci* 31:642-648 (2006); Frühbeis et al., "Emerging Roles of Exosomes in Neuron-Glia Communication" *Front Physiol* 3 (2012); and Fruhbeis et al., "Neurotransmitter-triggered transfer of exosomes mediates oligodendrocyte-neuron communication" *PLoS Biol* I1:e1001604 (2013). These data open the possibility that dArc1 might be delivered to postsynaptic sites in an activity-dependent fashion. This would allow localization of synaptic modifications to specific synaptic sites. Indeed, at the larval NMJ, individual synaptic boutons show functional specialization, releasing neurotransmitter in either an evoked or spontaneous fashion. Peled et al., "Evoked and spontaneous transmission favored by distinct sets of synapses" *Curr Biol* 24:484-493 (2014).

The strength of synaptic transmission is believed to be consistent within a single bouton and increases in a gradient along the arbor which can have implications for synapse formation. Guerrero et al., "Heterogeneity in synaptic transmission along a *Drosophila* larval motor axon" *Nat Neurosci* 8:1188-1196 (2005). A sequestration of material at selective synaptic boutons is also seen during the recycling of peptidergic vesicles, which must be synthesized in the neuronal soma, but released far away at active synaptic boutons. This appears to be resolved by a continuous transit of peptidergic vesicles through inactive synaptic boutons, and their capture by active ones. Shakiryanova et al., "Activity-dependent synaptic capture of transiting peptidergic vesicles" *Nat Neurosci* 9:896-900 (2006). While synapse specificity is also observed during plasticity in mammalian systems, Arc has been reported to localize exclusively in dendrites, and not at presynaptic sites. Lyford et al., "Arc, a growth factor and activity-regulated gene, encodes a novel cytoskeleton-associated protein that is enriched in neuronal dendrites" *Neuron* 14:433-445 (1995). However, mammalian Arc is believed to be present in EVs, raising the possibility of dendrite-to-dendrite vesicular communication.

*Drosophila* Arc1 and Arc2 appear to result from a genomic duplication event and are solely composed of a Gypsy transposon-derived Gag domain. While the QRF of darc1 and darc2 are highly conserved, they differ vastly in their 3'UTR. The data presented herein show that the 3'UTR of darc1 mRNA is necessary and sufficient for the transport and accumulation of darc1 postsynaptically. This suggests that the 3'UTR of darc1 imparts some function needed to load darc1 mRNAs into EVs. In this regard, it's interesting to note that the dArc2 protein, but not its mRNA, which lacks a long 3'UTR, is enriched in EVs. These data suggest that darc1 mRNA may play a role in EV RNA loading in vivo. The rat Arc 3'UTR contains Gypsy-like sequences, transposon sequences similar to those of darc1. Since these genes most likely evolved independently the similarity of the mammalian and fly Arc proteins and mRNAs indicates the possibility of convergent evolution of this mechanism of trans-cellular communication.

I. Exosomal Trans-Cellular Communication

Exosomes are cell-derived vesicles that are present in many and perhaps all eukaryotic fluids, including but not limited to blood, urine, and cultured medium of cell cultures. A sub-type of exosomes, defined as Matrix-bound nanovesicles (MBVs), was reported to be present in extracellular matrix (ECM) bioscaffolds (non-fluid). van der Pol et al., "Classification, functions, and clinical relevance of extracellular vesicles" *Pharmacol. Rev.* 64(3):676-705 (2012); Keller et al., "Exosomes: from biogenesis and secretion to biological function" *Immunol. Let.* 107(2):102-108 (2006); and Huleihel et al., "Matrix-bound nanovesicles within ECM bioscaffolds" *Science Advances* 2(6):e1600502 (2016).

The reported diameter of exosomes is between 30 and 100 nm, which is larger than low-density lipoproteins (LDL) but much smaller than, for example, red blood cells. Exosomes are either released from the cell when multivesicular bodies fuse with the plasma membrane or released directly from the plasma membrane. Evidence is accumulating that exosomes have specialized functions and play a key role in processes such as coagulation, intercellular signaling, and waste management. Consequently, there is a growing interest in the clinical applications of exosomes. Exosomes can potentially be used for prognosis, for therapy, and as biomarkers for health and disease. Booth et al., "Exosomes and HIV Gag bud from endosome-like domains of the T cell plasma membrane" *J. Cell Biol.* 172(6):932-935 (2006).

In most mammalian cells, portions of the plasma membrane are regularly internalized as endosomes, with 50 to 180% of the plasma membrane being recycled every hour. In turn, parts of the membranes of some endosomes are subsequently internalized as smaller vesicles. Such endosomes are called multivesicular bodies because of their appearance, with many small vesicles, or "intralumenal endosomal vesicles," inside the larger body. The intralumenal endosomal vesicles become exosomes if the multivesicular body merges with the cell membrane, releasing the internal vesicles into the extracellular space. Huotari et al., "Endosome maturation" *The EMBO Journal.* 30(17):3481-3500 (2011); and Gruenberg et al., "Mechanisms of pathogen entry through the endosomal compartments" *Nature Reviews* 7(7):495-504 (2006).

Exosomes contain various molecular constituents of their cell of origin, including but not limited to proteins and/or RNA. Although the exosomal protein composition varies with the cell and tissue of origin, most exosomes contain an evolutionarily-conserved common set of protein molecules. The protein content of a single exosome, given certain assumptions of protein size and configuration, and packing parameters, can be about 20,000 molecules. mRNA and miRNA has been reported as cargo in exosomes. Exosomes have also been shown to carry double-stranded DNA. Maguire, G., "Exosomes: smart nanospheres for drug delivery naturally produced by stem cells" *In: Fabrication and Self Assembly of Nanobiomaterials*. Elsevier pp. 179-209 (2016); Valadi et al., "Exosome-mediated transfer of mRNAs and microRNAs is a novel mechanism of genetic exchange between cells" *Nat. Cell Biol.* 9(6): 654-659 (2007); and Thakur et al., "Double-stranded DNA in exosomes: a novel biomarker in cancer detection" *Cell Research* 24(6):766-769 (2014).

Exosomes can transfer molecules from one cell to another via membrane vesicle trafficking, thereby influencing the immune system, such as dendritic cells and B cells, and may play a functional role in mediating adaptive immune responses to pathogens and tumors. Li et al., "Role of exosomes in immune regulation" *J. Cell. Mol. Med.* 10(2): 364-375 (2006). Therefore, exosomes may play a role in cell-to-cell signaling and deliver cargo RNA molecules. For example, mRNA in exosomes has been suggested to affect protein production in the recipient cell. Balaj et al., "Tumour microvesicles contain retrotransposon elements and amplified oncogene sequences" *Nature Communications* 2(2):180 (2011). However, another study has suggested that miRNAs in exosomes secreted by mesenchymal stem cells (MSC) are predominantly pre- and not mature miRNAs. Chen et al., "Mesenchymal stem cell secretes microparticles enriched in pre-microRNAs" *Nucleic Acids Res.* 38(1):215-224 (2010). Because this study did not report any RNA-induced silencing complex-associated proteins in these exosomes, it was concluded that only the pre-miRNAs but not the mature miRNAs in MSC exosomes have the potential to be biologically active in the recipient cells.

Exosomes may play in cell-to-cell signaling because exosomes can merge with and release their contents into cells that are distant from their cell of origin (e.g., membrane vesicle trafficking) and influence processes in the recipient cell. For example, RNA that is shuttled from one cell to another, known as "exosomal shuttle RNA," could potentially affect protein production in the recipient cell. Balaj et al., "Tumour microvesicles contain retrotransposon elements and amplified oncogene sequences" *Nature Communications* 2(2):180 (2011); and Valadi et al., "Exosome-mediated transfer of mRNAs and microRNAs is a novel mechanism of genetic exchange between cells" *Nat. Cell Biol.* 9(6): 654-459 ((2007). By transferring molecules from one cell to another, exosomes from certain cells of the immune system, such as dendritic cells and B cells, may play a functional role in mediating adaptive immune responses to pathogens and tumors. Li et al., "Role of exosomes in immune regulation" *J. Cell. Mol. Med.* 10(2):364-375 ((2006).

Exosomes may have potential therapeutics application as reports suggest an ability to elicit potent cellular responses in vitro and in vivo. Han et al., "Exosomes and Their Therapeutic Potentials of Stem Cells" *Stem Cells International.* 2016:7653489 (2016); Yeo et al., "Exosomes and their Therapeutic Applications" In: *Advances In Pharmaceutical Cell Therapy: Principles of Cell-Based Blopharmaceuticals* pp. 477-501 (2016); and Di Rocco et al., "Towards Therapeutic Delivery of Extracellular Vesicles: Strategies for In Vivo Tracking and Biodistribution Analysis" *Stem Cells International.* 2016:5029619 (2016). Exosomes have been reported to mediate regenerative outcomes in injury and disease that recapitulate observed bioactivity of stem cell populations. Basu et al., "Exosomes for repair, regeneration and rejuvenation" *Expert Opinion on Biological Therapy* 16(4):489-506 (2016). Exosomes may induce the expression of a number of growth factors (hepatocyte growth factor (HGF), insulin-like growth factor-1 (IGF1), nerve growth factor (NGF), and stromal-derived growth factor-1 (SDF1)). Shabbir et al., "Mesenchymal Stem Cell Exosomes Induce Proliferation and Migration of Nonnal and Chronic Wound Fibroblasts, and Enhance Angiogenesis In Vitro" *Stem Cells And Development* 24(14):1635-1647 (2015).

Exosomes secreted by human circulating fibrocytes, a population of mesenchymal progenitors involved in normal wound healing via paracrine signaling, exhibited in-vitro proangiogenic properties, activated diabetic dermal fibroblasts, induced the migration and proliferation of diabetic keratinocytes, and accelerated wound closure in diabetic mice in vivo. Components of the exosomal cargo were heat shock protein-90a, total and activated signal transducer and activator of transcription 3, proangiogenic (miR-126, miR-130a, miR-132) and anti-inflammatory (miR124a, miR-125b) microRNAs, and a microRNA regulating collagen deposition (miR-21). Geiger et al., "Human fibrocyte-derived exosomes accelerate wound healing in genetically diabetic mice" *Biochemical and Biophysical Research Communications* 467(2):303-309 (2015).

Exosomes and other extracellular vesicles (EVs), such as microvesicles, have recently emerged as a putative transcellular communication strategy in the healthy and diseased brain. Basso et al., "Extracellular Vesicles and a Novel Form of Communication in the Brain" *Front Neurosci* 10:127 (2016). For instance, glutamate release by neurons induces oligodendroglial secretion of exosomes, which are taken up by recipient neurons and regulate their physiology. Fruhbeis et al., "Neurotransmitter-triggered transfer of exosomes mediates oligodendrocyte-neuron communication" *PLoS Biol* 11, e1001604 (2013). At the *Drosophila* neuromuscular synapses, Wnt signaling is mediated by trans-synaptic transfer of the Wnt, Wingless, via exosomes in vivo. Koles et al., "Mechanism of evenness interrupted (evi)-exosome release at synaptic boutons" *J Biol Chem* 287:16820-16834 (2012; and Korkut et al., "Trans-synaptic transmission of vesicular Wnt signals through Evi/Wntless" *Cell* 139:393-404 (2009). In mammals, the propagation of neurodegenerative disorders, such as ALS, appears to be partly mediated by the transfer of prion-like proteins across cells via exosomes. Basso et al., "Extracellular Vesicles and a Novel Form of Communication in the Brain" *Front Neurosci* 10:127 (2016).

Exosomes can be considered a possible carrier for effective delivery of small interfering RNA due to their existence in body's endogenous system. Wahlgren et al., "Delivery of Small Interfering RNAs to Cells via Exosomes" *SiRNA Delivery Methods: Methods and Protocols. Methods in Molecular Biology* 1364:105-125 (2016); and Kumar et al., "Exosomes: natural carriers for siRNA delivery" *Current Pharmaceutical Design* 21(31):4556-4565 (2015). Patient-derived exosomes have been employed as a novel cancer immunotherapy in several clinical trials. Bell et al., "Designer exosomes as next-generation cancer immunotherapy" *Nanomedicine: Nanotechnology. Biology and Medicine* 12(1):163-169 (2016). Exosomes were also used as a vehicle for the delivery of cancer drug paclitaxel. Paclitaxel was incorporated inside exosomes derived from white blood cells, which were then injected into mice with drug-resistant lung cancer. Notably, exosomal delivery of paclitaxel increased cytotoxicity more than 50 times as a result of nearly complete co-localization of airway-delivered exosomes with lung cancer cells. Kim et al., "Development of exosome-encapsulated paclitaxel to overcome MDR in cancer cells" *Nanomedicine: Nanotechnology, Biology and Medicine* 12(3):655-664 (2016).

Exosomes offer distinct advantages that uniquely position them as highly effective drug carriers. Composed of cellular membranes with multiple adhesive proteins on their surface, exosomes are known to specialize in cell-cell communications and provide an exclusive approach for the delivery of various therapeutic agents to target cells. Batrakova et al., "Using exosomes, naturally-equipped nanocarriers, for drug delivery" *Journal of Controlled Release* 219:396-405 (2015).

II. Intraneuronal Arc Trafficking

Activity-Regulated Cytoskeleton (Arc) protein is an activity-dependent immediate early gene, and its mRNA is translocated to dendrites via sequences in its 3'-Untranslated Region (UTR). (Dynes et al., "Dynamics of bidirectional transport of Arc mRNA in neuronal dendrites" *J Comp Neurol* 500:433-447 (2007). As an evolutionarily conserved immediate-early neuronal gene, Arc, encodes a protein that binds Arc-mRNA via a 3' untranslated region (UTR). Subsequently, the Arc protein/Arc mRNA complex forms an exovesicle that can deliver the bound Arc mRNA for expression in recipient cells. One significant improvement of the present invention over the prior art is the lack of an elicited immune response that provides for the clinical use of a human Arc protein-mRNA exovesicle.

Following plasticity-inducing stimulation Arc mRNA moves into active dendritic spines, where it is translated and regulates trafficking of AMPA receptors by engaging the endocytic machinery. Chowdhury et al., "Arc/Arg3.1 interacts with the endocytic machinery to regulate AMPA receptor trafficking" *Neuron* 52:445-459 (2006). Arc is also involved in regulating dendritic spine morphology during plasticity. Peebles et al., "Arc regulates spine morphology and maintains network stability in vivo" *Proc Natl Acad Sci USA* 107:18173-18178 (2010).

Arc protein is composed of Group-specific antigen (Gag)-like amino acid sequences typically found in retroviruses such as HIV and in retrotransposons. Campillos et al., "Computational characterization of multiple Gag-like human proteins" *Trends Genet* 22:585-589 (2006). Beyond its binding to Tarpy2, an AMPA-receptor binding protein, the physiological significance of the Gag-like sequences in Arc is unknown. Zhang et al., "Structural basis of are binding to synaptic proteins: implications for cognitive disease" *Neuron* 86:490-500 (2015). During retroviral replication, Gag proteins multimerize into capsids, which bind and package viral RNA. Chen B., "HIV Capsid Assembly, Mechanism, and Structure" *Biochemistry* 55:2539-2552 (2016). Capsids then undergo secondary envelopment by membranes and exit the host cell being competent to infect other cells. Alenquer et al., "Exosome Biogenesis, Regulation, and Function in Viral Infection" *Viruses* 7:5066-5083 (2015). There is a growing aggregate of evidence that suggest some viruses commandeer host exosomal pathways suggesting a connection between viruses and exosomes. Meckes D., "Exosomal communication goes viral". *J Virol* 89:5200-5203 (2015).

Exovesicles from *Drosophila* cultured cells were found to contain an abundance of enriched mRNAs of the *Drosophila* Arc gene (darc1). Lefebvre et al., "Comparative transcriptomic analysis of human and *Drosophila* extracellular vesicles" *Sci Rep* 6:27680 (2016). Specifically, the synaptic boutons of larval neuromuscular junctions were enriched with darc1 mRNA and Arc protein were enriched at synaptic boutons and subsequently transferred to postsynaptic muscles, presumably by exovesicles. Notably, this cell-cell transfer was dependent on a gypsy retrotransposon-like sequence fragment in the darc1 3' UTR.

Evocative of retroviral Gags, dArc1 protein physically associated with darc1 mRNA. In support of this observation, a spliced fragment of the Copia retrotransposon mRNA and protein were also found within EVs. This retroviral-like mechanism of transfer is required for dArc1 protein function, as blocking the arc1 transfer resulted in aberrations in both synapse maturation and activity-dependent plasticity. Consequently, it appears that dArc1 influences synaptic plasticity by utilizing a retroviral-like mechanism for transport between synaptic cell types.

The ORF of darc1 is mostly represented by the remnant of a Gypsy-superfamily of transposons, specifically dArc1 has strong similarities to the GAG region of a Gypsy-like transposon. See, FIG. 2U. Although it is not necessary to understand the mechanism of an invention it is believed that EVs contain multiple enveloped capsid-like particles or a single capsid-like structure. It is further believed that these capsid-like particles are taken up by the postsynaptic muscle, either through EV fusion with the muscle membrane, or endocytosis and further fusion with the endosome membrane. For example, this transfer may serve to stimulate synaptic maturation, as downregulation of presynaptic dArc1 leads to accumulation of ghost boutons.

Figures 1A, 1B, 1C, 1D:
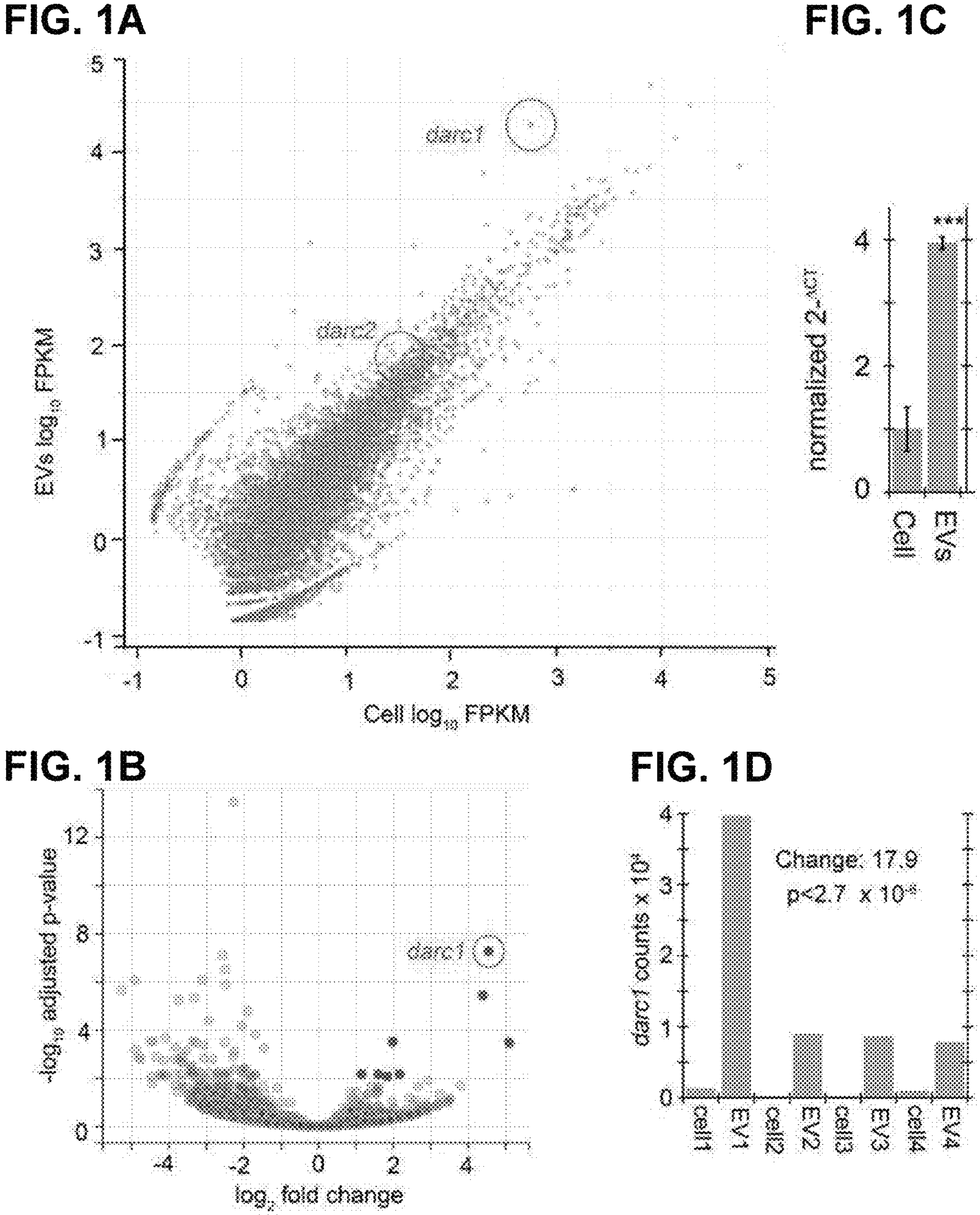
FIGS. 1A-D present exemplary data showing darc1 mRNA is enriched in exosomes.
Figures 2A, 2B, 2C, 2D:
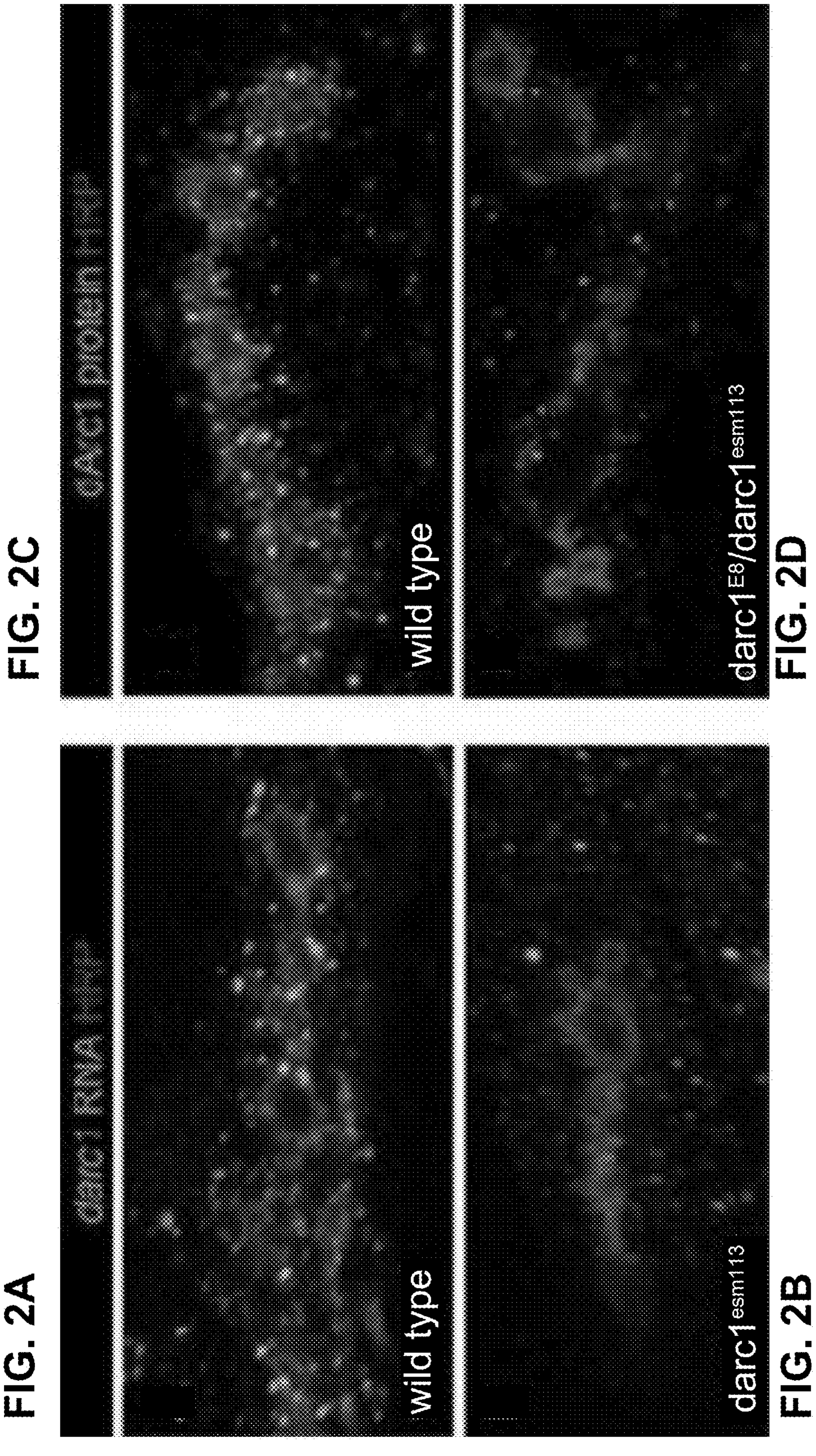
FIGS. 2A-D present exemplary data of confocal slices of NMJ branches in preparations double labeled with anti-HRP.
Figures 2E, 2F, 2G, 2H:
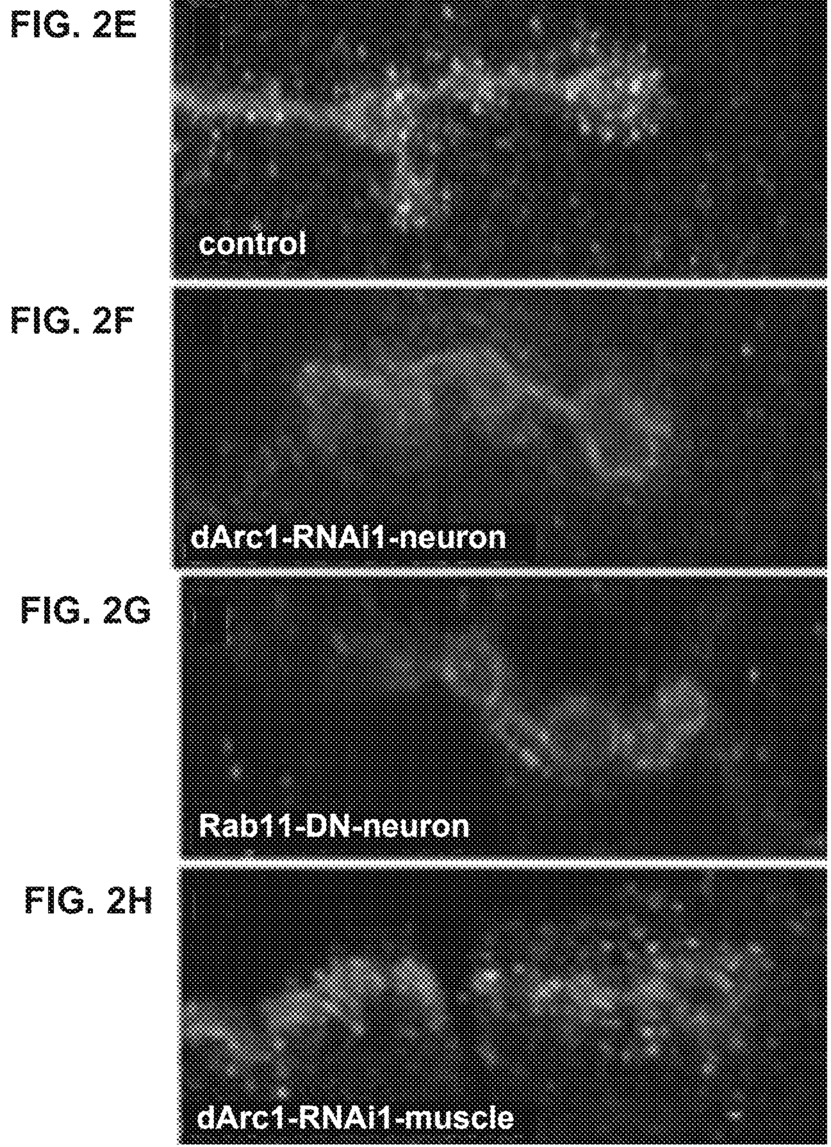
FIGS. 2E-2L: Confocal slices of NMJ branches in preparations double labeled with anti-HRP and either (E-H) a darc1 FISH probe, or (I-L) anti-dArc1, in (E,I) C380-Gal4/+ control, upon expression of (F,J) dArc1-RNAi in motorneurons, (G,K) Rab11-DN in motorneurons, and (H,L) dArc1-RNAi in muscles.
Figures 2I, 2J, 2K, 2L:
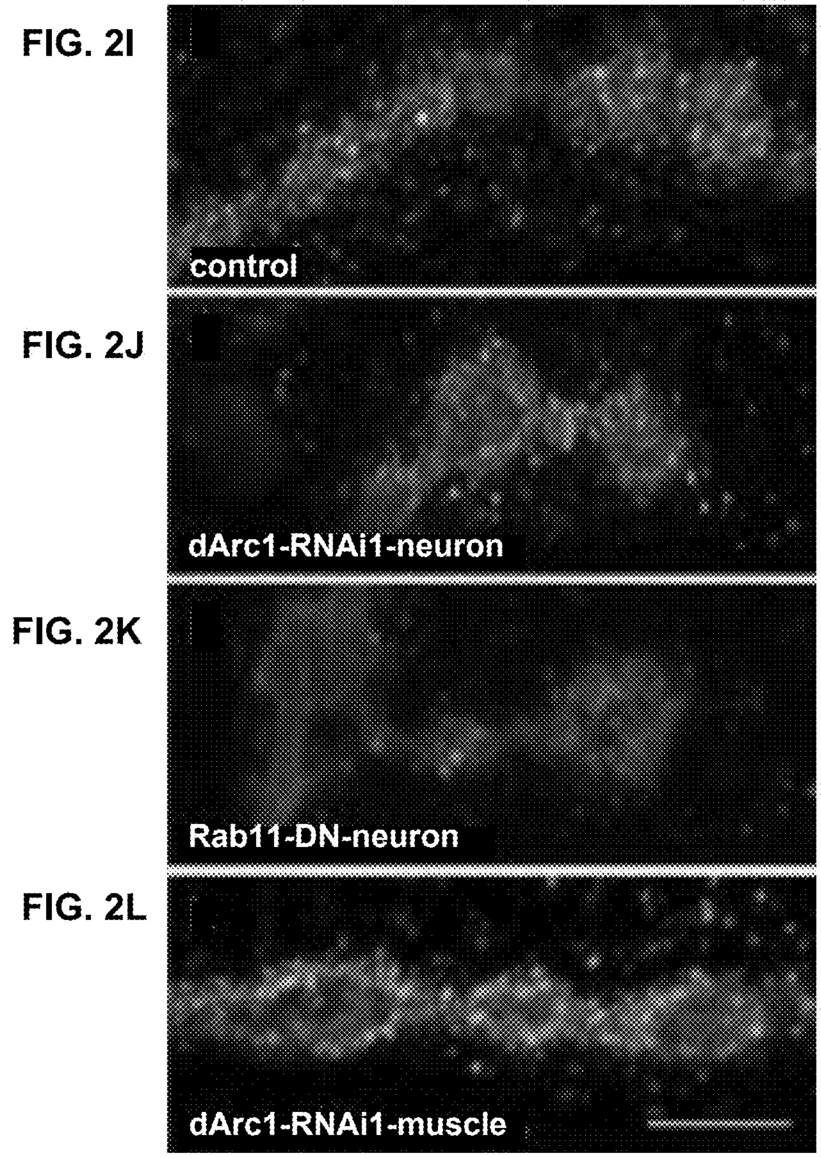
Figure 2N:
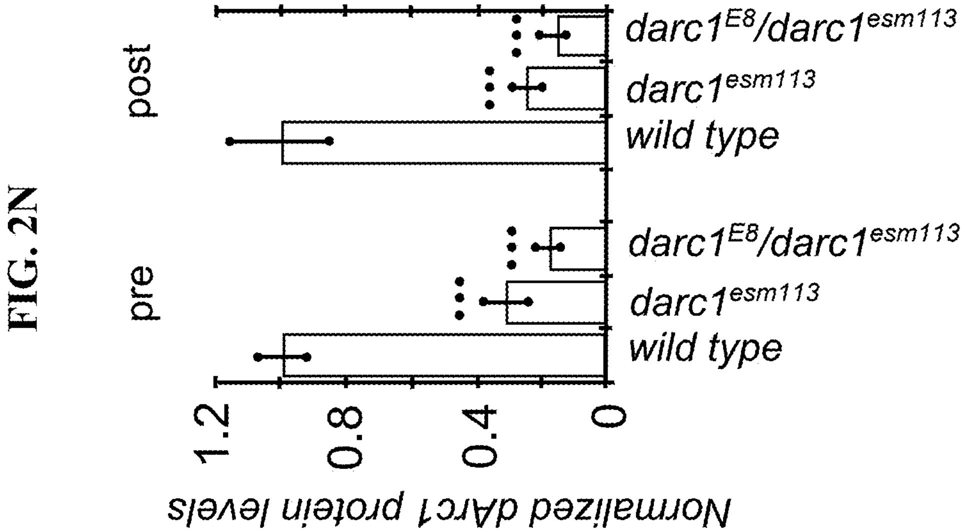
FIG. 2M-2R: Quantification of (M,O,Q) darc1 FISH signal and (N,P,R) dArc1 immunocytochemical signal at the NMJ in the indicated genotypes.
Figure 2M:
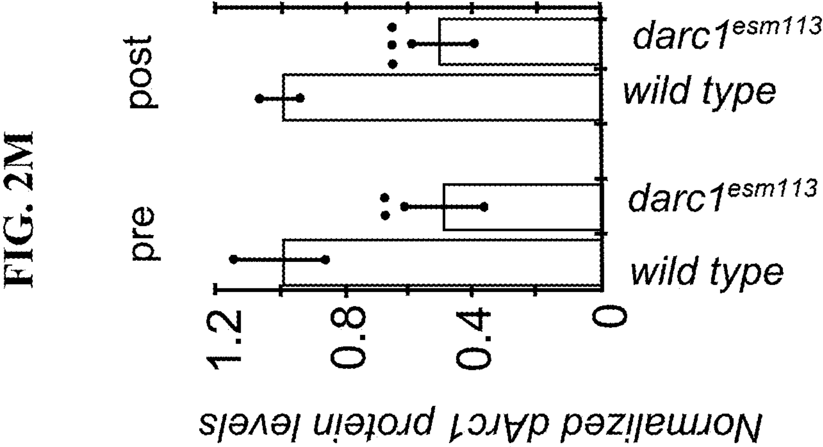
Figure 2P:
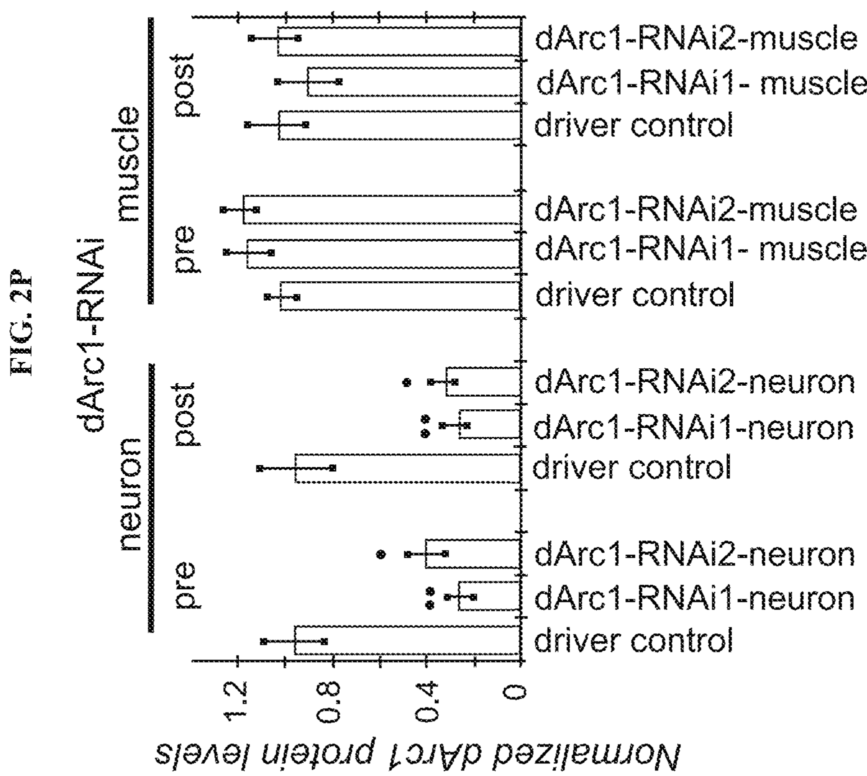
Figure 2O:
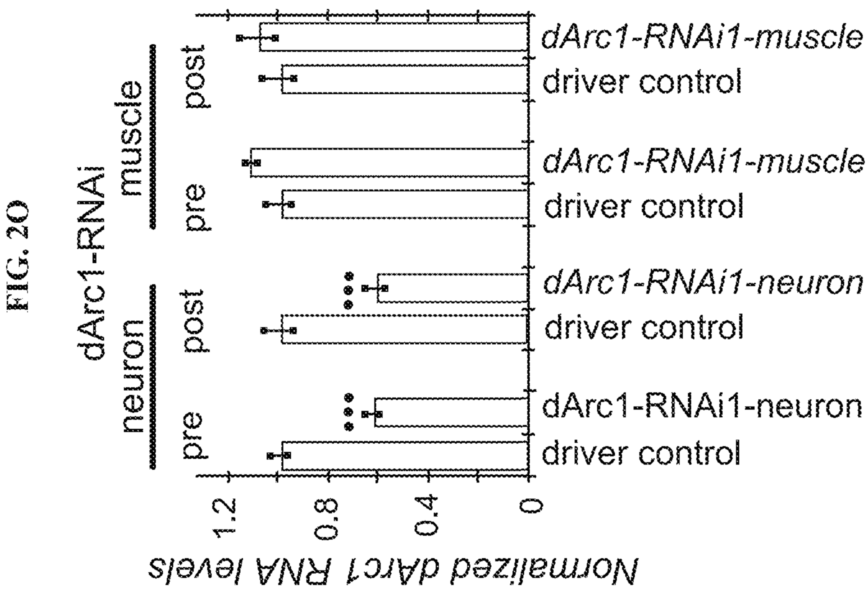
Figure 2Q:
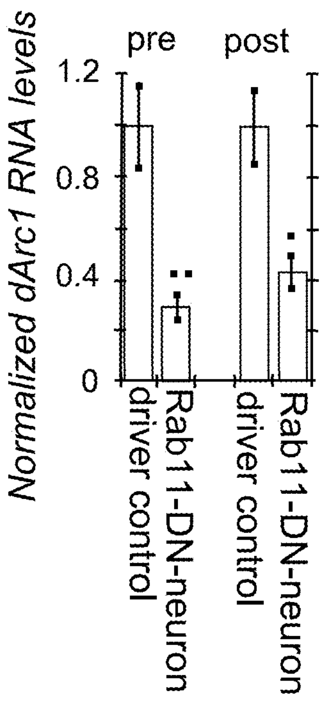
Figure 2R:
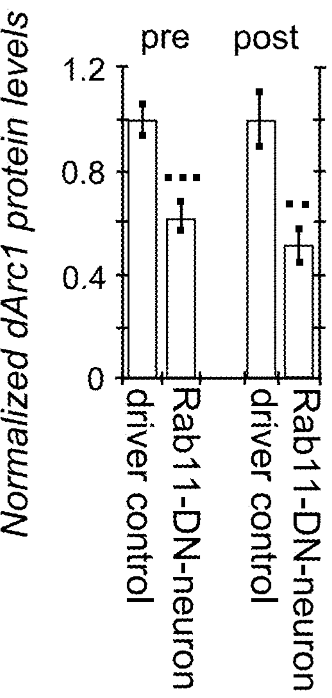

The presence of darc1 in EVs together with the observation that darc1 encodes a retroviral Gag-like protein raised the possibility that the mRNA, similar to retroviral genomic RNA (gRNA), could be transferred across synaptic partners, as previously shown for two transmembrane proteins, Evi and Syt4. Korkut et al., "Trans-synaptic transmission of vesicular Wnt signals through Evi/Wntless" *Cell* 139: 393404 (2009); and Korkut et al., "Regulation of postsynaptic retrograde signaling by presynaptic exosome release" *Neuron* 77:1039-1039 (2013). To test this possibility, darc1 was exclusively downregulated in motorneurons, using the Gal4 driver C380-Gal4 to express UAS-dArc1-RNAi, and the pre- and postsynaptic levels of dArc1 mRNA via FISH was examined. Expressing dArc1-RNAi in motorneurons resulted in a significant decrease in darc1 FISH signal, not only at presynaptic boutons, but also at the muscle postsynaptic region. FIGS. 2E, 2F and 2O. The C380-Gal4 driver does not express Gal4 in muscles and transfer of RNAi between NMJ synaptic partners has not been previously observed. (e.g., (Budnik et al., 1996)-(Ataman et al., 2006)). Although it is not necessary to understand the mechanism of an invention it is believed that postsynaptic darc1 mRNA is derived from a presynaptic pool, presumably via EVs. Similarly, to the FISH results, expressing dArc1-RNAi in motorneurons resulted in a significant decrease in dArc1 protein immunoreactive signal, both in pre- and postsynaptic compartments. FIGS. 2I, 2J, and 2P; and FIG. 3B.

In contrast, expressing dArc1-RNAi with a muscle Gal4 driver, C57-Gal4, did not affect dArc1 RNA nor dArc1 protein levels. FIGS. 2H, 2L, 2O, and 2P; and FIG. 3B. Although it is not necessary to understand the mechanism of an invention it is believed that postsynaptic dArc1 RNA is protected from the RNAi machinery. Taken together, the above results suggest that postsynaptic darc1 transcript and/or dArc1 protein is transported from presynaptic boutons to the postsynaptic compartment in a unidirectional manner.

Figure 2S:
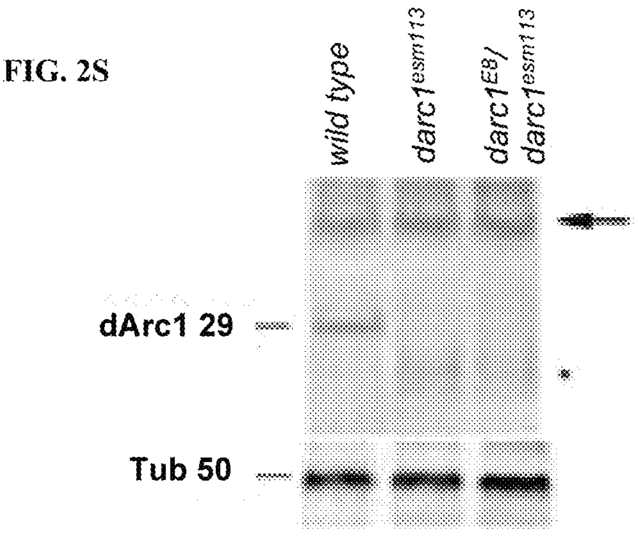
FIG. 2S: Western blot of body wall muscle protein extracts derived from the indicated genotypes probed sequentially with anti-dArc1 (top) and Tubulin (Tub; bottom).
Figure 2T:
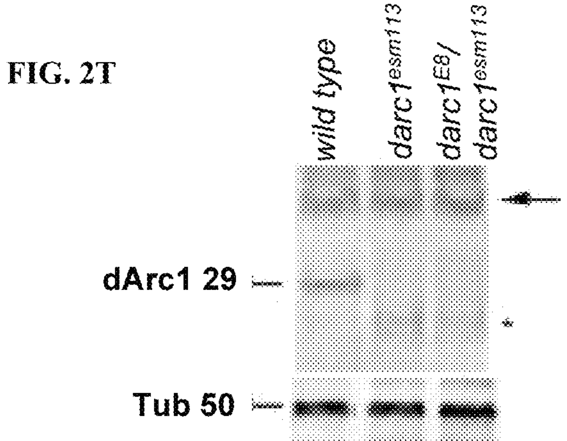
FIG. 2T: Western blot of body wall muscle protein extracts derived from the indicated genotypes probed sequentially with anti-dArc1 (top) and Tubulin (Tub; bottom). Numbers at the left of the blots represent molecular weight in kilodaltons. Arrow points to an unspecific band labeled by the dArc1 antibody. Tub-tubulin.
Figure 2U:
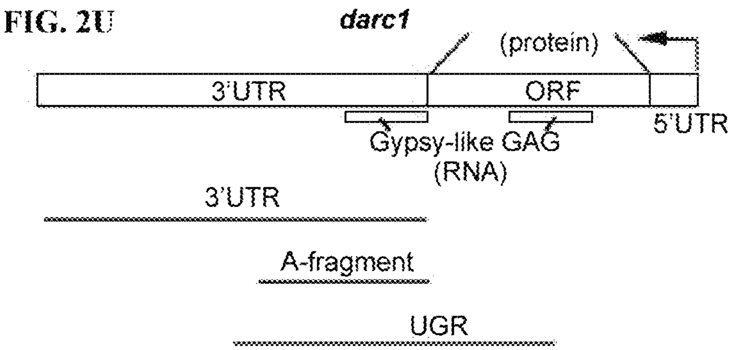
FIG. 2U: Diagram of darc1 mRNA showing the 5' UTR (blue), the open reading frame (ORF; red), and the 3' UTR (green). Black lines underneath represent different portions of the darc1 transcript. Orange bars represent regions of the dare mRNA resembling Gypsy-like Gag sequences. Note that the entire ORF encodes a Gypsy-like Gag protein.

To eliminate the possibility that dArc1 RNAi could, unlike other RNAi species, be transferred from neuron to muscles, an approach was used independent from RNAi to block EV release from presynaptic boutons. Rab11 is required for the release of exosome-like EVs at the NMJ. (Koles et al., 2012; Korkut et al., 2013). Consequently, it was examined whether expressing Rab11 dominant-negative (Rab11-DN) specifically in neurons induced a change in the levels of darc1 RNA or protein in the postsynaptic region. It was observed that this manipulation resulted in a highly significant reduction in darc1 RNA and protein in the postsynaptic region. FIGS. 2G, 2K, 2Q and 2R. When expressing Rab11DN in neurons, a decrease in dArc1 levels were observed in both the pre- and postsynaptic compartments suggesting that Rab11 could be involved in both the transport and release of dArc1. To distinguish between these two possibilities, the proportion of post synaptic dArc1 levels relative to presynaptic levels were calculated. This ratio was significantly decreased upon expressing Rab1DN in neurons. FIG. 2S. Together, these data provide additional evidence for the trans-synaptic transfer of darc1 mRNA and/or protein.

To further support the above conclusion, a dAr1c transgene was expressed in neurons, in a darc1E8/darc1esm113 mutant background. The transgene was composed of the darc1 open reading frame, plus the untranslated regions (UTR). This resulted in the presence of dArc1 protein, not only in presynaptic boutons, but also at the postsynaptic region. See, FIGS. 4 A1-A2. Interestingly, expressing a dArc1 transgene lacking the 3'UTR resulted in accumulation of the dArc1 signal in presynaptic terminals, but virtually no signal was observed at the postsynaptic region. FIGS. 4 B1-B2 and 4I. Notably, the distribution of dArc1 protein lacking the 3'UTR was variable, being highly enriched at some synaptic boutons, and less enriched in others. FIGS. 4 C1-C2. The quantification of the dArc1 protein signal in FIG. 4I omitted the highly-enriched boutons, because in order for the quantification to be informative, the fluorescent levels should be in a linear, non-saturating range. Those boutons with very high expression were orders of magnitude brighter, such that the signal became saturated with confocal acquisition parameters therefore facilitating the detection of a postsynaptice signal. Notably, expressing the dArc1 protein 3'-UTR construct in the muscles of the null mutant resulted in diffuse distribution of dArc1 protein signal throughout the muscle, and no postsynaptic enrichment was observed. FIGS. 4 D1-D2. Together, the above results provide compelling evidence that dArc1 protein and/or RNA are transferred from synaptic boutons to muscles, and that a normal dArc1 protein localization at postsynaptic sites depends on such transfer.

Yet, an alternative possibility is that alterations in darc1 RNA and/or protein in presynaptic boutons might limit a signaling mechanism that induces darc1 transcription or enrichment of darc1 RNA and/or protein at the postsynaptic compartment. RNA localization often depends on the RNA 3'UTR. Berkovits et al., "Alternative 3' UTRs act as scaffolds to regulate membrane protein localization" *Nature* 522:363-367 (2015). Consequently, a lack of darc1 3'UTR may prevent darc1 transfer. It was determined if expressing darc1 3'UTR alone in neurons was sufficient to allow the transfer. In these experiments darc1-3'UTR was fused to GFP, expressed in neurons, and the levels of GFP signal at the postsynaptic compartment was assessed. As a control, GFP was expressed alone. Expressing darc1-3'UTR-GFP, but not GFP alone, resulted in the presence of GFP signal in the muscle. Cf. FIGS. 4 E1-E2 with FIGS. 4 H1-H2 and 4J. Furthermore, expressing a shorter fragment of the 3'UTR (A-fragment) fused to GFP in motorneurons was also sufficient for the transport of GFP. Cf., FIGS. 4 F1-F2 and 4J with FIGS. 4 L1-L2. Interestingly, transfer of GFP was also observed when fusing it to a duplication of a darc1 gene fragment (UGR) that includes part of the 3'UTR. FIGS. 4 G1-G2 and 4J. Thus, darc1 mRNA can be transferred from neurons to postsynaptic muscles in a manner dependent on its 3'UTR. Notably, expressing darc1-3'UTR-GFP in neurons in a darc1 mutant background inhibited the transfer of GFP. FIG. 4K.

In addition to the presence of retroviral Gag-like sequences, structural analyses has revealed that the Arc Gag region resembles a three-dimensional structure of the HIV virus Gag region. Abrusan et al., "Turning gold into'junk': transposable elements utilize central proteins of cellular networks" *Nucleic Acids Res* 41:3190-3200 (2013); Campillos et al., "Computational characterization of multiple Gag-like human proteins" *Trends Genet* 22:585-589 (2006); Zhang et al., "Structural basis of arc binding to synaptic proteins: implications for cognitive disease" *Neuron* 86:490-500 (2015); and FIG. 7A. Given that retroviruses are also similar to retrotransposons, which are present throughout the mammalian and fly genomes, S2 deep sequencing data was generated using an algorithm designed to identify transposable elements, which are typically masked by the standard genome browsing algorithms. Strikingly, it was found that copia mRNA, a common *Drosophila* retrotransposon, was highly enriched in S2 EVs. FIG. 5A. Closer examination of the sequence reads revealed that the copia RNA sequences present in EVs corresponded to a predicted spliced short copia (copia$^S$) species consisting primarily of the Gag region. FIG. 5B. This is in contrast to the cellular Copia, which has RNA-seq reads representing the whole transcript. FIG. 6. The copia$^S$ isoform appeared to be selectively loaded into EVs as the ratio of copia$^S$/full length copia (copia$^L$) was 12.4/1 in the in the EV fraction, compared to 1.4/1 in the cell. To ascertain if Copia protein was also present in EVs a mass spectrometry-based proteomic analysis was performed of the S2 cell EV fraction. Notably, we found that the short Copia protein isoform was enriched in EVs. FIG. 5C.

Given that both Copias protein and copias RNA were found in S2 EVs, it was also determined if dArc1 protein, in addition to darc1 mRNA, was similarly enriched in S2 EVs. To determine the relative abundance and enrichment of EV proteins compared to those in the cell, mass spectrometry-based proteomic analysis was performed of EVs as compared to total cell proteins. Both dArc1 and dArc2 proteins were highly enriched in EVs as compared to cellular proteins. FIG. 5C. Interestingly, an mRNA expression analysis did not reveal any enrichment of darc2 mRNA in the EV fraction. The dArc2 ORF has 522% identity and 71.6% similarity with the dArc1 ORF, but lacks the putative C-terminal zinc finger domain, as well as the long darc1 3'UTR mRNA sequences present in darc1.

The Gag region of retroviruses is believed to bind to and package retroviral gRNA. Thus, the enrichment of both dArc1 protein and mRNA in EVs and their similarity to Gag sequences suggest that dArc1 protein could bind darc1 mRNA in vivo. This was addressed by conducting RNA immunoprecipitation (RIP) experiments using S2 cell and larval body wall muscle extracts, gel shift assays, and in vitro binding assays. In the RIP experiments, anti-dArc was used to immunoprecipitate dArc protein and the immunoprecipitate was analyzed by qRT-PCR to determine if darc1 mRNA was present in this fraction. FIG. 6. The dArc1 antibody co-immunoprecipitated darc1 mRNA in both S2 cells and body wall muscle preparations. FIGS. 5D and 5E. In contrast, no co-precipitation of other RNAs, such as 18s, eEfla1, and copia was observed, showing that the binding of dArc1 with its own mRNA has some degree of specificity in vivo. FIG. 5E. This is consistent with the idea that like retroviral Gag proteins, dArc1 protein may exist in a complex with darc1 mRNA in vivo.

To further explore the binding of dArc1 protein to a darc1 mRNA transcript in vivo, darc1-3'UTR-GFP or GFP alone were expressed in larval neurons. dArc1 protein was immunoprecipitated from extracts of body wall muscles derived from the above larvae, and the precipitate was tested for the presence of GFP mRNA by qRT-PCR. Anti-dArc1 antibodies immunoprecipitated GFP RNA only when GFP was fused to the darc1 3'UTR, but not when GFP was expressed alone, demonstrating that dArc1 protein binds darc1 3'UTR in vivo. FIG. 5F.

Whether purified dArc1 protein is capable of directly binding RNA was tested by co-incubating dArc1 protein with a biotinylated control mRNA or a biotinylated darc1 mRNA, when dArc1 protein was immobilized on streptavidin-labelled beads. FIG. 50. Electrophoretic mobility assays with both biotinylated or radiolabeled mRNAs did not demonstrate that the dArc1 protein was specific for darc1 mRNA versus control mRNA. This is consistent with published observations showing that HIV-1 Gag proteins associate specifically with HIV gRNA in vivo, but that this binding specificity is lost in vitro. (Comas-Garcia et al., "On the Selective Packaging of Genomic RNA by HIV-1" *Viruses* 8 (2016).

It was noted that cleaving the HIS-MBP tag after affinity purification of bacterially produced dArc1 protein resulted in the formation of a precipitate. Given that dArc Iresembles a Gag protein, and that retroviral Gag proteins have the ability to auto-assemble into capsids, the precipitate was examined at the EM level by negative staining. The presence of round structures of about 39.3±5.2 nm was seen, which resembled HIV capsids. FIGS. 8A and 8B. Thus, dArc1 protein appears to auto-assemble, and together with its ability to bind its own RNA in vivo, it is reasonable to suggest that has some properties similar to retroviruses.

Retroviruses may form their outer membrane cover as they exit from EVs. Meckes et al., "Exosomal communication goes viral" *J Virol* 89:5200-5203 (2015). Notably, dArc1 capsid-like structures were observed in our EV preparations. FIG. 9A. In these experiments, the EV preparation was treated with saponin to lyse EVs, and the resulting preparation examined by EM. The presence of ~40 nm round structures were observed resembling capsid-like elements obtained from purified dArc1. FIGS. 8C and 8D. Unlike those in purified protein preparations, however, these capsid-like structures derived from EVs appeared electron dense, perhaps indicating the presence of RNA within them. To confirm if the ~40 nm structures observed in EVs contained dArc1 protein, the grids were immunolabeled with anti-dArc1 antibodies and 10 nm gold conjugated secondary antibody. Many, but not all (FIG. 5E; white arrows) of the capsid-like structures were contained in gold granules. FIGS. 8E, 8F, and 8G (black arrows); and FIG. 10).

The role of dArc1 was examined during NMJ expansion, a process occurring throughout larval development, involving the addition of new synaptic boutons. Budnik et al., "Morphological plasticity of motor axons in *Drosophila* mutants with altered excitability" *J Neurosci* 10:3754-3768 (1990). In addition, the role of dArc1 was examined in rapid activity-dependent synaptic bouton formation. Ataman et al., "Rapid activity-dependent modifications in synaptic structure and function require bidirectional wnt signaling" *Neuron* 57:705-718 (2008). A drastic reduction in bouton numbers in 3rd instar (the last stage of larval development prior to metamorphosis) was found in darc1 null mutant larvae as compared to controls. FIGS. 11A, 11B, 11C, 11E, 11F, 11G, and 11. A similar result was observed upon expressing dArc-RNAi in motorneurons. FIGS. 11D, 11H, and 11. This suggests that a reduction of dArc1 in motorneurons inhibits synaptic expansion during larval development. Consistent with this model, presynaptic expression of a genomic darc1 rescue construct in motorneurons completely rescued the reduced number of synaptic boutons resulting from eliminating or decreasing dArc1 levels. FIG. 11I. In contrast, expressing the darc1 rescue construct in postsynaptic muscles, or eliminating its 3'UTR, did not rescue the mutant phenotype. FIG. 11I.

NMJ expansion involves the transient formation of immature synaptic boutons (ghost boutons) devoid of neurotransmitter release sites and postsynaptic proteins and specializations. Ataman et al., "Rapid activity-dependent modifications in synaptic structure and function require bidirectional wnt signaling" *Neuron* 57:705-718 (2008); and Koon et al., "Autoregulatory and paracrine control of synaptic and behavioral plasticity by octopaminergic signaling" *Nat Neurosci* 14:190-199 (2011). At the postsynaptic side, this is followed by the recruitment of postsynaptic proteins and formation of postsynaptic structures. Several mutations in genes required for NMJ development result in a reduced number of synaptic boutons and an accumulation of ghost boutons. Ataman et al., "Nuclear trafficking of *Drosophila* Frizzled-2 during synapse development requires the PDZ protein dGRIP" *Proc Natl Acad Sci USA* 103:7841-7846 (2006); and Harris et al., "Shank Modulates Postsynaptic Wnt Signaling to Regulate Synaptic Development". *J Neurosci* 36:5820-5832 (2016). It was found that, in addition to a reduction in bouton numbers, transallelic darc1 mutations or darc1 downregulation in neurons resulted in an accumulation of ghost boutons. FIGS. 11F, 11G, 11H and 11J. As with the number of synaptic boutons, this phenotype was completely rescued by expressing the genomic dare rescue construct in neurons, but not in muscles. FIG. 11J. Moreover, expressing a darc1 transgene lacking the 3'UTR in neurons or muscles did not result in rescue.

NMJ expansion can be stimulated by increased synaptic activity during larval development. Budnik et al., "Morphological plasticity of motor axons in *Drosophila* mutants with altered excitability" *J Neurosci* 10:3754-3768 (1990). In addition, acute spaced stimulation of motorneurons gives rise to the rapid formation of ghost boutons, some of which subsequently undergo maturation. Ataman et al., "Rapid activity-dependent modifications in synaptic structure and function require bidirectional wnt signaling" *Neuron* 57:705-718 (2008). To determine if dArc1 was required for this activity-dependent new bouton formation, dArc1 levels were reduced by expressing dArc1-RNAi in neurons. While the formation of ghost boutons upon spaced stimulation was normal in control animals, it was significantly reduced upon dArc1 downregulation. FIGS. 11K, 11L, 11M, 11N and 11O. Thus, like mammalian Arc, darc1 is required for both developmental and acute forms of synaptic plasticity.

It should be noted that it has been previously reported that dArc1 is not involved in synaptic plasticity. Mattaliano et al., "The *Drosophila* ARC homolog regulates behavioral responses to starvation" *Mol Cell Neurosci* 36:211-221 (2007). To determine the potential reason for this discrepancy, the darc1 genomic region of the wild type strain Canton-S(CS) was sequenced. Surprisingly, a neighboring gene annotated as pseudo-gene (referred to here as UGR) in the fly genome and located between darc1 and darc2 was absent in CS. FIG. 11A. The annotated *Drosophila* genome sequence was derived from a wild type strain different than CS, Oregon-R (OR). Thus, there is a polymorphism in the darc1-darc2 intergenic region locus between CS and OR wild type strain. Closer analysis of the UGR revealed that it was a duplication of a fragment of the darc1 open 16 reading frame (ORF) and part of its 3'UTR. FIG. 7A. To determine the potential impact of the UGR element in the OR strain, darc1 mRNA and protein levels were compared between CS and OR. Notably, darc1 RNA and protein levels were drastically reduced in OR compared to CS. FIG. 7B. In addition, the number of synaptic boutons was significantly reduced in OR. FIGS. 7C, 7D and 7E. Although it is not necessary to understand the mechanism of an invention it is believed that the difference between the present darc1 mutant analysis and Mattaliano et al. might arise from this difference between strains. Interestingly, the darc1-darc2 intergenic region from original S2 cells lack the UGR. Schnieder I., "Cell lines derived from late embryonic stages of *Drosophila melanogaster' J Embryol Exp Morphol* 27:353-365 (1972). Consequently, it is possible that the presently found UGR is a relatively recent divergence.

III. Transposon Fragment Exosomes

In one embodiment, the present invention contemplates an exosome comprising a fragment of a transposon. In one embodiment, the transposon comprises a a ribonucleic acid sequence and a protein. Preliminary data demonstrates that a GFP-tagged transposon (copia) crosses a neuronal synapse and is transferred into the post-synaptic neuronal as evidenced by the accumulation of GFP in post-synaptic nuclei. Although it is not necessary to understand the mechanism of an invention it is believed that such transposon exosomes are generic payload carriers directed to the nuclei of a target cell.

Darc1-3'UTR as a Mechanism of dArc1 Loading into EVs

*Drosophila* Arc1 and Arc2 appear to result from a genomic duplication event and are believed composed of a Gypsy transposon-derived Gag domain. While an ORF of darc1 and darc2 are highly conserved, they differ vastly in their 3'UTR. Studies with a GFP reporter show that the 3'UTR of darc1 mRNA is necessary and sufficient for the transport and accumulation of darc1 postsynaptically (data not shown). This suggests that the 3'UTR of darc1 imparts some function needed to load darc1 mRNAs into EVs. In this regard, the dArc2 protein, but not its mRNA, is enriched in EVs. While the protein and mRNA sequences of darc1 and darc2 are very similar, they differ dramatically in the 3'UTR, which in the case of darc2 is much shorter. This difference might explain the absence of darc2 mRNA in EVs. Data suggests that darc1 mRNA may be instructive as a model to understand EV RNA loading in vivo.

Alternatively, RNA binding to Gag proteins might be required to assemble a capsid, which might be needed for EV loading. The rat Arc 3'UTR contains Gypsy-like sequences, transposon sequences similar to those of darc1. Since these genes most likely evolved independently the similarity of the mammalian and fly Arc proteins and mRNAs indicates the possibility of convergent evolution of this mechanism of trans-cellular communication. Abrusan et al., Turning gold into 'junk': transposable elements utilize central proteins of cellular networks. Nucleic Acids Res 41:3190-3200 (2013).

Trans-Synaptic dArc1 Transfer in *Drosophila* Synapse Development and Plasticity Studies of darc1 mutants, dArc1-RNAi, and expression of transgenic dArc1 variants suggest that the transfer of dArc1 may occur for normal expansion of the NMJ, synaptic bouton maturation, and activity-dependent synaptic bouton formation. For example, expressing a dArc1 transgene lacking the 3'UTR in neurons, while resulting in the localization of a transgenic protein at presynaptic boutons, it is not transferred to a postsynaptic region and fails to rescue mutant phenotypes at the NMJ. In contrast, expressing a transfer-competent dArc1 transgene, containing the 3'UTR, results in complete rescue. Therefore, it is not just the presence of dArc1 in presynaptic terminals, but the actual transfer to the postsynaptic region which may provide for dArc1 function at the NMJ. This is also supported by findings that expressing dArc1 containing the 3'UTR in muscles alone did not result in normal postsynaptic dArc1 localization, nor did it rescue mutant phenotypes at the NMJ. Thus, both normal postsynaptic localization of dArc1 and its function in synaptic development and plasticity requires dArc1 transfer from the presynaptic terminus. The requirement of darc1-3'UTR also provides support to the idea that darc1 mRNA, and not just dArc1 protein is transferred, which is also supported by findings of both dArc1 protein and RNA in EVs.

Previous studies show that the transfer or release of EV proteins, such as Evi and Wg, is enhanced by electrical activity. Ataman et al., "Nuclear trafficking of *Drosophila* Frizzled-2 during synapse development requires the PDZ protein dGRIP" *Proc Natl Acad Sci USA* 103:7841-7846 (2006). Similar observations have been made with cultured mammalian neurons and glia. Faure et al., "Exosomes are released by cultured cortical neurones" *Mol Cell Neurosci* 31:642-648 (2006); and Frubbeis et al., "Neurotransmitter-triggered transfer of exosomes mediates oligodendrocyte-neuron communication" *PLoS Biol* 11:e1001604 (2013). This opens the possibility that dArc1 might be delivered to postsynaptic sites in an activity-dependent fashion. This would allow the functional modification of specific postsynaptic sites.

IV. Trans-Synaptic Transfer as a General Mechanism of Arc/dArc1 Function

In mammals, Arc is a master regulator of synaptic plasticity, being involved in many aspects of synapse formation, maturation and plasticity, as well as in learning and memory Shepherd et al., "New views of Arc, a master regulator of synaptic plasticity" *Nat Neurosci* 14:279-284 (2011). Arc expression is induced by synaptic activity and its mRNA becomes localized to active dendritic spines, where it contributes to local translation during synaptic plasticity. Farris et al., "Selective localization of are mRNA in dendrites involves activity- and translation-dependent mRNA degradation" *J Neurosci* 34:4481-4493 (2014). Not surprisingly, in humans, mutations in Arc are associated with multiple neurological disorders affecting synapses, including autism spectrum disorders, Angelman syndrome, and schizophrenia. Alhowikan A. M., "Activity-Regulated Cytoskeleton-Associated Protein Dysfunction May Contribute to Memory Disorder and Earlier Detection of Autism Spectrum Disorders" *Med Princ Pract* 25:350-354 (2016); Cao et al., "Impairment of TrkB-PSD-95 signaling in Angelman syndrome" *PLoS Biol* 11:e1001478 (2013); and Fromer et al., "De novo mutations in schizophrenia implicate synaptic networks" *Nature* 506:179-184 (2014), respectively. While some mechanisms of Arc function, such as its involvement in trafficking of glutamate receptors during plasticity are beginning to be elucidated, the extent of its roles remain to be deciphered. Chowdhury et al., "Arc/Arg3.1 interacts with the endocytic machinery to regulate AMPA receptor trafficking" *Neuron* 52:445-459 (2006).

Highly significant roles are suggested for Arc/dArc1 in trans-synaptic signaling as studies reveal the significance of a long-noted but mysterious feature of Arc/dArc1 protein, its resemblance to retroviral Gags. Like retroviruses, Arc/dArc1 proteins can form capsids capable of packaging RNAs. These capsids can be loaded into EV-like vesicles that can be released from synaptic sites and taken up by synaptic partners. While a functional role in synaptic development and plasticity is documented here at the *Drosophila* NMJ, the significance of this transfer at mammalian synapses remains to be determined. In *Drosophila*, dArc1 protein and mRNA are present both inside presynaptic boutons and at the postsynaptic muscle region. In contrast, Arc has previously been reported to localize exclusively in dendrites, and not at presynaptic sites. Lyford et al., "Arc, a growth factor and activity-regulated gene, encodes a novel cytoskeleton-associated protein that is enriched in neuronal dendrites" *Neuron* 14:433-445 (1995).

The finding that mammalian Arc is also released in EVs raises the possibility that this release might serve as a signaling mechanism between dendritic spines. However, if this signaling process plays a role in synaptic plasticity, it would call into question the synapse-specificity of synaptic plasticity documented in the mammalian brain. Viola et al., "The tagging and capture hypothesis from synapse to memory" *Prog Mol Biol Transl Sci* 122:391423 (2014). An alternative possibility is that mammalian Arc, while primarily being localized at postsynaptic sites, it is also present in lesser amounts at presynaptic terminals. Indeed, in the fly, most of the dArc1 protein and RNA is present at the postsynaptic region. Studies of Arc downregulation in presynaptic neurons and its effect in the localization of Arc at dendritic spines, may serve to distinguish between these possibilities.

EXPERIMENTAL

Example I

Fly Strains

All flies were raised on standard molasses formulation food at either 25° C. (most crosses) or 29° C. (RNAi crosses). The following fly lines were used:

i) UAS-dArc1-RNAi (31122, Vienna *Drosophila* Research Center).
ii) UAS-Rab11DN[N1241](Satoh et al., "Rab1 mediates post-Golgi trafficking of rhodopsin to the photosensitive apical membrane of *Drosophila* photoreceptors" Development 132:1487-1497 (2005).
iii) UAS-dArc1-RNAi(2)
iv) CS (1, Bloomington *Drosophila* stock center, BDSC).
v) OregonR (6362, BDSC).
vi) UAS-GFP (5431, BDSC).
vii) UAS-darc1-3'UTR-GFP
viii) UAS-darc1-A-fragment-GFP.
ix) UAS-darc1-UGR-GFP
x) C380-Gal4. Budnik V., "Synapse maturation and structural plasticity at *Drosophila* neuromuscular junctions" *Curr Opin Neurobiol* 6:858-867 (1996).
xi) C57-Gal4. Budnik V., "Synapse maturation and structural plasticity at *Drosophila* neuromuscular junctions" *Curr Opin Neurobiol* 6:858-867 (1996).

Example II

Null Allele Generation

A mutant allele of dArc1 was generated by CRISPR/Cas9-mediated genomic engineering. Briefly, sequences encoding two sgRNAs targeting dArc1 gene flanking sites which were predicted to have no off targets (flyCRISPR target finder; tools.flycrispr.molbio.-wisc.edu/targetFinder/) were cloned into the pCFD4 plasmid. This construct was injected into actin-Cas9 expressing embryos and potentially mutant chromosomes were captured over a balancer chromosome and made into stocks which were subsequently screened for the desired deletion by PCR employing deletion-flanking primers sets. Sequencing of PCR products generated from the E8 line revealed that the deletion was that expected. Immunostaining of 3rd instar larval body walls with anti-dArc1 antibody established a lack of dArc1 protein in this mutant line.

Example III

Constructs

UAS-darc1-3'UTR-GFP constructs were cloned into pAWG vector using the Gateway system (ThermoFisher). The GFP with resulting 3'UTR fragments were amplified out of this construct, and cloned into pENTR/DTOPO. The resulting construct was finally cloned into the pTWM construct, containing an attB site for targeted genomic insertion.

3' UTR (SEQ ID NO: 1):
CACCTAGATAGAATAGGCGACAAAAAGAACATCAAATACCAACAGGCAGCA
GCCAA CGTCATTGATGACCTCATCGCTGCTGCCGCCCACCCAAACAGAAC
TTTTCGTAGCCTCGCCAGCCGATCGACGTCAGAGAGAGCCCAACAACCGGA
GAGCTGGAGATGGGGAGCAGCCACATCAACAGCAGCAACAGCAGCCACATC
TCTTCATACTCTTCATACTCACTGGCAATCGGCGTGCCGGTAAGCCTCGAC
TAGCTTCTGAAATCCACAAATCCACGCTGTTTGTATTGCTATTCGCAATGC
CTCGAAAACGCTCTATTTTCATATAATTTCACGCCGACTTGCGGCTACTTT
GGCACAGAACGCCAGCTTTTGGAAAGCAATAATTTTTATTGCAACATTGAA
CCTTTATTTGCAACTAGAAACTAGATTTCGAGAATCATCGGGCGGGGCGGC
TGAGGATCTGGCATTTCGTCCGTAAGATCGGTTATTCGCAATGGAGGAATA
TGATATTCGAACCAAATGGCGGGTGAAGTGCCTCGGCATGGAGCTCCATTT
TCTTCGAATCTTATGTTTTGACATTGCGAGTCTGAAATGGATGTTGCCTGA
TCTCCAGCCGCCCCGCACAACCGTTGATTCTCACAACCGCCGGCTCCACTT
TGTGCCGGTCAGCGGAGAAAAAGCGATTATTTGGCTATCAAAAGATATGAT
CACTGTGTTGAGAGACATGGCAATCATCGCTATTGTAACCATATATTTGCT
GATTTTTCGTCTGATCCTGGTCCTTTGTGAAGCTAGCAAAAAACCCCCCGC
CCGGTGAATGCCCACTTAGATCCTTTTGCAGGAGGATTTCGACGGCCCTGA
AGGTGGGCGCCACCCGTTTCCGGTAGCGGCTTCGGCTGCTTCCGGTTTCCG
GTGTCGCAACCCTTCGCGATGTCCCCCGTGCGAGTGGAGCTACAGTGGGCG
TGAGCCGGGCAAAACCTAAATTTCTTCGGAGATTTAAAAAACCAACAAATT
TTTTGACTTTTGTCAAAACAATTCGAACCCACATAGCACTACGATGGCTAA
CGATTCGCCATCCGTGCGGTTGGCACGCCAAAACTGTCTCTTCGAGATCAC
GGGCCTAGGGCTGTTTAACATTCGACCCAAGCGATTTCGCGACAGGCTTCG
GCACGCCAGTATATAACCCAAAACACACAAACGTCAGGGGCTGGAACGCGT
CACTGCCGTGCTCCTCCAGCCGGCACAGTCATTCCCCGCCCCCACACCAAG

-continued

CAAAACCGGCCGCTTGTGCAGATGACATAGGCGCGACCAGCCAACTGACCC
GGCTGACCAGACTTGCACCGTGCGCCATCAACTGGAATCTTGGCCACAAGC
ACAGCAATAGTTTGGCCCGCTATTCCCACACAGAAACCCAGAGTGGGGGCC
TATGGAAGACCACAAGTGGTTGCGTGGAACTGCTAAAAATATAAAACTGTA
ACTAAAGACTGAAACTAGAAAACAACCATTAAACTCAGAAACGG

A-Fragment (SEQ ID NO: 2):
CACCTAGATAGAATAGGCGACAAAAAGAACATCAAATACCAACAGGCAGCA
GCCAA CGTCATTGATGACCTCATCGCTGCTGCCGCCCACCCAAACAGAAC
TTTTCGTAGCCTCGCCAGCCGATCGACGTCAGAGAGAGCCCAACAACCGGA
GAGCTGGAGATGGGGAGCAGCCACATCAACAGCAGCAACAGCAGCCACATC
TCTTCATACTCTTCATACTCACTGGCAATCGGCGTGCCGGTAAGCCTCGAC
TAGCTTCTGAAATCCACAAATCCACGCTGTTTGTATTGCTATTCGCAATGC
CTCGAAAACGGCTCTATTTTCATATAATTTCACGCCGACTTGCGGCTACTT
TGGCACAGAACGCCAGCTTTTGGAAAGCAATAATTTTTATTGCAACATTGA
ACCTTTATTTGCAACTAGAAACTAGATTTCGAGAATCATCGGGCGGGGCGG
CTGAGGATCTGGCATTTCGTCCGTAAGATCGGTTATTCGCAATGGAGGAAT
ATGATATTCGAACCAAATGGCGGGTGAAGTGCCTCGGCATGGAGCTCCATT
TTCTTCGAATCTTATGTTTTGACATTGCGAGTCTGAAATGGATGTTGCCTG
ATCTCCAGCCGCCCCGCACAACCGTTGATTCTCACAACCGCCGGCTCCACT
TTGTGCCGGTCAGCGGAGAAAAAGCGATTATTTGGCTATCAAAAGATATGA
TCACTGTGTTGAGAGACATGGCAATCATCGCTATTGTAACCATATATTTGC
TGA UGR (SEQ ID NO: 3):
TTGTGGCGGTTCCTCCGCAAGGAGGCCACCACGTGGAAGGAAGCCATCGCT
CTCATCCGCGAACACTTCTCGCCCACCAAGCCCGCCTACCAGATCTACATG
GACTTCTTCCAAAACAAGCAGGACGACCATGACCCCATTGACACCTTCGTC
ATCCAGAAGCGAGCGCTGCTGGCCCAGCTGCCCAGCGGTCGCCACGACGAG
GAAACGGAACTGGATCTTCTGTTCGGTCTGCTGAACATCAAGTACCGCAAG
CACATCTCCCGCCACAGTGTCCATACCTTCAAGGATCTCCTGGAACAGGGC
CGCATCATCGAGCACAACAACCAGGAGGACGAGGAACAGCTTGCCACAGCA
AAGAACACCCGTGGCTCCAAGCGCACCACCCGCTGCACCTACTGCAGTTTC
CGGGGGCACACCTTCGACAACTGCCGTAAGCGCCAGAAGGATCGGCAGGAG
GAGCAGCACGAGGAGTAGGCGACAAAAAGAACATCAAATACCAACAGGCAG
CAGCCAACGTCATTGATGACCTCATCGCTGCTGCCGCCCACCCAAACAGAA
CTTTTCGTAGCCTCGCCAGCCGATCGACGTCAGAGAGAGCCCAACAACCGG
AGAGCTGGAGATGGGGAGCAGCCACATCAACAGCAGCAACAGCAGCCACAT
CTCTTCATACTCTTCATACTCACTGGCAATCGGCGTGCCGGTAAGCCTCGA
CTAGCTTCTGAAATCCACAAATCCACGCTGTTTGTATTGCTATTCGCAATG
CCTCGAAAACGGCTCTATTTTCATATAATTTCACGCCGACTTGCGGCTACT
TTGGCACAGAACGCCAGCTTTTGGAAAGCAATAATTTTTATTGCAACATTG
AACCTTTATTTGCAACTAGAAACTAGATTTCGAGAATCATCGGGCGGGGCG
GCTGAGGATCTGGCATTTCGTCCGTAAGATCGGTTATTCGCAATGGAGGAA -continued

```
TATGATATTCGAACCAAATGGCGGGTGAAGTGCCTCGGCATGGAGCTCCAT
TTTCTTCGAATCTTATGTTTTGACATTGCGAGTCTGAAATGGATGTTGCCT
GATCTCCAGCCGCCCCGCACAACCGTTGATTCTCACAACCGCCGGCTCCAC
TTTGTGCCGGTCAGCGGAGAAAAAGCGATTATTTGGCTATCAAAAGATATG
ATCACTGTGTTGAGAGACATGGCAATCATCGCTATTGTAACCATATATTTG
CTGATTTTTCGTCTGATCCTGGTCCTTTGTGAAGCTAGCAAAAAACCCCCC
GCCCGGTGAATGCCCACTTAGATCCTTTTGCAGGAGGATTTCGA
```

The UAS-dArc-RNAi(2) construct was cloned by first cloning an dArc1 fragment, that was non-overlapping with the VDRC 31122 line, using the following primers:

```
Forward Primer:
                                (SEQ ID NO: 4)
TCAGTTCAAATCACCGGCCG

Reverse Primer:
                                (SEQ ID NO: 5)
GTATGTCTCGATGTTGCCGATG
```

The PCR product was cloned into PENTR-DTOPO (ThermoFisher), and then using the Gateway system (ThermoFisher) was cloned into pWalium10. All constructs were then injected into flies and integrated at site attP2 on the third chromosome, through targeted integration by BestGene.

The UAS-dArc1 rescue transgene was synthesized (Genscript) and using the Gateway system (ThennoFisher) cloned into the pTWM vector.

```
UAS-dArc1 Rescue Transgen;
                                (SEQ ID NO: 6)
CAATACATAGATACTTAATTTGGATTTTAATTTTAATAAAAAAAAACTAAC
AAATTTTCTATCGCCTGTTAGTAATTAGACTATAAGTCAGGAATTTCGTAC
GACAATGAAAAACTATAAGTTCCAAGAAAAACACTAAAAATTCAAGAATGT
GAGCAGCAGTTCTATATTATCCAAATAGTAAGTCAGTTAATAATAAAAAAT
AATACATTCTATTACTCGTATACAAATTATAAGTAACCACATATATTGTGA
CCATTTCACAAAAAAAATGTAATAGTACAAATCAAGGAAAACTCCCTAGAAA
CCGCATGCAAGCCTCTACAAAACTTTGTTTATCAGTTTGGGCCACATTTAC
AATCAGGTTTGTCCATCAGTACATATAGTAGTTACCGGCTTTCAAACTGCT
ATTTTTATATAGCGCGATGATTCACTCTGAGCAATAATACCAAAAACATAG
ACCTTCCCTCTCTTATTGGCTCTCCCCAATGCCTCAAGCTTTTTCGAAGTT
CGATTTCACAACAGGCGGATATAAAAGGGCTGCAATGTGGGAGAGCTGTTC
AGTTCAAATCACCGGCCGCATTCGCTACACTGGCTTTGTCCGCCGACTGAA
CCAAGATTAATTTGATCACCTAACCTCACACAGCAGCGAAAATGGCCCAGC
TTACACAATGGCCCAGCTTACACAGATGACCAACGAGCAGCTCCGCGAGCT
GATCGAAGCTGTAAGAGCGGCCGCCGTGGGCGCCGCCGGAAGTGCAGCAGC
AGCCGGAGGAGCAGACGCCAGCAGAGGCAAAGGCAACTTCTCCGCTTGCAC
ACACAGCTTCGGCGGAACCCGCGACCACGACGTGGTCGAGGAGTTCATCGG
CAACATCGAGACATACAAGGATGTAGAAGGTATCAGCGACGAGAACGCCCT
```

-continued

```
GAAGGGCATCTCGCTGCTGTTCTACGGTATGGCCAGCACCTGGTGGCAAGG
CGTCCGCAAGGAGGCCACCACGTGGAAGGAAGCCATCGCTCTCATCCGCGA
ACACTTCTCGCCCACCAAGCCCGCCTACCAGATCTACATGGAATTCTTCCA
AAACAAGCAGGACGACCATGACCCCATTGACACCTTCGTCATCCAGAAGCG
AGCGCTGCTGGCCCAGCTGCCCAGCGGTCGCCACGACGAGGAAACGGAACT
GGATCTTCTGTTCGGTCTGCTGAACATCAAGTACCGCAAGCACATCTCCCG
CCACAGTGTCCATACCTTCAAGGATCTCCTGGAACAGGGCCGCATCATCGA
GCACAACAACCAGGAGGACGAGGAACAGCTTGCCACAGCAAAGAACACCCG
TGGCTCCAAGCGCACCACCCGCTGCACCTACTGCAGTTTCCGGGGGCACAC
CTTCGACAACTGCCGTAAGCGCCAGAAGGATCGGCAGGAGGAGCAGCACGA
GGAGTAGGCGACAAAAAGAACATCAAATACCAACAGGCAGCAGCCAACGTC
ATTGATGACCTCATCGCTGCTGCCGCCCACCCAAACAGAACTTTTCGTAGC
CTCGCCAGCCGATCGACGTCAGAGAGAGCCCAACAACCGGAGAGCTGGAGA
TGGGGAGCAGCCACATCAACAGCAGCAACAGCAGCCACATCTCTTCATACT
CTTCATACTCACTGGCAATCGGCGTGCCGGTAAGCCTCGACTAGCTTCTGA
AATCCACAAATCCACGCTGTTTGTATTGCTATTCGCAATGCCTCGAAAACG
GCTCTATTTTCATATAATTTCACGCCGACTTGCGGCTACTTTGGCACAGAA
CGCCAGCTTTTGGAAAGCAATAATTTTTATTGCAACATTGAACCTTTATTT
GCAACTAGAAACTAGATTTCGAGAATCATCGGGCGGGGCGGCTGAGGATCT
GGCATTTCGTCCGTAAGATCGGTTATTCGCAATGGAGGAATATGATATTCG
AACCAAATGGCGGGTGAAGTGCCTCGGCATGGAGCTCCATTTTCTTCGAAT
CTTATGTTTTGACATTGCGAGTCTGAAATGGATGTTGCCTGATCTCCAGCC
GCCCCGCACAACCGTTGATTCTCACAACCGCCGGCTCCACTTTGTGCCGGT
CAGCGGAGAAAAAGCGATTATTTGGCTATCAAAAGATATGATCACTGTGTT
GAGAGACATGGCAATCATCGCTATTGTAACCATATATTTGCTGATTTTTCG
TCTGATCCTGGTCCTTTGTGAAGCTAGCAAAAAACCCCCCGCCCGGTGAAT
GCCCACTTAGATCCTTTTGCAGGAGGATTTCGACGGCCCTGAAGGTGGGCG
CCACCCGTTTCCGGTAGCGGCTTCGGCTGCTTCCGGTTTCCGGTGTCGCAA
CCCTTCGCGATGTCCCCCGTGCGAGTGGAGCTACAGTGGGCGTGAGCCGGG
CAAAACCTAAATTTCTTCGGAGATTTAAAAAACCAACAAATTTTTTGACTT
TTGTCAAAACAATTCGAACCCACATAGCACTACGATGGCTAACGATTCGCC
ATCCGTGCGGTTGGCACGCCAAAACTGTCTCTTCGAGATCACGGGCCTAGG
GCTGTTTAACATTCGACCCAAGCGATTTCGCGACAGGCTTCGGCACGCCAG
TATATAACCCAAAACACACAAACGTCAGGGGCTGGAACGCGTCACTGCCGT
GCTCCTCCAGCCGGCACAGTCATTCCCCGCCCCCACACCAAGCAAAACCGG
CCGCTTGTGCAGATGACATAGGCGCGACCAGCCAACTGACCCGGCTGACCA
GACTTGCACCGTGCGCCATCAACTGGAATCTTGGCCACAAGCACAGCAATA
GTTTGGCCCGCTATTCCCACACAGAAACCCAGAGTGGGGGCCTATGGAAGA
CCACAAGTGGTTGCGTGGAACTGCTAAAAATATAAAACTGTAAAACTAAAG
ACTGAAACTAGAAAACAACCATTAAACTCAGAAACGGAAAACTGCGTAATT
```

-continued

```
GTTTTTATTTTATGGGGTGGATGGGACAACATTTTTACAGGGAATCATTTT

TTTAAACAAA
```

Example IV

Immunocytochemistry And Antibodies

Body wall muscles from third instar larva were dissected in low calcium (0.1 mM Calcium) HL3 saline and fixed in either Bouin's fixative (0.9% picric acid, 5% acetic acid, 9% formaldehyde, 2.5-5% methanol) or 4% paraformaldehyde in 0.1 M phosphate buffer. Fixed larvae were washed and permeabilized in PBT (0.1 M phosphate buffer, 0.2% (v/v) Triton X-100) and incubated in primary antibody overnight.

Samples were washed three times with PBT and incubated in secondary antibodies for 2 hours. After incubation with secondary antibodies, samples were washed with PBT and mounted in Vectashield® (Vector Laboratories). The following antibodies were used: anti-dArc1 (1:500 for ICC; 1:1000 for Western Blot), anti-GFP (Developmental Studies Hybridoma Bank, 4c9, 1:200(DSHB-GFP-4C9 (DSHB Hybridoma Product DSHB-GFP-4C9)) and rabbit anti-DLG, 1:40,000. Koh et al., "Regulation of DLG localization at synapses by CaMKII-dependent phosphorylation. Cell 98, 353-363 (1999). DyLight-conjugated secondary antibodies were from Jackson ImmunoResearch or ThermoFisher and used at the following dilutions: DyLight-594-conjugated goat anti-HRP at 1:200 for ICC; DyLight-488-, or DyLight-594-conjugated anti-mouse, or antirabbit at 1:200.

dArc1 antibodies were generated against the first 56 amino acids of dArc1 by immunizing rabbits and rats with purified 6×His tagged peptides (Pocono Rabbit Farm and Laboratory). A synthetic gene representing the first 56 amino acids was synthesized into pET155 (ThermoFisher), transfected into BL21(DE3) bacterial cells (ThermoFisher) and His tagged dArc1 peptide was purified on a nickel column (Pierce).

Example V

Fluorescent In Situ Hybridization (FISH)

In situ hybridization was performed as described previously with minor modifications. Speese et al., "Nuclear envelope budding enables large ribonucleoprotein particle export during synaptic Wnt signaling" *Cell* 149:832-846 (2012). Briefly larval body wall muscles were dissected as described above and fixed with 4% paraformaldyhyde for 30 min. Preparations were then washed three times, 10 min each, with 0.2% PBT with RNasin (Promega). Samples were equilibrated with hybridization buffer (2×SSC, 10% dextran sulfate, RNasin (Promega), 50% formamide). Gene specific probes (125 ng probe, 1.25 μg salmon sperm DNA, 1.25 μg yeast tRNA) were heated to 80° C. for 5 min and chilled on ice immediately. Probes were then combined with equal volumes of 2× hybridization buffer (final concentration of 2.5 ng/μL gene specific probes). Samples were incubated with probes for 3 hours at 37° C. To visualize synaptic boutons, samples were incubated with goat anti-HRP-DylightS94 (1:200, ThermoFisher).

Example VI

Probe Preparation

Briefly, probes were designed based on the cDNA sequences of target genes. The probes were produced by nick translation of the PCR product (Bionick; Invitrogen) with digoxigenin-11-dUTP (Roche) for 2.5 hrs at 18° C., and the reaction was inactivated by heating to 65° C. for 10 min. Probes were precipitated and resuspended in formamide and stored at −80° C. Blocking probe against the *Drosophila shibire* gene was prepared using the same method except dTTP was used instead of digoxigenin-labeled dUTP.

dArc1 Probe Primers:

```
Forward dArc1 primer:
                                  (SEQ ID NO: 7)
GATTTTTCGTCTGATCCTGGTC

Reverse dArc1 primer:
                                  (SEQ ID NO: 8)
CCGTTTCTGAGTTTAATGGTTG
```

Example VII

Confocal Microscopy and Signal Intensity Measurements

Images were acquired on Zeiss LSM 700 or LSM 800 confocal microscope equipped with a Zeiss 63× Plan-Apochromat 1.4 NA DIC oil immersion objective. For quantification of signal intensity, NMJs were imaged at identical settings for control and experimental groups on a Zeiss Axioplan microscope equipped with a Yokogawa CSU10 spinning disk confocal scanning unit and a Hamamatsu 9100 EM-CCD camera (512×512) and a 40×ECPlan-NeoFluar 1.3 NA objective. Briefly, after image acquisition, the bouton volume bounded by HRP staining was selected, and fluorescence intensity inside (presynaptic) and outside (postsynaptic) the boutons was determined as the sum of total pixel intensity and normalized to bouton volume, as described previously. Ramachandran et al., "A critical step for postsynaptic F-actin organization: regulation of Baz/Par-3 localization by aPKC and PTEN" *Dev Neurobiol* 69:583-602 (2009).

Example VIII

Exosome Preparation

Exosomes were prepared from S2 cells that were cultured in serum-free medium to avoid contamination from Bovine serum exosomes. Cultures were grown in spinner flasks (BellCo Glass Inc.) at 22° C. and harvested at 1-1.5×10$^6$ cells/mL density. Exosomes were further purified using a differential centrifugation, and finally through sucrose density gradient centrifugation. Koles et al., "Mechanism of evenness interrupted (evi)-exosome release at synaptic boutons" *J Biol Chem* 287:16820-16834 (2012).

In particular, an SV40 ter* plasmid comprising an actin promoter gene, a green fluorescent protein (GFP) reporter gene fused with an MCS gene that is transfected into S2 cells. Upon MCS-GFP mRNA expression GFP accumulation may be measured in the media (e.g., by quantitative polymerase chain reaction). Such a model may be used to measure the expression of arc gene fragments, including but not limited to: i) a first are fragment comprising a 5' UTR, an ORF and a 3' UTR; ii) a second arc fragment comprising a 5' UTR and an ORF; iii) a third arc fragment comprising a 3' UTR. Alternatively, the model may be used to measure the expression of a full length arc gene. In such models, a negative control gene may be used including, but not limited to pAGW (ccdB). It is expected that the pAGW expression would result in very little GFP detection as opposed to a significant amount of GFP expression. Such differences in GFP expression are determined by a measurement of fluorescent intensity. See, FIG. 12.

Example IX darc1 mRNA Enriched dArc1 Protein Exosomes

To elucidate the expression profile of *Drosophila* S2 cell EVs, EV fractions were: i) collected by differential centrifugation and sucrose gradient sedimentation; ii) treated with RNase to digest non-specifically associated extravesicular cytoplasmic RNA; and iii) constructed into poly(A)+ libraries for deep sequencing.

While most mRNAs in the EV fraction (~96.6% of cellular mRNAs) were equal to or under-represented when compared to total cellular mRNAs, approximately 100 transcripts were enriched in the EV fraction by at least two-fold. Among the most abundant and enriched mRNAs was darc1. FIGS. 1A, 1B, 1C, and 1D. To determine if darc1 mRNA was present in vivo at the *Drosophila* larval neuromuscular junction (NMJ), fluorescent in situ hybridization (FISH) was performed with a double-labeled anti-horseradish peroxidase (HRP) preparation, an antibody that recognizes neuronal membrane antigens in insects to label the presynaptic compartment. Jan et al., "Antibodies to horseradish peroxidase as specific neuronal markers in *Drosophila* and in grasshopper embryos" *Proc Natl Acad Sci USA* 79:2700-2704 (1982). darc1 mRNA was present in a punctate pattern both inside presynaptic boutons and muscles, but was particularly enriched at the muscle postsynaptic junctional region, the region of the muscle immediately adjacent to the HRP label. FIG. 2A. The FISH signal was largely specific since it was severely reduced in a predicted darc1 null mutant, darc1esm113. FIG. 2B; and Mattaliano et al., "The *Drosophila* ARC homolog regulates behavioral responses to starvation. *Mol Cell Neurosci* 36:211-221 (2007). To establish if dArc1 protein was also observed at these sites, a polyclonal anti-dArc1 antibody was generated which identified that dArc1 was also present both pre- and postsynaptically at the NMJ, in a pattern very similar to the RNA localization. FIG. 2C. An improved darc1 null mutant (darc1E8) was generated via a CRISPR/Cas9 complex, that avoids creation of the darc1esm113 deletion which spans into the putative darc2 promoter region. In darc1E8/darc1esm113 and darc1wsm113 mutants there was a similar reduction in darc1 RNA and dArc1 protein but a residual signal was still observed. FIGS. 2B and 2D.

Example X

RNA Sequencing

Exosomes were treated with micrococcal nuclease (NEB), and then both exosomes and cell pellets were treated with RLT buffer (Qiagen) and RNA was extracted using RNeasy micro Kit (qiagen). Libraries were prepared using NEBNext Ultra directional RNA library prep kit for Illumina sequencing. Library 1 was subjected to single end sequencing with 18934428 and 13513146 reads for cell and exosomes respectively. Libraries 2, 3 and 4 were pair end-sequenced using miSeq illumina. Where library 2 had 1745707 exosome and 2188190 cell reads, library 3 had 2921143 exosome and 1823805 cell reads and library 4 had 3649518 exosome and 5047915 cell reads. Reads from each library were sorted by barcode, and adapter sequences removed.

Reads were then mapped using TopHat2 to the *Drosophila* genome, transcript expression was measured using Cufflinks, and differential expression was determined using DeSeq2. Kim et al., "TopHat2: accurate alignment of transcriptomes in the presence of insertions, deletions and gene fusions" *Genome Biol* 14:R36 (2013); Trapnell et al., "Differential gene and transcript expression analysis of RNA-seq experiments with TopHat and Cufflinks" *Nat Protoc* 7:562-578 (2012); and Love et al., "Moderated estimation of fold change and dispersion for RNA-seq data with DESeq2" *Genone Biol* 15:550 (2014).

For transposon mapping reads, reads from each library were mapped to common *Drosophila* transposon sequences using Bowtie2, expression was then measured using eXpress and DeSeq2. www.fruitfly.org/p_disrupt/TE; Langmead et al., "Ultrafast and memory efficient alignment of short DNA sequences to the human genome" *Genome Biol* 10:R25 (2009); and Roberts et al., "Streaming fragment assignment for real-time analysis of sequencing experiments. *Nat Methods* 10:71-73 (2013).

Example XI

Proteomic Analysis

Purified exosomes and cell pellets were diluted in loading buffer incubated at 95° C. for 15 min, and resolved by SDS-PAGE in a 4-20% gradient gel under reducing and denaturing conditions. Proteins were run 2 cm into the resolving gel, and then excised, and processed for mass spectrometry analysis.

Example XII

In Gel Digestion

Gel slices were cut into 1×1 mm pieces and placed in 1.5 mL eppendorf tubes with 1 mL of water for 30 min. The water was removed and 150 μL of 250 mM ammonium bicarbonate was added. For reduction 20 μL of a 45 mM solution of 1,4 dithiothreitol (DTT) was added and the samples were incubated at 50° C. for 30 min. The samples were cooled to room temperature and then for alkylation 20 μL of a 100 mM iodoacetamide solution was added and allowed to react for 30 min. The gel slices were washed 2× with mL water aliquots. The water was removed and 1 mL of 50:50 (50 mM Ammonium Bicarbonate: Acetonitrile) was placed in each tube and samples were incubated at room temperature for 1 hr. The solution was then removed and 200 μL of acetonitrile was added to each tube at which point the gels slices turned opaque white. The acetonitrile was removed and gel slices were further dried in a Speed Vac. Gel slices were rehydrated in 100 μL of 4 ng/μL trypsin (Sigma or Promega sequencing grade) in 0.01% ProteaseMAX Surfactant (Promega): 50 mM Ammonium Bicarbonate. Additional bicarbonate buffer was added to ensure complete submersion of the gel slices. Samples were incubated at 37° C. for 21 hrs. The supernatant of each sample was then removed and placed in a separate 1.5 mL eppendorf tube. Gel slices were further dehydrated with 100 μL of 80:20 (Acetonitrile: 1% formic acid). The extract was combined with the supernatants of each sample. The samples were then dried down in a Speed Vac. Samples were dissolved in 25 μL of 5% Acetonitrile in 0.1% trifluroacetic acid prior to injection on LC/MS/MS.

Example XIII

LC/MS/MS

A 3.0 μl aliquot was directly injected onto a custom packed 2 cm×100 μm C18 Magic 5μ particle trap column. Peptides were then eluted and sprayed from a custom packed emitter (75 μm×25 cm C18 Magic 3 μm particle) with a linear gradient from 95% solvent A (0.1% formic acid in water) to 35% solvent B (0.1% formic acid in Acetonitrile) in 90 minutes at a flow rate of 300 nanoliters per minute on a Waters Nano Acquity UPLC system. Data dependent acquisitions were performed on a Q Exactive mass spectrometer (Thermo Scientific) according to an experiment where full MS scans from 300-1750 m/z were acquired at a resolution of 70,000 followed by 10 MS/MS scans acquired under HCD fragmentation at a resolution of 17,500 with an isolation width of 1.6 Da. Raw data files were processed with Proteome Discoverer (version 1.4) prior to searching with Mascot Server (version 2.5) against the Uniprot database. Search parameters utilized were fully tryptic with 2 missed cleavages, parent mass tolerances of 10 ppm and fragment mass tolerances of 0.05 Da. A fixed modification of carbamidomethyl cysteine and variable modifications of acetyl (protein N-term), pyro glutamic for N-term glutamine, oxidation of methionine and serine/threonine phosphorylation were considered. Search results were loaded into the Scaffold Viewer (Proteome Software, Inc.) for assessment of protein identification probabilities and label free quantitation.

Example IVX

RNA Immnoprecipitation With Real Time Quantitative PCR

For S2 cell preparations, cells were raised in serum free medium, as above, and then centrifuged at 300×g to pellet the cells. Once pelleted, cells were resuspended in RIPA buffer (Abcam), and homogenized using 0.5 mm glass beads at 4° C. using a BBX24B Bullet Blender Blue homogenizer (Next Advance Inc.). Larval body wall muscles from wild type animals were homogenized in RIPA buffer (Abcam), and homogenized as above. Supernatants were cleared against magnetic beads (Pierce), and then incubated with either anti-dArc1, or equal amounts of preimmune serum. Samples were incubated overnight with serum and magnetic beads, and washed several times with RIPA buffer. Finally, beads were either incubated directly with 5× loading buffer (4% SDS, 250 mM Tris, Bromphenol blue, 30% glycerol, and 2-Mercaptoethanol) for western blot, or RNA was eluted from the beads with RLT buffer (Qiagen) and then purified using the RNeasy micro kit (Qiagen). RNA samples from both conditions were DNase treated with TurboDNase (ThermoFisher) and then equal volumes were reverse transcribed into cDNA using Superscript III (ThermoFisher). The RT-quantitative PCRs were performed in triplicate in a 96-well plate (BioRad) using a CFX96 system (BioRad). For the reactions, a Sybr green master mix (ThermoFisher) was used with the following gene specific primer sets (see table below) for dArc1 and 18S rRNA. RpL32 was used as a reference gene. All transcript levels were normalized to RpL32 transcript level, using the same cDNA template. Data were expressed in graphs as ΔCT. For RTq-PCR on body wall preparations, 5 larvae per genotype were dissected and RNA was purified from Brains and body wall muscles separately using RNeasy kit (Qiagen). All cDNA for body wall preparation analysis was synthesized with 100 ng of RNA, and then samples were treated as above for qRT-PCR. Primers

```
Forward dArc1:
                                        (SEQ ID NO: 9)
TGGCCCAGCTTACACAGATG

Reverse dArc1:
                                        (SEQ ID NO: 10)
GAAGTTGCCTTTGCCTCTGC

Forward 18S:
                                        (SEQ ID NO: 11)
CACAGAACATGAACCTTATGGGACGTGTG

Reverse 18S:
                                        (SEQ ID NO: 12)
TCGGTACAAGACCATACGATCTGC

Forward RpL32:
                                        (SEQ ID NO: 13)
ATGCTAAGCTGTCGCACAAATG

Reverse RpL32:
                                        (SEQ ID NO: 14)
GTTCGATCCGTAACCGATGT

Forward Copia:
                                        (SEQ ID NO: 15)
GGGATCAGGCAACCCGAATGAG

Reverse Copia:
                                        (SEQ ID NO: 16)
CTATTATCCTCTTCATTATAGGATATCTGAGGCTTAGTC

Forward GFP:
                                        (SEQ ID NO: 17)
CGACCACATGAAGCAGCACGACTTCTTC

Reverse GFP:
                                        (SEQ ID NO: 18)
CCTCGGCGCGGGTCTTGTAGTTGC

Forward dArc2:
                                        (SEQ ID NO: 19)
AAGAGGAACCGCCATCCAAG

Reverse dArc2:
                                        (SEQ ID NO: 20)
CTTTAGCGCATCCTTGTCGC
```

Example XV

Western Blotting

Extracts from RIP experiments were incubated at 95° C. for 15 min, and resolved by SDS-PAGE in a 4-20% gradient gel under reducing and denaturing conditions. Proteins were transferred onto nitrocellulose membrane (Bio-Rad) and blocked in 5% instant nonfat dry milk in TBST (50 mM Tris (pH 7.4), 150 mM NaCl, 0.05% Tween 20) and incubated with primary antibodies (diluted to working concentration in blocking solution) overnight at 4° C. After washing in TBST, blots were incubated with HRP-conjugated secondary antibodies diluted 1:3000 in blocking solution for 1 h at room temperature. Western blots were visualized using the SuperSignal West Femto Maximum Sensitivity Substrate kit (ThermoFisher). Blots were imaged using Chemidoc Touch imaging system (BioRad).

Example XVI

Activity Paradigm

Fly larva were dissected in low calcium HL3 saline, and then pulsed with high potassium saline at 2 minute intervals, separated by 15 minutes of rest for three repetitions. The final two stimulations were done for 4 and 6 minutes respectively, still separated by 15 minutes of rest. Samples were then fixed and processed as above. Ataman et al., "Rapid activity-dependent modifications in synaptic structure and function require bidirectional wnt signaling" Neuron 57:705-718 (2008); and Stewart et al., "Improved stability of *Drosophila* larval neuromuscular preparations in haemolymph-like physiological solutions" *J Comp Physiol A* 175:179-191 (1994)

Example XVII dArc1 Capsid Formation

The Arc open reading frame was cloned into pENTR (Thermo Fisher), its sequence confirmed and pENTR-Arc was subsequently recombined using LR Clonase (Thermo Fisher) with the pDEST-HisMbp Destination vector to generate His-MBP-dArc1. Expression induction and purification under native conditions (Ni-NTA column, Qiagen) were performed following standard procedures. Nallamsetty et al., "Gateway vectors for the production of combinatorially-tagged His6-MBP fusion proteins in the cytoplasm and periplasm of *Escherichia coli" Protein Sci* 14:2964-2971 (2005).

To generate soluble protein for ultrastructural studies, protein was diluted to ~1 mg/ml and cleaved at 30 degrees C. with AcTEV (Thermo-Fisher) followed by removal of the His-MBP tag and the His tagged TEV by binding to a Ni-NTA column and dialysis against PBS.

Example XVIII

Electron Microscopy of dArc1 Capsid

After formation of dArc1 capsids, the capsids were examined using negative staining. Capsids were fixed in 2% paraformaldehyde overnight at 4° C. 5 μL of fixed capsids were spotted onto formvar coated grids, after 20 min absorption grids were rinsed with PBS and then fixed with 1% glutaraldehyde for 5 min. Finally, samples were washed with water and then counter-stained with 2% w/v uranyl acetate, and blotted dry. Samples were imaged on an FEI EM 10 electron microscope at 80 kv.

Example IXX

ImmunoEM of Exosomes

Exosome preparations were fixed overnight in a final concentration of 2% paraformaldehyde (EM grade) at 4° C. After fixation, solution was gently pipetted up and down several times to resuspend exosomes. Formvar® coated grids (EMS) were glow discharged, spotted with 4 μL of exosomes, and incubated for 10 minutes at room temperature. Excess solution was removed by gently wicking liquid off of the grid on #50 filter paper. Grids were washed 2 times, 3 min each, in 100 mM Tris, followed by 4 washes, 3 min each, in 100 mM Tris+50 mM Glycine.

Grids were blocked for 10 min with 100 mM Tris+0.1% BSA. After block, exosomes were either incubated in 100 mM Tris (control) or lysed with 0.05% saponin in 100 mM Tris. Grids were washed for 2 min with 100 mM Tris followed by an anti-dArc1 antibody (1/500 in 100 mM Tris) incubation for 1 hr. Grids were then washed 5 times, 3 min each, in 100 mM Tris, followed by a 30 min incubation of Donkey anti-rabbit conjugated to 10 nm gold (Jackson Immunoresearch) secondary (1:60 dilution in 100 mM Tris). Grids were washed 8 times, 2 min each, in 100 mM Tris, and then fixed with 1% gluteraldehyde in 100 mM Tris for 1 min at room temperature. Finally, grids were washed again 8 times, 2 min each, with distilled water, and then negative stained with 1% uranyl acetate for 30 seconds. Finally, grids were imaged on an FEI EM 10 as above.

Example XX

Statistical Analysis

Statistical analysis was performed using a Student's t test when a single experimental sample was compared with control. For comparison of multiple experimental groups with a single control, a one-way analysis of variance was used followed by a Tukey's post hoc test. *,$p<0.05$; , $p<0.001$; *, $p<0.0001$.

Example XXI

Verification of Exosome Formation

The expression of arc gene fragments were performed according to Example VIII where the media containing the expression products were incubated with naïve cells followed by a measurement of GFP intensity in the cells. The data show a lack of GFP intensity in cells subsequent to incubation with pAGW expression product media. See, FIG. 13A. In contrast, significant GFP intesity was observed in cells subsequent to incubation with arc 3' UTR expression product media. See, FIG. 13B. These data suggest that the arc 3'UTR gene expression product formed an exosome that transferred into the cell, wherease the negative control pAGW expression product failed to form an exosome.

We claim:

1. An extracellular vesicle comprising:

i) an encapsulated *Drosophila* activity-regulated cytoskeleton 1 (darc1) protein;

ii) a nucleic acid comprising a fragment of a darc1 messenger ribonucleic acid 3' untranslated region (darc1 mRNA 3' UTR) that is the sequence of SEQ ID NO: 2 or SEQ ID NO 3 and bound to said darc1 protein; and iii) a non-arc nucleic acid payload fused to said nucleic acid of part (ii).

2. The extracellular vesicle of claim 1, wherein said non-arc nucleic acid payload is a deoxyribonucleic acid sequence or a ribonucleic acid sequence.

3. The extracellular vesicle of claim 1, wherein said compound is non-arc nucleic acid payload encodes a protein.

4. The extracellular vesicle of claim 1, wherein said non-arc nucleic acid payload is selected from the group consisting of an siRNA, an shRNA and an RNAi.

5. The extracellular vesicle of claim 1, wherein said extracellular vesicle is a nucleic acid delivery platform.

6. The extracellular vesicle of claim 1, wherein said extracellular vesicle is an arc protein capsid.

7. The extracellular vesicle of claim 1, wherein said nucleic acid payload further encodes an actin promoter.

* * * * *